(12) United States Patent
Bestetti et al.

(10) Patent No.: US 7,781,189 B2
(45) Date of Patent: Aug. 24, 2010

(54) CATALYZING TRANSGLYCOSYLATION USING A RECOMBINANT HOST CELL OVEREXPRESSING URIDINE PHOSPHORYLASE AND PURINE NUCLEOSIDE PHOSPHORYLASE

(75) Inventors: Giuseppina Bestetti, Agrate Brianza (IT); Simona Cali, Abbiategrasso (IT); Daniela Ghisotti, Milan (IT); Gaetano Orsini, Varese (IT); Giancarlo Tonon, Pula (IT); Gabriele Zuffi, Novate Milanese (IT)

(73) Assignee: Bio-Ker S.R.L., Gessate (IT)

( * ) Notice: Subject to any disclaimer, the term of this patent is extended or adjusted under 35 U.S.C. 154(b) by 1026 days.

(21) Appl. No.: 11/036,497

(22) Filed: Jan. 14, 2005

(65) Prior Publication Data

US 2005/0142645 A1 Jun. 30, 2005

Related U.S. Application Data

(63) Continuation of application No. 09/891,865, filed on Jun. 25, 2001, now Pat. No. 6,911,341, which is a continuation of application No. PCT/EP99/010416, filed on Dec. 23, 1999.

(30) Foreign Application Priority Data

Dec. 23, 1998 (IT) .............................. MI98A2792

(51) Int. Cl.
*C12P 19/38* (2006.01)
*C12N 9/10* (2006.01)
(52) U.S. Cl. ........................................ 435/87; 435/193
(58) Field of Classification Search ........................ None
See application file for complete search history.

(56) References Cited

U.S. PATENT DOCUMENTS

| 4,347,315 | A | * | 8/1982 | Krenitsky et al. ............. 435/87 |
| 4,835,104 | A | | 5/1989 | Yokozeki et al. |
| 5,563,049 | A | | 10/1996 | Kojima et al. |
| 6,197,552 | B1 | | 3/2001 | Yokozeki et al. |

FOREIGN PATENT DOCUMENTS

| EP | 0002192 | | 6/1979 |
| EP | 0038568 | | 10/1981 |
| EP | 0423641 | * | 4/1991 |
| JP | 54095794 A | | 7/1979 |
| JP | 56164793 A | | 12/1981 |
| JP | 02308797 A | | 12/1990 |
| JP | 6-253854 | | 9/1994 |
| WO | 00/39307 A2 | * | 7/2000 |

OTHER PUBLICATIONS

Brykun et al. "Cloning the *Escherichia coli* uridine phosphorylase gene (udp) and its expression in the recombinant plasmids" Genetika XXV:1717-1724, 1989.*

"The Recombinant Protein Handbook, Protein Amplification and Simple Purification", Amersham, 2001, p. 59.*
Spoldi et al., "Recombinant bacterial cells as efficient biocatalysts for the production of nucleosides", Nucleosides Nucleotides Nucleic Acids 20:977-979, 2001.*
GenBank Accession No. J01749 (Mar. 1992).*
Sambrook et al., "Molecular Cloning, a Laboratory Manual, Second Edition", Cold Spring Harbor Press, 1989, pp. 1.5-1.6.*
EMBL Accession No. X15689 (Nov. 1989).*
EMBL Accession No. M60917 (Sep. 1991).*
Novagen 1997 Catalog, pp. 42-43 and 156.*
Walton et al., "Nucleotide sequence of the *Escherichia coli* uridine phosphorylase (udp) gene", Nucleic Acids Res 17:6741, 1989.*
Hershfield et al., Use of site-directed mutagenesis to enhance the epitope-shielding effect of covalent modification proteins with polyethylene glycol, PNAS, USA 88:7185-7189, 1991.*
Bulow et al., "Multienzyme systems obtained by gene fusion", Trends Biotech 9:226-231, 1991.*
Lee et al., J. Liquid Chromat. 15:2831-2841, 1992.*
Cudny et al., J. Biol. Chem. 261:6450-6453, 1986.*
Ausubel et al., Current Protocols in Molecular Biology, John Wiley and Sons, Inc., 1995, p. 16.1.1.
Database GenBank Accession No. L08752, Apr. 1993.
Branden et al., "Introduction to Protein Structure", Garland Publishing Inc., New York, 1991, p. 247.
Witkowski et al. (1999) Biochemistry 38:11643-11650.
Takehara, M. et al.; "Molecular cloning and nucleotide sequence of purine nucleoside phosphorylase and uridine phosphorylase genes from Klebsiella sp.", Bioscience, Biotechnology and Biochemistry, vol. 59, No. 10, 1995, pp. 1987-1990.

OTHER PUBLICATIONS

Krenitsky, T.A. et al.., "Purine nucleoside synthesis, an efficient method employing nucleoside phosphorylases," Biochemistry, vol. 20, 1981, pp. 3615-3621.
Mikhailopulo, I.A. et al., "1-deaza and 3-deazapurines in the reaction of microbiological transglycosylation", Biotechnology Letters, vol. 14, No. 10, Oct. 1992 (1992-10), pp. 885-890.
Krenistsky, T.A. et al., "An enzymic synthesis of purine D-arabinonucleosides", Carbohydrate Research, vol. 97, 1981, pp. 139-146.
Mikhailopuolo, A.I. et al.; "Benzimidazoles in the reaction of enzymatic transglycosylation", Nucleosides & Nucleotides, vol. 14, No. 3-5, 1995, pp. 477-480.
Mayer, M.P.; "A new set of useful cloning and expression vectors derived from pBlueScript", Gene, NL, Elsevier Biomedical Press Amsterdam, vol. 163, No. 1, Sep. 22, 1995, pp. 41-46.

(Continued)

*Primary Examiner*—David J Steadman
(74) *Attorney, Agent, or Firm*—Merchant & Gould P.C.

(57) ABSTRACT

Novel strains of genetically modified prokaryotic micro-organisms capable of expressing polypeptides having the enzyme activity of the enzymes uridine phosphorylase (UdP) and purine nucleoside phosphorylase (PNP) are described; the strains in question can be used, both in the form of whole cells and in the form of crude or purified extracts, to catalyse transglycosylation reactions between a donor nucleoside and an acceptor base with particularly high yields. The associated plasmid vectors are also described.

13 Claims, 6 Drawing Sheets

OTHER PUBLICATIONS

Zintchenko AI.I. et al.; "Substrate specificity of uridine and purine nucleoside phosphorylases of the whole cells of *Escherichia coli*", Nucleic Acids Research Symposium Series, vol. 18, 1987, pp. 137-140.

PCT International Search Report (PCT/ISA/210) 9 pages from PCT/EP 99/10416.

PCT Partial International Search Results Communication (PCTISA/206) 4 pages from PCT/EP/99/0416.

Aldea et al., "Generation of a Detailed Physical and Genetic Map of the ilv-metE-udp Region of the *Escherichia coli* Chromosome", J. Mol. Biol. (1988) 200: 427-438.

Fischer et al., "The cloning of the *Escherichio coli* K-12 deoxyrilionucleoside operon", Gene, 1 (1982) 291-298.

Jobling et al., 1990. "Construction of vectors with the p15a replicon, kanamycin resistance, inducible lacZa and pUC18 or pUC19 multiple cloning sites", Nucleic Acids Research, vol. 18, N17, 5315-5316.

* cited by examiner

FIG. 2A

```
                                      EcoRI                KpnI                                   SalI             SphI      HindIII
RBS
AGGAAAACAGCT ATG ACC ATG ATT ACG AAT TCG AGC TCG GTA CCC GGG GAT CCT CTA GAG TCG ACC TGC AGG CAT GCA AGC TTG
             thr met ile thr asn ser ser val pro gly asp pro leu glu ser thr cys arg his ala ser leu
```

FIG. 2B

```
                                      EcoRI                                                         SalI
RBS
AGGAAAACAGCT ATG ACC ATG ATT ACG AAT TCT TCC ATG GCT ACC CCA..........TGG GCG TAA AGAGTAAGTCGACCTGC.....
             thr met ile thr asn ser met ala thr pro..........trp ala stop
```

FIG. 2C

```
                                      EcoRI                KpnI                                                  SalI
RBS
AGGAAAACAGCT ATG ACC ATG ATT ACG AAT TCG AGC TCG GTA CCA TCC ATG TCC........CTG CTG TAA TTCTCTTGTCGCAATG.....
             thr met ile thr asn ser ser val pro ser met ser........leu leu stop
```

FIG. 2D

```
SalI/NheI RBS  EcoRI                                                    SalI              SphI
GTCGACTAGCAGGAGGAATTCTTCC ATG GCT ACC CCA..........TGG GCG TAA AGAGTAAGTCGACCTGCAGGCATGCAA
                          met ala thr pro..........trp ala stop
```

FIG. 5
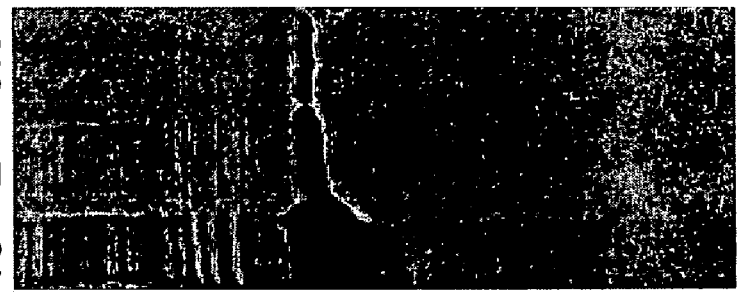
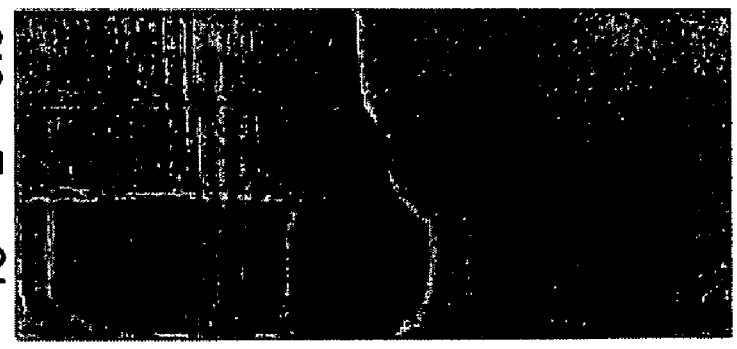
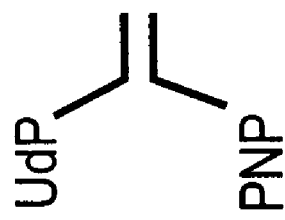

SEQUENCE LISTING

<160> NUMBER OF SEQ ID NOS: 33

<210> SEQ ID NO 1
<211> LENGTH: 3444
<212> TYPE: DNA
<213> ORGANISM: Artificial Sequence
<220> FEATURE:
<223> OTHER INFORMATION: plasmid
<220> FEATURE:

<221> NAME/KEY: gene
<222> LOCATION: (243)..(1021)
<223> OTHER INFORMATION: udp

<400> SEQUENCE: 1

```
gcgcccaata cgcaaaccgc ctctccccgc gcgttggccg attcattaat gcagctggca    60
cgacaggttt cccgactgga aagcgggcag tgagcgcaac gcaattaatg tgagttagct   120
cactcattag gcaccccagg ctttacactt tatgcttccg gctcgtatgt tgtgtggaat   180
tgtgagcgga taacaatttc acacaggaaa cagctatgac catgattacg aattcgagct   240
cggtaccatc catgtccaag tctgatgttt ttcatctcgg cctcactaaa aacgatttac   300
aaggggctac gcttgccatc gtccctggcg acccggatcg tgtggaaaag atcgccgcgc   360
tgatggataa gccggttaag ctggcatctc accgcgaatt cactacctgg cgtgcagagc   420
tggatggtaa acctgttatc gtctgctcta ccggtatcgg cggcccgtct acctctattg   480
ctgttgaaga gctggcacag ctgggcattc gcacttcct gcgtatcggt acaacgggcg   540
ctattcagcc gcatattaat gtgggtgatg tcctggttac cacggcgtct gtccgtctgg   600
atggcgcgag cctgcacttc gcaccgctgg aattcccggc tgtcgctgat ttcgaatgta   660
cgactgcgct ggttgaagct gcgaaatcca ttggcgcgac aactcacgtt ggcgtgacag   720
cttcttctga taccttctac ccaggtcagg aacgttacga tacttactct ggtcgcgtag   780
ttcgtcactt taaaggttct atggaagagt ggcaggcgat gggcgtaatg aactatgaaa   840
tggaatctgc aaccctgctg accatgtgtg caagtcaggg cctgcgtgcc ggtatggtag   900
cgggtgttat cgttaaccgc acccagcaag agatcccgaa tgctgagacg atgaaacaaa   960
ccgaaagcca tgcggtgaaa atcgtggtgg aagcggcgcg tcgtctgctg taattctctt  1020
gtcgacctgc aggcatgcaa gcttggcact ggccgtcgtt ttacaacgtc gtgactggga  1080
aaaccctggc gttacccaac ttaatcgcct tgcagcacat cccccttcg ccagctggcg  1140
taatagcgaa gaggcccgca ccgatcgccc ttcccaacag ttgcgcagcc tgaatggcga  1200
atggcgcctg atgcggtatt ttctccttac gcatctgtgc ggtatttcac accgcatatg  1260
gtgcactctc agtacaatct gctctgatgc cgcatagtta agccagcccc gacacccgcc  1320
aacacccgct gacgcgccct gacgggcttg tctgctcccg gcatccgctt acagacaagc  1380
tgtgaccgtc tccgggagct gcatgtgtca gaggttttca ccgtcatcac cgaaacgcgc  1440
gagacgaaag gcctcgtgat acgcctattt ttataggtt aatgtcatga taataatggt  1500
ttcttagacg tcaggtggca cttttcgggg aaatgtgcgc ggaacccta tttgtttatt  1560
tttctaaata cattcaaata tgtatccgct catgagacaa taaccctgat aaatgcttca  1620
ataatattga aaaggaaga gtatgagtat tcaacatttc cgtgtcgccc ttattcctt  1680
ttttgcggca ttttgccttc ctgtttttgc tcacccagaa acgctggtga agtaaaaga  1740
tgctgaagat cagttgggtg cacgagtggg ttacatcgaa ctggatctca acagcggtaa  1800
gatccttgag agttttcgcc ccgaagaacg ttttccaatg atgagcactt ttaaagttct  1860
gctatgtggc gcggtattat cccgtattga cgccgggcaa gagcaactcg gtcgccgcat  1920
acactattct cagaatgact tggttgagta ctcaccagtc acagaaaagc atcttacgga  1980
tggcatgaca gtaagagaat tatgcagtgc tgccataacc atgagtgata acactgcggc  2040
caacttactt ctgacaacga tcggaggacc gaaggagcta accgcttttt tgcacaacat  2100
gggggatcat gtaactcgcc ttgatcgttg ggaaccggag ctgaatgaag ccataccaaa  2160
cgacgagcgt gacaccacga tgcctgtagc aatggcaaca acgttgcgca aactattaac  2220
```

```
tggcgaacta cttactctag cttcccggca acaattaata gactggatgg aggcggataa    2280
agttgcagga ccacttctgc gctcggccct tccggctggc tggtttattg ctgataaatc    2340
tggagccggt gagcgtgggt ctcgcggtat cattgcagca ctggggccag atggtaagcc    2400
ctcccgtatc gtagttatct acacgacggg gagtcaggca actatggatg aacgaaatag    2460
acagatcgct gagataggtg cctcactgat taagcattgg taactgtcag accaagttta    2520
ctcatatata ctttagattg atttaaaact tcattttta tttaaaagga tctaggtgaa    2580
gatccttttt gataatctca tgaccaaaat cccttaacgt gagttttcgt tccactgagc    2640
gtcagacccc gtagaaaaga tcaaaggatc ttcttgagat ccttttttc tgcgcgtaat    2700 ctgctgcttg caaacaaaaa aaccaccgct accagcggtg gtttgtttgc cggatcaaga    2760
gctaccaact ctttttccga aggtaactgg cttcagcaga gcgcagatac caaatactgt    2820
ccttctagtg tagccgtagt taggccacca cttcaagaac tctgtagcac cgcctacata    2880
cctcgctctg ctaatcctgt taccagtggc tgctgccagt ggcgataagt cgtgtcttac    2940
cgggttggac tcaagacgat agttaccgga taaggcgcag cggtcgggct gaacggggggg    3000 ttcgtgcaca cagcccagct tggagcgaac gacctacacc gaactgagat acctacagcg    3060
tgagctatga gaaagcgcca cgcttcccga agggagaaag gcggacaggt atccggtaag    3120
cggcagggtc ggaacaggag agcgcacgag ggagcttcca gggggaaacg cctggtatct    3180
ttatagtcct gtcgggtttc gccacctctg acttgagcgt cgattttgt gatgctcgtc    3240 agggggcgg agcctatgga aaaacgccag caacgcggcc ttttacggtt cctggccttt    3300
ttgctggcct tttgctcaca tgttctttcc tgcgttatcc cctgattctg tggataaccg    3360
tattaccgcc tttgagtgag ctgataccgc tcgccgcagc cgaacgaccg agcgcagcga    3420
gtcagtgagc gaggaagcgg aaga                                          3444
```

```
<210> SEQ ID NO 2
<211> LENGTH: 5556
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (243)..(1021)
<223> OTHER INFORMATION: udp
<220> FEATURE:
<221> NAME/KEY: gene
<222> LOCATION: (1483)..(2883)
<223> OTHER INFORMATION: tetracycline resistance

<400> SEQUENCE: 2
```

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg aattcgagct    240
cggtaccatc catgtccaag tctgatgttt ttcatctcgg cctcactaaa aacgatttac    300 aagggctac gcttgccatc gtccctggcg accggatcg tgtggaaaag atcgccgcgc    360
tgatggataa gccggttaag ctggcatctc accgcgaatt cactacctgg cgtgcagagc    420
tggatggtaa acctgttatc gtctgctcta ccggtatcgg cggcccgtct acctctattg    480
ctgttgaaga gctggcacag ctgggcattc gcaccttcct gcgtatcggt acaacgggcg    540
```

```
ctattcagcc gcatattaat gtgggtgatg tcctggttac cacgcgtctg gtccgtctgg    600
atggcgcgag cctgcacttc gcaccgctgg aattcccggc tgtcgctgat ttcgaatgta    660
cgactgcgct ggttgaagct gcgaaatcca ttggcgcgac aactcacgtt ggcgtgacag    720
cttcttctga taccttctac ccaggtcagg aacgttacga tacttactct ggtcgcgtag    780
ttcgtcactt taaaggttct atggaagagt ggcaggcgat gggcgtaatg aactatgaaa    840
tggaatctgc aaccctgctg accatgtgtg caagtcaggg cctgcgtgcc ggtatggtag    900
cgggtgttat cgttaaccgc acccagcaag agatcccgaa tgctgagacg atgaaacaaa    960
ccgaaagcca tgcggtgaaa atcgtggtgg aagcggcgcg tcgtctgctg taattctctt   1020
gtcgacctgc aggcatgcaa gctttatgct tgtaaaccgt tttgtgaaaa aattttaaa    1080 ataaaaaagg ggacctctag ggtccccaat taattagtaa tataatctat taaaggtcat   1140 tcaaaggtc atccaccgga tcagcttagt aaagccctcg ctagatttta atgcggatgt    1200
tgcgattact tcgccaacta ttgcgataac aagaaaaagc cagcctttca tgatatatct   1260
cccaatttgt gtagggctta ttatgcacgc ttaaaaataa taaaagcaga cttgacctga   1320
tagtttggct gtgagcaatt atgtgcttag tgcatctaac gcttgagtta agccgcgccg   1380
cgaagcggcg tcggcttgaa cgaattgtta gacattattt gccgactacc ttggtgatct   1440
cgcctttcac gtagtggaca aattcttcca actgatctgc gcgccgagat gcgccgcgtg   1500
cggctgctgg agatggcgga cgcgatggat atgttctgcc aagggttggt tgcgcattc    1560 acagttctcc gcaagaattg attggctcca attcttggag tggtgaatcc gttagcgagg   1620
tgccgccggc ttccattcag gtcgaggtgg cccggctcca tgcaccgcga cgcaacgcgg   1680
ggaggcagac aaggtatagg gcggcgccta caatccatgc caacccgttc catgtgctcg   1740
ccgaggcggc ataaatcgcc gtgacgatca gcggtccagt gatcgaagtt aggctggtaa   1800
gagccgcgag cgatccttga agctgtccct gatggtcgtc atctacctgc ctggacagca   1860
tggcctgcaa cgcgggcatc ccgatgccgc cggaagcgag aagaatcata atggggaagg   1920
ccatccagcc tcgcgtcgcg aacgccagca agacgtagcc cagcgcgtcg gccgccatgc   1980
cggcgataat ggcctgcttc tcgccgaaac gtttggtggc gggaccagtg acgaaggctt   2040
gagcgagggc gtgcaagatt ccgaataccg caagcgacag gccgatcatc gtcgcgctcc   2100
agcgaaagcg gtcctcgccg aaaatgaccc agagcgctgc cggcacctgt cctacgagtt   2160
gcatgataaa gaagacagtc ataagtgcgg cgacgatagt catgcccgc gcccaccgga    2220 aggagctgac tgggttgaag gctctcaagg gcatcggtcg acgctctccc ttatgcgact   2280
cctgcattag gaagcagccc agtagtaggt tgaggccgtt gagcaccgcc gccgcaagga   2340
atggtgcatg caaggagatg gcgcccaaca gtcccccggc cacggggcct gccaccatac   2400
ccacgccgaa acaagcgctc atgagcccga agtggcgagc ccgatcttcc ccatcggtga   2460
tgtcggcgat ataggcgcca gcaaccgcac ctgtggcgcc ggtgatgccg ccacgatgc    2520 gtccggcgta gaggatccac aggacgggtg tggtcgccat gatcgcgtag tcgatagtgg   2580
ctccaagtag cgaagcgagc aggactgggc ggcggccaaa gcggtcggac agtgctccga   2640
gaacgggtgc gcatagaaat tgcatcaacg catatagcgc tagcagcacg ccatagtgac   2700
tggcgatgct gtcggaatgg acgatatccc gcaagaggcc cggcagtacc ggcataacca   2760
agcctatgcc tacagcatcc agggtgacgg tgccgaggat gacgatgagc gcattgttag   2820
atttcataca cggtgcctga ctgcgttagc aatttaactg tgataaacta ccgcattaaa   2880
gctcatgcgg atcagtgagg gtttgcaact gcgggtcaag gatctggatt tcgatcacgg   2940
```

```
cacgatcatc gtgcgggagg gcaagggctc caaggatcgg gccttgatgt tacccgagag   3000
cttggcaccc agcctgcgcg agcaggggaa ttgatccggt ggatgacctt ttgaatgacc   3060
tttaatagat tatattacta attaattggg gaccctagag gtccccttt ttattttaaa    3120 aattttttca caaaacggtt tacaagcata aagcttggca ctggccgtcg ttttacaacg   3180
tcgtgactgg gaaaaccctg gcgttaccca acttaatcgc cttgcagcac atccccttt   3240 cgccagctgg cgtaatagcg aagaggcccg caccgatcgc ccttcccaac agttgcgcag   3300
cctgaatggc gaatggcgcc tgatgcggta ttttctcctt acgcatctgt gcggtatttc   3360
acaccgcata tggtgcactc tcagtacaat ctgctctgat gccgcatagt taagccagcc   3420
ccgacacccg ccaacacccg ctgacgcgcc ctgacgggct tgtctgctcc cggcatccgc   3480
ttacagacaa gctgtgaccg tctccgggag ctgcatgtgt cagaggtttt caccgtcatc   3540
accgaaacgc gcgagacgaa agggcctcgt gatacgccta ttttttatagg ttaatgtcat   3600 gataataatg gtttcttaga cgtcaggtgg cacttttcgg ggaaatgtgc gcggaacccc   3660
tatttgttta ttttcctaaa tacattcaaa tatgtatccg ctcatgagac aataaccctg   3720
ataaatgctt caataatatt gaaaaaggaa gagtatgagt attcaacatt tccgtgtcgc   3780
ccttattccc ttttttgcgg cattttgcct tcctgttttt gctcacccag aaacgctggt   3840
gaaagtaaaa gatgctgaag atcagttggg tgcacgagtg ggttacatcg aactggatct   3900
caacagcggt aagatccttg agagttttcg ccccgaagaa cgttttccaa tgatgagcac   3960
ttttaaagtt ctgctatgtg gcgcggtatt atcccgtatt gacgccgggc aagagcaact   4020
cggtcgccgc atacactatt ctcagaatga cttggttgag tactcaccag tcacagaaaa   4080
gcatcttacg gatggcatga cagtaagaga attatgcagt gctgccataa ccatgagtga   4140
taacactgcg gccaacttac ttctgacaac gatcggagga ccgaaggagc taaccgcttt   4200
tttgcacaac atgggggatc atgtaactcg ccttgatcgt tgggaaccgg agctgaatga   4260
agccatacca aacgacgagc gtgacaccac gatgcctgta gcaatggcaa caacgttgcg   4320
caaactatta actggcgaac tacttactct agcttcccgg caacaattaa tagactggat   4380
ggaggcggat aaagttgcag gaccacttct gcgctcggcc cttccggctg gctggtttat   4440
tgctgataaa tctggagccg gtgagcgtgg gtctcgcggt atcattgcag cactggggcc   4500
agatggtaag ccctcccgta tcgtagttat ctacacgacg gggagtcagg caactatgga   4560
tgaacgaaat agacagatcg ctgagatagg tgcctcactg attaagcatt ggtaactgtc   4620
agaccaagtt tactcatata ctttagat tgatttaaaa cttcatttt aatttaaaag      4680 gatctaggtg aagatccttt ttgataatct catgaccaaa atcccttaac gtgagttttc    4740
gttccactga gcgtcagacc ccgtagaaaa gatcaaagga tcttcttgag atccttttt     4800 tctgcgcgta atctgctgct tgcaaacaaa aaaaccaccg ctaccagcgg tggtttgttt    4860
gccggatcaa gagctaccaa ctcttttcc gaaggtaact ggcttcagca gagcgcagat     4920
accaaatact gtccttctag tgtagccgta gttaggccac cacttcaaga actctgtagc    4980
accgcctaca tacctcgctc tgctaatcct gttaccagtg gctgctgcca gtggcgataa    5040
gtcgtgtctt accgggttgg actcaagacg atagttaccg gataaggcgc agcggtcggg   5100
ctgaacgggg ggttcgtgca cacagcccag cttggagcga acgacctaca ccgaactgag    5160
atacctacag cgtgagctat gagaaagcgc cacgcttccc gaaggagaa aggcggacag     5220 gtatccggta agcggcaggg tcggaacagg agagcgcacg agggagcttc caggggggaaa   5280
```

-continued

```
cgcctggtat ctttatagtc ctgtcgggtt tcgccacctc tgacttgagc gtcgatttt      5340 gtgatgctcg tcagggggc ggagcctatg gaaaaacgcc agcaacgcgg ccttttacg      5400 gttcctggcc ttttgctggc cttttgctca catgttcttt cctgcgttat ccctgattc      5460 tgtggataac cgtattaccg cctttgagtg agctgatacc gctcgccgca gccgaacgac      5520
cgagcgcagc gagtcagtga gcgaggaagc ggaaga                               5556
```

<210> SEQ ID NO 3
<211> LENGTH: 3383
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (231)..(960)
<223> OTHER INFORMATION: deoD

<400> SEQUENCE: 3

```
gcgcccaata cgcaaaccgc ctctccccgc gcgttggccg attcattaat gcagctggca       60
cgacaggttt cccgactgga aagcgggcag tgagcgcaac gcaattaatg tgagttagct      120
cactcattag gcaccccagg ctttacactt tatgcttccg gctcgtatgt tgtgtggaat      180
tgtgagcgga taacaatttc acacaggaaa cagctatgac catgattacg aattcttcca      240
tggctacccc acacattaat gcagaaatgg gcgatttcgc tgacgtagtt ttgatgccag      300
gcgacccgct gcgtgcgaag tatattgctg aaactttcct tgaagatgcc cgtgaagtga      360
acaacgttcg cggtatgctg ggcttcaccg gtacttacaa aggccgcaaa atttccgtaa      420
tgggtcacgg tatgggtatc ccgtcctgct ccatctacac caaagaactg atcaccgatt      480
tcggcgtgaa gaaaattatc cgcgtgggtt cctgtggcgc agttctgccg cacgtaaaac      540
tgcgcgacgt cgttatcggt atgggtgcct gcaccgattc aaagttaac cgcatccgtt      600 ttaaagacca tgactttgcc gctatcgctg acttcgacat ggtgcgtaac gcagtagatg      660
cagctaaagc actgggtatt gatgctcgcg tgggtaacct gttctccgct gacctgttct      720
actctccgga cggcgaaatg ttcgacgtga tggaaaaata cggcattctc ggcgtggaaa      780
tggaagcggc tggtatctac ggcgtcgctg cagaatttgg cgcgaaagcc ctgaccatct      840
gcaccgtatc tgaccacatc cgcactcacg agcagaccac tgccgctgag cgtcagacta      900
ccttcaacga catgatcaaa atcgcactgg aatccgttct gctgggcgat aaagagtaag      960
tcgacctgca ggcatgcaag cttggcactg gccgtcgttt tacaacgtcg tgactgggaa     1020
aaccctggcg ttacccaact taatcgcctt gcagcacatc ccccttcgc cagctggcgt     1080 aatagcgaag aggcccgcac cgatcgccct tcccaacagt tgcgcagcct gaatggcgaa     1140
tggcgcctga tgcggtattt tctccttacg catctgtgcg gtatttcaca ccgcatatgg     1200
tgcactctca gtacaatctg ctctgatgcc gcatagttaa gccagccccg acacccgcca     1260
acacccgctg acgcgccctg acgggcttgt ctgctcccgg catccgctta cagacaagct     1320
gtgaccgtct ccgggagctg catgtgtcag aggttttcac cgtcatcacc gaaacgcgcg     1380
agacgaaagg gcctcgtgat acgcctattt ttataggtta atgtcatgat aataatggtt     1440
tcttagacgt caggtggcac ttttcgggga atgtgcgcg gaacccctat ttgtttattt     1500
ttctaaatac attcaaatat gtatccgctc atgagacaat aaccctgata aatgcttcaa     1560
taatattgaa aaaggaagag tatgagtatt caacatttcc gtgtcgccct tattcccttt     1620
tttgcggcat tttgccttcc tgttttgct cacccagaaa cgctggtgaa agtaaaagat     1680
```

```
gctgaagatc agttgggtgc acgagtgggt tacatcgaac tggatctcaa cagcggtaag    1740
atccttgaga gttttcgccc cgaagaacgt tttccaatga tgagcacttt taaagttctg    1800
ctatgtggcg cggtattatc ccgtattgac gccgggcaag agcaactcgg tcgccgcata    1860
cactattctc agaatgactt ggttgagtac tcaccagtca cagaaaagca tcttacggat    1920
ggcatgacag taagagaatt atgcagtgct gccataacca tgagtgataa cactgcggcc    1980
aacttacttc tgacaacgat cggaggaccg aaggagctaa ccgcttttt gcacaacatg    2040 ggggatcatg taactcgcct tgatcgttgg gaaccggagc tgaatgaagc cataccaaac    2100
gacgagcgtg acaccacgat gcctgtagca atggcaacaa cgttgcgcaa actattaact    2160
ggcgaactac ttactctagc ttcccggcaa caattaatag actggatgga ggcggataaa    2220
gttgcaggac cacttctgcg ctcggccctt ccggctggct ggtttattgc tgataaatct    2280
ggagccggtg agcgtgggtc tcgcggtatc attgcagcac tggggccaga tggtaagccc    2340
tcccgtatcg tagttatcta cacgacgggg agtcaggcaa ctatggatga acgaaataga    2400
cagatcgctg agataggtgc ctcactgatt aagcattggt aactgtcaga ccaagtttac    2460
tcatatatac tttagattga tttaaaactt catttttaat ttaaaaggat ctaggtgaag    2520
atcctttttg ataatctcat gaccaaaatc ccttaacgtg agttttcgtt ccactgagcg    2580
tcagaccccg tagaaaagat caaaggatct tcttgagatc cttttttct gcgcgtaatc    2640 tgctgcttgc aaacaaaaaa accaccgcta ccagcggtgg tttgtttgcc ggatcaagag    2700
ctaccaactc tttttccgaa ggtaactggc ttcagcagag cgcagatacc aaatactgtc    2760
cttctagtgt agccgtagtt aggccaccac ttcaagaact ctgtagcacc gcctacatac    2820
ctcgctctgc taatcctgtt accagtggct gctgccagtg gcgataagtc gtgtcttacc    2880
gggttggact caagacgata gttaccggat aaggcgcagc ggtcgggctg aacggggggt    2940
tcgtgcacac agcccagctt ggagcgaacg acctacaccg aactgagata cctacagcgt    3000
gagctatgag aaagcgccac gcttcccgaa gggagaaagg cggacaggta tccggtaagc    3060
ggcagggtcg gaacaggaga gcgcacgagg gagcttccag ggggaaacgc ctggtatctt    3120
tatagtcctg tcgggtttcg ccacctctga cttgagcgtc gatttttgtg atgctcgtca    3180
ggggggcgga gcctatggaa aaacgccagc aacgcggcct ttttacggtt cctggccttt    3240
tgctggcctt ttgctcacat gttctttcct gcgttatccc ctgattctgt ggataaccgt    3300
attaccgcct ttgagtgagc tgataccgct cgccgcagcc gaacgaccga gcgcagcgag    3360
tcagtgagcg aggaagcgga aga                                           3383

<210> SEQ ID NO 4
<211> LENGTH: 5495
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (231)..(960)
<223> OTHER INFORMATION: deoD
<220> FEATURE:
<221> NAME/KEY: gene
<222> LOCATION: (1423)..(2822)
<223> OTHER INFORMATION: tetracycline resistance

<400> SEQUENCE: 4
gcgcccaata cgcaaaccgc ctctccccgc gcgttggccg attcattaat gcagctggca    60
```

-continued

| | |
|---|---|
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatgac catgattacg aattcttcca | 240 |
| tggctacccc acacattaat gcagaaatgg gcgatttcgc tgacgtagtt ttgatgccag | 300 |
| gcgacccgct gcgtgcgaag tatattgctg aaactttcct tgaagatgcc cgtgaagtga | 360 |
| acaacgttcg cggtatgctg ggcttcaccg gtacttacaa aggccgcaaa atttccgtaa | 420 |
| tgggtcacgg tatgggtatc ccgtcctgct ccatctacac caaagaactg atcaccgatt | 480 |
| tcggcgtgaa gaaaattatc cgcgtgggtt cctgtgcgc agttctgccg cacgtaaaac | 540 |
| tgcgcgacgt cgttatcggt atgggtgcct gcaccgattc caaagttaac cgcatccgtt | 600 |
| ttaaagacca tgactttgcc gctatcgctg acttcgacat ggtgcgtaac gcagtagatg | 660 |
| cagctaaagc actgggtatt gatgctcgcg tgggtaacct gttctccgct gacctgttct | 720 |
| actctccgga cggcgaaatg ttcgacgtga tggaaaaata cggcattctc ggcgtggaaa | 780 |
| tggaagcggc tggtatctac ggcgtcgctg cagaatttgg cgcgaaagcc ctgaccatct | 840 |
| gcaccgtatc tgaccacatc cgcactcacg agcagaccac tgccgctgag cgtcagacta | 900 |
| ccttcaacga catgatcaaa atcgcactgg aatccgttct gctgggcgat aaagagtaag | 960 |
| tcgacctgca ggcatgcaag ctttatgctt gtaaaccgtt ttgtgaaaaa atttttaaaa | 1020 |
| taaaaaggg gacctctagg gtccccaatt aattagtaat ataatctatt aaaggtcatt | 1080 |
| caaaaggtca tccaccggat cagcttagta aagccctcgc tagattttaa tgcggatgtt | 1140 |
| gcgattactt cgccaactat tgcgataaca agaaaaagcc agcctttcat gatatatctc | 1200 |
| ccaatttgtg tagggcttat tatgcacgct taaaaataat aaaagcagac ttgacctgat | 1260 |
| agtttggctg tgagcaatta tgtgcttagt gcatctaacg cttgagttaa gccgcgccgc | 1320 |
| gaagcggcgt cggcttgaac gaattgttag acattatttg ccgactacct tggtgatctc | 1380 |
| gcctttcacg tagtggacaa attcttccaa ctgatctgcg cgccgagatg cgccgcgtgc | 1440 |
| ggctgctgga gatggcggac gcgatggata tgttctgcca agggttggtt tgcgcattca | 1500 |
| cagttctccg caagaattga ttggctccaa ttcttggagt ggtgaatccg ttagcgaggt | 1560 |
| gccgccggct tccattcagg tcgaggtggc ccggctccat gcaccgcgac gcaacgcggg | 1620 |
| gaggcagaca aggtataggg cggcgcctac aatccatgcc aacccgttcc atgtgctcgc | 1680 |
| cgaggcggca taaatcgccg tgacgatcag cggtccagtg atcgaagtta ggctggtaag | 1740 |
| agccgcgagc gatccttgaa gctgtccctg atggtcgtca tctacctgcc tggacagcat | 1800 |
| ggcctgcaac gcgggcatcc cgatgccgcc ggaagcgaga agaatcataa tggggaaggc | 1860 |
| catccagcct cgcgtcgcga acgccagcaa gacgtagccc agcgcgtcgg ccgccatgcc | 1920 |
| ggcgataatg gcctgcttct cgccgaaacg tttggtggcg ggaccagtga cgaaggcttg | 1980 |
| agcgagggcg tgcaagattc cgaataccgc aagcgacagg ccgatcatcg tcgcgctcca | 2040 |
| gcgaaagcgg tcctcgccga aaatgaccca gagcgctgcc ggcacctgtc ctacgagttg | 2100 |
| catgataaag aagacagtca taagtgcggc gacgatagtc atgccccgcg cccaccggaa | 2160 |
| ggagctgact gggttgaagg ctctcaaggg catcggtcga cgctctccct tatgcgactc | 2220 |
| ctgcattagg aagcagccca gtagtaggtt gaggccgttg agcaccgccg ccgcaaggaa | 2280 |
| tggtgcatgc aaggagatgg cgcccaacag tccccggcc acgggcctg ccaccatacc | 2340 |
| cacgccgaaa caagcgctca tgagcccgaa gtggcgagcc cgatcttccc catcggtgat | 2400 |
| gtcggcgata taggcgccag caaccgcacc tgtggcgccg gtgatgccgg ccacgatgcg | 2460 |

```
tccggcgtag aggatccaca ggacgggtgt ggtcgccatg atcgcgtagt cgatagtggc   2520
tccaagtagc gaagcgagca ggactgggcg gcggccaaag cggtcggaca gtgctccgag   2580
aacgggtgcg catagaaatt gcatcaacgc atatagcgct agcagcacgc catagtgact   2640
ggcgatgctg tcggaatgga cgatatcccg caagaggccc ggcagtaccg gcataaccaa   2700
gcctatgcct acagcatcca gggtgacggt gccgaggatg acgatgagcg cattgttaga   2760
tttcatacac ggtgcctgac tgcgttagca atttaactgt gataaactac cgcattaaag   2820
ctcatgcgga tcagtgaggg tttgcaactg cgggtcaagg atctggattt cgatcacggc   2880
acgatcatcg tgcgggaggg caagggctcc aaggatcggg ccttgatgtt acccgagagc   2940
ttggcaccca gcctgcgcga gcaggggaat tgatccggtg gatgaccttt tgaatgacct   3000
ttaatagatt atattactaa ttaattgggg accctagagg tccccttttt tattttaaaa   3060
attttttcac aaaacggttt acaagcataa agcttggcac tggccgtcgt tttacaacgt   3120
cgtgactggg aaaaccctgg cgttacccaa cttaatcgcc ttgcagcaca tccccctttc   3180
gccagctggc gtaatagcga agaggcccgc accgatcgcc cttcccaaca gttgcgcagc   3240
ctgaatggcg aatggcgcct gatgcggtat tttctcctta cgcatctgtg cggtatttca   3300
caccgcatat ggtgcactct cagtacaatc tgctctgatg ccgcatagtt aagccagccc   3360
cgacacccgc caacacccgc tgacgcgccc tgacgggctt gtctgctccc ggcatccgct   3420
tacagacaag ctgtgaccgt ctccgggagc tgcatgtgtc agaggttttc accgtcatca   3480
ccgaaacgcg cgagacgaaa gggcctcgtg atacgcctat ttttataggt taatgtcatg   3540
ataataatgg tttcttagac gtcaggtggc acttttcggg gaaatgtgcg cggaacccct   3600
atttgtttat ttttctaaat acattcaaat atgtatccgc tcatgagaca ataaccctga   3660
taaatgcttc aataatattg aaaaaggaag agtatgagta ttcaacattt ccgtgtcgcc   3720
cttattccct tttttgcggc attttgcctt cctgtttttg ctcacccaga aacgctggtg   3780
aaagtaaaag atgctgaaga tcagttgggt gcacgagtgg gttacatcga actggatctc   3840
aacagcggta agatccttga gagttttcgc cccgaagaac gttttccaat gatgagcact   3900
tttaaagttc tgctatgtgg cgcggtatta tcccgtattg acgccgggca agagcaactc   3960
ggtcgccgca tacactattc tcagaatgac ttggttgagt actcaccagt cacagaaaag   4020
catcttacgg atggcatgac agtaagagaa ttatgcagtg ctgccataac catgagtgat   4080
aacactgcgg ccaacttact tctgacaacg atcggaggac cgaaggagct aaccgctttt   4140
ttgcacaaca tgggggatca tgtaactcgc cttgatcgtt gggaaccgga gctgaatgaa   4200
gccataccaa acgacgagcg tgacaccacg atgcctgtag caatggcaac aacgttgcgc   4260
aaactattaa ctggcgaact acttactcta gcttcccggc aacaattaat agactggatg   4320
gaggcggata aagttgcagg accacttctg cgctcggccc ttccggctgg ctggtttatt   4380
gctgataaat ctggagccgg tgagcgtggg tctcgcggta tcattgcagc actggggcca   4440
gatggtaagc cctcccgtat cgtagttatc tacacgacgg ggagtcaggc aactatggat   4500
gaacgaaata gacagatcgc tgagataggt gcctcactga ttaagcattg gtaactgtca   4560
gaccaagttt actcatatat actttagatt gatttaaaac ttcattttta atttaaaagg   4620
atctaggtga agatccttt tgataatctc atgaccaaaa tcccttaacg tgagttttcg   4680
ttccactgag cgtcagaccc cgtagaaaag atcaaaggat cttcttgaga tcctttttt   4740 ctgcgcgtaa tctgctgctt gcaaacaaaa aaaccaccgc taccagcggt ggtttgtttg   4800
```

```
ccggatcaag agctaccaac tcttttccg aaggtaactg gcttcagcag agcgcagata      4860
ccaaatactg tccttctagt gtagccgtag ttaggccacc acttcaagaa ctctgtagca      4920
ccgcctacat acctcgctct gctaatcctg ttaccagtgg ctgctgccag tggcgataag      4980
tcgtgtctta ccgggttgga ctcaagacga tagttaccgg ataaggcgca gcggtcgggc      5040
tgaacggggg gttcgtgcac acagcccagc ttggagcgaa cgacctacac cgaactgaga      5100
tacctacagc gtgagctatg agaaagcgcc acgcttcccg aagggagaaa ggcggacagg      5160
tatccggtaa gcggcagggt cggaacagga gagcgcacga gggagcttcc agggggaaac      5220
gcctggtatc tttatagtcc tgtcgggttt cgccacctct gacttgagcg tcgattttg       5280 tgatgctcgt caggggggcg gagcctatgg aaaaacgcca gcaacgcggc cttttttacgg     5340 ttcctggcct tttgctggcc ttttgctcac atgttctttc ctgcgttatc ccctgattct      5400
gtggataacc gtattaccgc ctttgagtga gctgataccg ctcgccgcag ccgaacgacc      5460
gagcgcagcg agtcagtgag cgaggaagcg gaaga                                 5495
```

<210> SEQ ID NO 5
<211> LENGTH: 4189
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (243)..(1021)
<223> OTHER INFORMATION: udp
<220> FEATURE:
<221> NAME/KEY: gene
<222> LOCATION: (1037)..(1766)
<223> OTHER INFORMATION: deoD

<400> SEQUENCE: 5

```
gcgcccaata cgcaaaccgc ctctccccgc gcgttggccg attcattaat gcagctggca       60
cgacaggttt cccgactgga aagcgggcag tgagcgcaac gcaattaatg tgagttagct      120
cactcattag gcaccccagg ctttacactt tatgcttccg gctcgtatgt tgtgtggaat      180
tgtgagcgga taacaatttc acacaggaaa cagctatgac catgattacg aattcgagct      240
cggtaccatc catgtccaag tctgatgttt ttcatctcgg cctcactaaa aacgatttac      300
aaggggctac gcttgccatc gtccctggcg accgggatcg tgtggaaaag atcgccgcgc      360
tgatggataa gccggttaag ctggcatctc accgcgaatt cactacctgg cgtgcagagc      420
tggatggtaa acctgttatc gtctgctcta ccggtatcgg cggcccgtct acctctattg      480
ctgttgaaga gctggcacag ctgggcattc gcaccttcct gcgtatcggt acaacgggcg      540
ctattcagcc gcatattaat gtgggtgatg tcctggttac cacggcgtct gtccgtctgg      600
atggcgcgag cctgcacttc gcaccgctgg aattcccggc tgtcgctgat ttcgaatgta      660
cgactgcgct ggttgaagct gcgaaatcca ttggcgcgac aactcacgtt ggcgtgacag      720
cttcttctga taccttctac ccaggtcagg aacgttacga tacttactct ggtcgcgtag      780
ttcgtcactt taaggttct atggaagagt ggcaggcgat gggcgtaatg aactatgaaa      840
tggaatctgc aaccctgctg accatgtgtg caagtcaggg cctgcgtgcc ggtatggtag      900
cgggtgttat cgttaaccgc acccagcaag agatcccgaa tgctgagacg atgaaacaaa      960
ccgaaagcca tgcggtgaaa atcgtggtgg aagcggcgcg tcgtctgctg taattctctt     1020
gtcgactagc aggaggaatt cttccatggc taccccacac attaatgcag aaatgggcga     1080
tttcgctgac gtagttttga tgccaggcga cccgctgcgt gcgaagtata ttgctgaaac     1140
```

-continued

```
tttccttgaa gatgcccgtg aagtgaacaa cgttcgcggt atgctgggct tcaccggtac    1200
ttacaaaggc cgcaaaattt ccgtaatggg tcacggtatg ggtatcccgt cctgctccat    1260
ctacaccaaa gaactgatca ccgatttcgg cgtgaagaaa attatccgcg tgggttcctg    1320
tggcgcagtt ctgccgcacg taaaactgcg cgacgtcgtt atcggtatgg gtgcctgcac    1380
cgattccaaa gttaaccgca tccgttttaa agaccatgac tttgccgcta tcgctgactt    1440
cgacatggtg cgtaacgcag tagatgcagc taaagcactg ggtattgatg ctcgcgtggg    1500
taacctgttc tccgctgacc tgttctactc tccggacggc gaaatgttcg acgtgatgga    1560
aaaatacggc attctcggcg tggaaatgga agcggctggt atctacggcg tcgctgcaga    1620
atttggcgcg aaagccctga ccatctgcac cgtatctgac cacatccgca ctcacgagca    1680
gaccactgcc gctgagcgtc agactacctt caacgacatg atcaaaatcg cactggaatc    1740
cgttctgctg ggcgataaag agtaagtcga cctgcaggca tgcaagcttg gcactggccg    1800
tcgttttaca acgtcgtgac tgggaaaacc ctggcgttac ccaacttaat cgccttgcag    1860
cacatccccc tttcgccagc tggcgtaata gcgaagaggc ccgcaccgat cgcccttccc    1920
aacagttgcg cagcctgaat ggcgaatggc gcctgatgcg gtattttctc cttacgcatc    1980
tgtgcggtat ttcacaccgc atatggtgca ctctcagtac aatctgctct gatgccgcat    2040
agttaagcca gccccgacac ccgccaacac ccgctgacgc gccctgacgg gcttgtctgc    2100
tcccggcatc cgcttacaga caagctgtga ccgtctccgg gagctgcatg tgtcagaggt    2160
tttcaccgtc atcaccgaaa cgcgcgagac gaaagggcct cgtgatacgc ctatttttat    2220
aggttaatgt catgataata atggtttctt agacgtcagg tggcactttt cggggaaatg    2280
tgcgcggaac ccctatttgt ttatttttct aaatacattc aaatatgtat ccgctcatga    2340
gacaataacc ctgataaatg cttcaataat attgaaaaag gaagagtatg agtattcaac    2400
atttccgtgt cgcccttatt cccttttttg cggcattttg ccttcctgtt tttgctcacc    2460
cagaaacgct ggtgaaagta aaagatgctg aagatcagtt gggtgcacga gtgggttaca    2520
tcgaactgga tctcaacagc ggtaagatcc ttgagagttt cgccccgaa gaacgttttc    2580 caatgatgag cacttttaaa gttctgctat gtggcgcggt attatcccgt attgacgccg    2640
ggcaagagca actcggtcgc cgcatacact attctcagaa tgacttggtt gagtactcac    2700
cagtcacaga aaagcatctt acggatggca tgacagtaag agaattatgc agtgctgcca    2760
taaccatgag tgataacact gcggccaact tacttctgac aacgatcgga ggaccgaagg    2820
agctaaccgc ttttttgcac aacatggggg atcatgtaac tcgccttgat cgttgggaac    2880
cggagctgaa tgaagccata ccaaacgacg agcgtgacac cacgatgcct gtagcaatgg    2940
caacaacgtt gcgcaaacta ttaactggcg aactacttac tctagcttcc cggcaacaat    3000
taatagactg gatggaggcg gataaagttg caggaccact tctgcgctcg gcccttccgg    3060
ctggctggtt tattgctgat aaatctggag ccggtgagcg tgggtctcgc ggtatcattg    3120
cagcactggg gccagatggt aagccctccc gtatcgtagt tatctacacg acggggagtc    3180
aggcaactat ggatgaacga atagacaga tcgctgagat aggtgcctca ctgattaagc    3240
attggtaact gtcagaccaa gtttactcat atatacttta gattgattta aaacttcatt    3300
tttaatttaa aaggatctag gtgaagatcc ttttttgataa tctcatgacc aaaatccctt    3360
aacgtgagtt ttcgttccac tgagcgtcag accccgtaga aaagatcaaa ggatcttctt    3420
gagatccttt ttttctgcgc gtaatctgct gcttgcaaac aaaaaaacca ccgctaccag    3480
```

-continued

```
cggtggtttg tttgccggat caagagctac caactctttt tccgaaggta actggcttca      3540
gcagagcgca gataccaaat actgtccttc tagtgtagcc gtagttaggc caccacttca      3600
agaactctgt agcaccgcct acatacctcg ctctgctaat cctgttacca gtggctgctg      3660
ccagtggcga taagtcgtgt cttaccgggt tggactcaag acgatagtta ccggataagg      3720
cgcagcggtc gggctgaacg gggggttcgt gcacacagcc cagcttggag cgaacgacct      3780
acaccgaact gagataccta cagcgtgagc tatgagaaag cgccacgctt cccgaaggga      3840
gaaaggcgga caggtatccg gtaagcggca gggtcggaac aggagagcgc acgagggagc      3900
ttccaggggg aaacgcctgg tatctttata gtcctgtcgg gtttcgccac ctctgacttg      3960
agcgtcgatt tttgtgatgc tcgtcagggg gcggagcct atggaaaaac gccagcaacg       4020 cggcctttt acgttcctg gccttttgct ggccttttgc tcacatgttc tttcctgcgt        4080
tatcccctga ttctgtggat aaccgtatta ccgcctttga gtgagctgat accgctcgcc     4140
gcagccgaac gaccgagcgc agcgagtcag tgagcgagga agcggaaga                  4189
```

<210> SEQ ID NO 6
<211> LENGTH: 6301
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (243)..(1021)
<223> OTHER INFORMATION: udp
<220> FEATURE:
<221> NAME/KEY: gene
<222> LOCATION: (1037)..(1766)
<223> OTHER INFORMATION: deoD
<220> FEATURE:
<221> NAME/KEY: gene
<222> LOCATION: (2229)..(3628)
<223> OTHER INFORMATION: tetracycline resistance

<400> SEQUENCE: 6

```
gcgcccaata cgcaaaccgc ctctccccgc gcgttggccg attcattaat gcagctggca        60
cgacaggttt cccgactgga aagcgggcag tgagcgcaac gcaattaatg tgagttagct       120
cactcattag gcaccccagg ctttacactt tatgcttccg gctcgtatgt tgtgtggaat       180
tgtgagcgga taacaatttc acacaggaaa cagctatgac catgattacg aattcgagct       240
cggtaccatc catgtccaag tctgatgttt tcatctcgg cctcactaaa aacgatttac        300
aaggggctac gcttgccatc gtccctggcg accggatcg tgtggaaaag atcgccgcgc       360
tgatggataa gccggttaag ctggcatctc accgcgaatt cactacctgg cgtgcagagc      420
tggatggtaa acctgttatc gtctgctcta ccggtatcgg cggccgtct acctctattg       480 ctgttgaaga gctggcacag ctgggcattc gcaccttcct gcgtatcggt acaacgggcg      540
ctattcagcc gcatattaat gtgggtgatg tcctggttac cacggcgtct gtccgtctgg     600
atggcgcgag cctgcacttc gcaccgctgg aattcccggc tgtcgctgat ttcgaatgta    660
cgactgcgct ggttgaagct gcgaaatcca ttggcgcgac aactcacgtt ggcgtgacag    720
cttcttctga taccttctac ccaggtcagg aacgttacga tacttactct ggtcgcgtag    780
ttcgtcactt taaaggttct atggaagagt ggcaggcgat gggcgtaatg aactatgaaa   840
tggaatctgc aaccctgctg accatgtgtg caagtcaggg cctgcgtgcc ggtatggtag    900
cgggtgttat cgttaaccgc acccagcaag agatcccgaa tgctgagacg atgaaacaaa    960
ccgaaagcca tgcggtgaaa atcgtggtgg aagcggcgcg tcgtctgctg taattctctt    1020
```

```
gtcgactagc aggaggaatt cttccatggc tacccacac  attaatgcag aaatgggcga   1080
tttcgctgac gtagttttga tgccaggcga cccgctgcgt gcgaagtata ttgctgaaac   1140
tttccttgaa gatgcccgtg aagtgaacaa cgttcgcggt atgctgggct tcaccggtac   1200
ttacaaaggc cgcaaaattt ccgtaatggg tcacggtatg ggtatcccgt cctgctccat   1260
ctacaccaaa gaactgatca ccgatttcgg cgtgaagaaa attatccgcg tgggttcctg   1320
tggcgcagtt ctgccgcacg taaaactgcg cgacgtcgtt atcggtatgg gtgcctgcac   1380
cgattccaaa gttaaccgca tccgttttaa agaccatgac tttgccgcta tcgctgactt   1440
cgacatggtg cgtaacgcag tagatgcagc taaagcactg ggtattgatg ctcgcgtggg   1500
taacctgttc tccgctgacc tgttctactc tccggacggc gaaatgttcg acgtgatgga   1560
aaaatacggc attctcggcg tggaaatgga agcggctggt atctacggcg tcgctgcaga   1620
atttggcgcg aaagccctga ccatctgcac cgtatctgac cacatccgca ctcacgagca   1680
gaccactgcc gctgagcgtc agactacctt caacgacatg atcaaaatcg cactggaatc   1740
cgttctgctg ggcgataaag agtaagtcga cctgcaggca tgcaagcttt atgcttgtaa   1800
accgttttgt gaaaaaattt ttaaaataaa aagggggacc tctagggtcc ccaattaatt   1860
agtaatataa tctattaaag gtcattcaaa aggtcatcca ccggatcagc ttagtaaagc   1920
cctcgctaga ttttaatgcg gatgttgcga ttacttcgcc aactattgcg ataacaagaa   1980
aaagccagcc tttcatgata tatctcccaa tttgtgtagg cttattatg  cacgcttaaa   2040 aataataaaa gcagacttga cctgatagtt tggctgtgag caattatgtg cttagtgcat   2100
ctaacgcttg agttaagccg cgccgcgaag cggcgtcggc ttgaacgaat tgttagacat   2160
tatttgccga ctaccttggt gatctcgcct ttcacgtagt ggacaaattc ttccaactga   2220
tctgcgcgcc gagatgcgcc gcgtgcggct gctggagatg gcggacgcga tggatatgtt   2280
ctgccaaggg ttggtttgcg cattcacagt tctccgcaag aattgattgg ctccaattct   2340
tggagtggtg aatccgttag cgaggtgccg ccggcttcca ttcaggtcga ggtggcccgg   2400
ctccatgcac cgcgacgcaa cgcggggagg cagacaaggt atagggcggc gcctacaatc   2460
catgccaacc cgttccatgt gctcgccgag gcggcataaa tcgccgtgac gatcagcggt   2520
ccagtgatcg aagttaggct ggtaagagcc gcgagcgatc cttgaagctg tccctgatgg   2580
tcgtcatcta cctgcctgga cagcatggcc tgcaacgcgg gcatcccgat gccgccggaa   2640
gcgagaagaa tcataatggg gaaggccatc cagcctcgcg tcgcgaacgc cagcaagacg   2700
tagcccagcg cgtcggccgc catgccggcg ataatggcct gcttctcgcc gaaacgtttg   2760
gtggcgggac cagtgacgaa ggcttgagcg agggcgtgca agattccgaa taccgcaagc   2820
gacaggccga tcatcgtcgc gctccagcga aagcggtcct cgccgaaaat gacccagagc   2880
gctgccggca cctgtcctac gagttgcatg ataaagaaga cagtcataag tgcggcgacg   2940
atagtcatgc cccgcgccca ccggaaggag ctgactgggt tgaaggctct caagggcatc   3000
ggtcgacgct ctcccttatg cgactcctgc attaggaagc agcccagtag taggttgagg   3060
ccgttgagca ccgccgccgc aaggaatggt gcatgcaagg agatggcgcc caacagtccc   3120
ccggccacgg ggcctgccac catacccacg ccgaaacaag cgctcatgag cccgaagtgg   3180
cgagcccgat cttcccatc  ggtgatgtcg gcgatatagg cgccagcaac cgcacctgtg   3240
gcgccggtga tgccgccac  gatgcgtccg gcgtagagga tccacaggac gggtgtggtc   3300
gccatgatcg cgtagtcgat agtggctcca agtagcgaag cgagcaggac tgggcggcgg   3360
```

-continued

```
ccaaagcggt cggacagtgc tccgagaacg ggtgcgcata gaaattgcat caacgcatat    3420
agcgctagca gcacgccata gtgactggcg atgctgtcgg aatggacgat atcccgcaag    3480
aggcccggca gtaccggcat aaccaagcct atgcctacag catccagggt gacggtgccg    3540
aggatgacga tgagcgcatt gttagatttc atacacggtg cctgactgcg ttagcaattt    3600
aactgtgata aactaccgca ttaaagctca tgcggatcag tgagggtttg caactgcggg    3660
tcaaggatct ggatttcgat cacggcacga tcatcgtgcg ggagggcaag ggctccaagg    3720
atcgggcctt gatgttaccc gagagcttgg cacccagcct gcgcgagcag gggaattgat    3780
ccggtggatg acctttttgaa tgaccttttaa tagattatat tactaattaa ttggggaccc    3840
tagaggtccc cttttttatt ttaaaaattt tttcacaaaa cggtttacaa gcataaagct    3900
tggcactggc cgtcgtttta caacgtcgtg actgggaaaa ccctggcgtt acccaactta    3960
atcgccttgc agcacatccc cctttcgcca gctggcgtaa tagcgaagag gcccgcaccg    4020
atcgccttc ccaacagttg cgcagcctga atggcgaatg gcgcctgatg cggtattttc    4080
tccttacgca tctgtgcggt atttcacacc gcatatggtg cactctcagt acaatctgct    4140
ctgatgccgc atagttaagc cagccccgac acccgccaac accgctgac gcgccctgac    4200
gggcttgtct gctcccggca tccgcttaca gacaagctgt gaccgtctcc gggagctgca    4260
tgtgtcagag gttttcaccg tcatcaccga acgcgcgag acgaaagggc ctcgtgatac    4320
gcctattttt ataggttaat gtcatgataa taatggtttc ttagacgtca ggtggcactt    4380
ttcggggaaa tgtgcgcgga acccctattt gtttattttt ctaaatacat tcaaatatgt    4440
atccgctcat gagacaataa ccctgataaa tgcttcaata atattgaaaa aggaagagta    4500
tgagtattca acatttccgt gtcgccctta ttccctttt tgcggcattt tgccttcctg    4560
tttttgctca cccagaaacg ctggtgaaag taaaagatgc tgaagatcag ttgggtgcac    4620
gagtgggtta catcgaactg gatctcaaca gcggtaagat ccttgagagt tttcgccccg    4680
aagaacgttt tccaatgatg agcacttta aagttctgct atgtggcgcg gtattatccc    4740
gtattgacgc cgggcaagag caactcggtc gccgcataca ctattctcag aatgacttgg    4800
ttgagtactc accagtcaca gaaaagcatc ttacggatgg catgacagta agagaattat    4860
gcagtgctgc cataaccatg agtgataaca ctgcggccaa cttacttctg acaacgatcg    4920
gaggaccgaa ggagctaacc gcttttttgc acaacatggg ggatcatgta actcgccttg    4980
atcgttggga accggagctg aatgaagcca taccaaacga cgagcgtgac accacgatgc    5040
ctgtagcaat ggcaacaacg ttgcgcaaac tattaactgg cgaactactt actctagctt    5100
cccggcaaca attaatagac tggatggagg cggataaagt tgcaggacca cttctgcgct    5160
cggcccttcc ggctggctgg tttattgctg ataaatctgg agccggtgag cgtgggtctc    5220
gcggtatcat tgcagcactg gggccagatg gtaagccctc ccgtatcgta gttatctaca    5280
cgacggggag tcaggcaact atggatgaac gaaatagaca gatcgctgag ataggtgcct    5340
cactgattaa gcattggtaa ctgtcagacc aagtttactc atatatactt tagattgatt    5400
taaaacttca tttttaattt aaaaggatct aggtgaagat cctttttgat aatctcatga    5460
ccaaaatccc ttaacgtgag ttttcgttcc actgagcgtc agaccccgta gaaaagatca    5520
aaggatcttc ttgagatcct ttttttctgc gcgtaatctg ctgcttgcaa acaaaaaaac    5580
caccgctacc agcggtggtt tgtttgccgg atcaagagct accaactctt tttccgaagg    5640
taactggctt cagcagagcg cagataccaa atactgtcct tctagtgtag ccgtagttag    5700
gccaccactt caagaactct gtagcaccgc ctacatacct cgctctgcta atcctgttac    5760
```

| | |
|---|---|
| cagtggctgc tgccagtggc gataagtcgt gtcttaccgg gttggactca agacgatagt | 5820 |
| taccggataa ggcgcagcgg tcgggctgaa cgggggttc gtgcacacag cccagcttgg | 5880 |
| agcgaacgac ctacaccgaa ctgagatacc tacagcgtga gctatgagaa agcgccacgc | 5940 |
| ttcccgaagg gagaaaggcg gacaggtatc cggtaagcgg cagggtcgga acaggagagc | 6000 |
| gcacgaggga gcttccaggg ggaaacgcct ggtatcttta tagtcctgtc gggtttcgcc | 6060 |
| acctctgact tgagcgtcga tttttgtgat gctcgtcagg ggggcggagc ctatggaaaa | 6120 |
| acgccagcaa cgcggccttt ttacggttcc tggccttttg ctggcctttt gctcacatgt | 6180 |
| tctttcctgc gttatcccct gattctgtgg ataaccgtat taccgccttt gagtgagctg | 6240 |
| ataccgctcg ccgcagccga acgaccgagc gcagcgagtc agtgagcgag gaagcggaag | 6300 |
| a | 6301 |

<210> SEQ ID NO 7
<211> LENGTH: 5241
<212> TYPE: DNA
<213> ORGANISM: Artificial Sequence
<220> FEATURE:
<223> OTHER INFORMATION: plasmid
<220> FEATURE:
<221> NAME/KEY: gene
<222> LOCATION: (1312)..(2042)
<223> OTHER INFORMATION: deoD

<400> SEQUENCE: 7

| | |
|---|---|
| atcgatgcat aatgtgcctg tcaaatggac gaagcaggga ttctgcaaac cctatgctac | 60 |
| tccgtcaagc cgtcaattgt ctgattcgtt accaattatg acaacttgac ggctacatca | 120 |
| ttcacttttt cttcacaacc ggcacggaac tcgctcgggc tggccccggt gcattttta | 180 |
| aatacccgcg agaaatagag ttgatcgtca aaaccaacat tgcgaccgac ggtggcgata | 240 |
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc cgaatagcgc | 540 |
| ccttcccctt gcccggcgtt aatgatttgc ccaaacaggt cgctgaaatg cggctggtgc | 600 |
| gcttcatccg ggcgaaagaa ccccgtattg gcaaatattg acggccagtt aagccattca | 660 |
| tgccagtagg cgcgcggacg aaagtaaacc cactggtgat accattcgcg agcctccgga | 720 |
| tgacgaccgt agtgatgaat ctctcctggc gggaacagca aaatatcacc cggtcggcaa | 780 |
| acaaattctc gtccctgatt tttcaccacc ccctgaccgc gaatggtgag attgagaata | 840 |
| taacctttca ttcccagcgg tcggtcgata aaaaatcga gataaccgtt ggcctcaatc | 900 |
| ggcgttaaac ccgccaccag atgggcatta acgagtatc ccggcagcag ggatcattt | 960 |
| tgcgcttcag ccatactttt catactcccg ccattcagag aagaaaccaa ttgtccatat | 1020 |
| tgcatcagac attgccgtca ctgcgtcttt tactggctct ctcgctaac caaaccggta | 1080 |
| accccgctta ttaaaagcat tctgtaacaa agcgggacca aagccatgac aaaaacgcgt | 1140 |
| aacaaaagtg tctataatca cggcagaaaa gtccacattg attatttgca cggcgtcaca | 1200 |
| ctttgctatg ccatagcatt tttatccata agattagcgg atcctacctg acgctttta | 1260 |
| tcgcaactct ctactgtttc tccataccg ttttttggg ctagcaggag ggaattcttc | 1320 |

```
catggctacc ccacacatta atgcagaaat gggcgatttc gctgacgtag ttttgatgcc    1380
aggcgacccg ctgcgtgcga agtatattgc tgaaactttc cttgaagatg cccgtgaagt    1440
gaacaacgtt cgcggtatgc tgggcttcac cggtacttac aaaggccgca aaatttccgt    1500
aatgggtcac ggtatgggta cccgtcctg ctccatctac accaaagaac tgatcaccga    1560
tttcggcgtg aagaaaatta ccgcgtggg ttcctgtggc gcagttctgc cgcacgtaaa    1620
actgcgcgac gtcgttatcg gtatgggtgc ctgcaccgat ccaaagtta ccgcatccg     1680
ttttaaagac catgactttg ccgctatcgc tgacttcgac atggtgcgta acgcagtaga    1740
tgcagctaaa gcactgggta ttgatgctcg cgtgggtaac ctgttctccg ctgacctgtt    1800
ctactctccg gacggcgaaa tgttcgacgt gatggaaaaa tacggcattc tcggcgtgga    1860
aatgaagcg gctggtatct acggcgtcgc tgcagaattt ggcgcgaaag ccctgaccat    1920
ctgcaccgta tctgaccaca tccgcactca cgagcagacc actgccgctg agcgtcagac    1980
taccttcaac gacatgatca aaatcgcact ggaatccgtt ctgctgggcg ataaagagta    2040
agtcgacctg caggcatgca agcttggctg ttttggcgga tgagagaaga ttttcagcct    2100
gatacagatt aaatcagaac gcagaagcgg tctgataaaa cagaatttgc ctggcggcag    2160
tagcgcggtg gtcccacctg accccatgcc gaactcagaa gtgaaacgcc gtagcgccga    2220
tggtagtgtg gggtctcccc atgcgagagt agggaactgc caggcatcaa ataaaacgaa    2280
aggctcagtc gaaagactgg gcctttcgtt ttatctgttg tttgtcggtg aacgctctcc    2340
tgagtaggac aaatccgccg ggagcggatt tgaacgttgc gaagcaacgg cccggagggt    2400
ggcgggcagg acgcccgcca taaactgcca ggcatcaaat taagcagaag gccatcctga    2460
cggatggcct ttttgcgttt ctacaaactc ttttgtttat ttttctaaat acattcaaat    2520
atgtatccgc tcatgagaca ataaccctga taatgcttc aataatattg aaaaggaag    2580
agtatgagta ttcaacattt ccgtgtcgcc cttattccct tttttgcggc attttgcctt    2640
cctgttttg ctcacccaga aacgctggtg aaagtaaaag atgctgaaga tcagttgggt    2700
gcacgagtgg gttacatcga actggatctc aacagcggta agatccttga gttttcgc     2760
cccgaagaac gttttccaat gatgagcact tttaaagttc tgctatgtgg cgcggtatta    2820
tcccgtgttg acgccgggca agagcaactc ggtcgccgca tacactattc tcagaatgac    2880
ttggttgagt actcaccagt cacagaaaag catcttacgg atggcatgac agtaagagaa    2940
ttatgcagtg ctgccataac catgagtgat aacactgcgg ccaacttact tctgacaacg    3000
atcggaggac cgaaggagct aaccgctttt ttgcacaaca tgggggatca tgtaactcgc    3060
cttgatcgtt gggaaccgga gctgaatgaa gccataccaa acgacgagcg tgacaccacg    3120
atgcctgtag caatggcaac aacgttgcgc aaactattaa ctggcgaact acttactcta    3180
gcttcccggc aacaattaat agactggatg gaggcggata agttgcagg accacttctg    3240
cgctcggccc ttccggctgg ctggtttatt gctgataaat ctggagccgg tgagcgtggg    3300
tctcgcggta tcattgcagc actggggcca gatggtaagc cctcccgtat cgtagttatc    3360
tacacgacgg ggagtcaggc aactatggat gaacgaaata gacagatcgc tgagataggt    3420
gcctcactga ttaagcattg gtaactgtca gaccaagttt actcatatat actttagatt    3480
gatttacgcg ccctgtagcg cgcattaag cgcggcgggt gtggtggtta cgcgcagcgt    3540
gaccgctaca cttgccagcg ccctagcgcc cgctcctttc gctttcttcc cttcctttct    3600
cgccacgttc gccggctttc cccgtcaagc tctaaatcgg gggctccctt tagggttccg    3660
atttagtgct ttacggcacc tcgaccccaa aaaacttgat ttgggtgatg gttcacgtag    3720
```

-continued

```
tgggccatcg ccctgataga cggttttttcg ccctttgacg ttggagtcca cgttctttaa      3780
tagtggactc ttgttccaaa cttgaacaac actcaaccct atctcgggct attcttttga      3840
tttataaggg attttgccga tttcggccta ttggttaaaa aatgagctga tttaacaaaa      3900
atttaacgcg aattttaaca aaatattaac gtttacaatt taaaaggatc taggtgaaga      3960
tcctttttga taatctcatg accaaaatcc cttaacgtga gttttcgttc cactgagcgt      4020
cagaccccgt agaaaagatc aaaggatctt cttgagatcc ttttttttctg cgcgtaatct      4080
gctgcttgca acaaaaaaa ccaccgctac cagcggtggt ttgtttgccg gatcaagagc      4140
taccaactct tttccgaag gtaactggct tcagcagagc gcagatacca aatactgtcc      4200
ttctagtgta gccgtagtta ggccaccact tcaagaactc tgtagcaccg cctacatacc      4260
tcgctctgct aatcctgtta ccagtggctg ctgccagtgg cgataagtcg tgtcttaccg      4320
ggttggactc aagacgatag ttaccggata aggcgcagcg tcgggctga acggggggtt      4380
cgtgcacaca gcccagcttg gagcgaacga cctacaccga actgagatac ctacagcgtg      4440
agctatgaga aagcgccacg cttcccgaag ggagaaaggc ggacaggtat ccggtaagcg      4500
gcagggtcgg aacaggagag cgcacgaggg agcttccagg gggaaacgcc tggtatcttt      4560
atagtcctgt cgggtttcgc cacctctgac ttgagcgtcg attttttgtga tgctcgtcag      4620
ggggggcggag cctatggaaa aacgccagca acgcggcctt tttacggttc ctggccttt       4680
gctggccttt tgctcacatg ttctttcctg cgttatcccc tgattctgtg gataaccgta      4740
ttaccgcctt tgagtgagct gataccgctc gccgcagccg aacgaccgag cgcagcgagt      4800
cagtgagcga ggaagcggaa gagcgcctga tgcggtattt tctccttacg catctgtgcg      4860
gtatttcaca ccgcataggg tcatggctgc gccccgacac ccgccaacac ccgctgacgc      4920
gccctgacgg gcttgtctgc tcccggcatc cgcttacaga caagctgtga ccgtctccgg      4980
gagctgcatg tgtcagaggt tttcaccgtc atcaccgaaa cgcgcgaggc agcaaggaga      5040
tggcgcccaa cagtccccg gccacggggc ctgccaccat acccacgccg aaacaagcgc      5100
tcatgagccc gaagtggcga gcccgatctt ccccatcggt gatgtcggcg atataggcgc      5160
cagcaaccgc acctgtggcg ccggtgatgc cggccacgat gcgtccggcg tagaggatct      5220
gctcatgttt gacagcttat c                                                5241
```

<210> SEQ ID NO 8
<211> LENGTH: 5822
<212> TYPE: DNA
<213> ORGANISM: Artificial Sequence
<220> FEATURE:
<223> OTHER INFORMATION: pGM716 with deletion of HpaI fragment

<400> SEQUENCE: 8

```
gcgcccaata cgcaaaccgc ctctccccgc gcgttggccg attcattaat gcagctggca       60
cgacaggttt cccgactgga aagcgggcag tgagcgcaac gcaattaatg tgagttagct      120
cactcattag gcaccccagg ctttacactt tatgcttccg gctcgtatgt tgtgtggaat      180
tgtgagcgga taacaatttc acacaggaaa cagctatgac catgattacg aattcgagct      240
cggtaccatc catgtccaag tctgatgttt ttcatctcgg cctcactaaa aacgatttac      300
aagggggctac gcttgccatc gtccctggcg accggatcg tgtggaaaag atcgccgcgc      360
tgatggataa gccggttaag ctggcatctc accgcgaatt cactacctgg cgtgcagagc      420
tggatggtaa acctgttatc gtctgctcta ccggtatcgg cggcccgtct acctctattg      480
```

-continued

```
ctgttgaaga gctggcacag ctgggcattc gcaccttcct gcgtatcggt acaacgggcg      540
ctattcagcc gcatattaat gtgggtgatg tcctggttac cacggcgtct gtccgtctgg      600
atggcgcgag cctgcacttc gcaccgctgg aattcccggc tgtcgctgat ttcgaatgta      660
cgactgcgct ggttgaagct gcgaaatcca ttggcgcgac aactcacgtt ggcgtgacag      720
cttcttctga taccttctac ccaggtcagg aacgttacga tacttactct ggtcgcgtag      780
ttcgtcactt taaaggttct atggaagagt ggcaggcgat gggcgtaatg aactatgaaa      840
tggaatctgc aaccctgctg accatgtgtg caagtcaggg cctgcgtgcc ggtatggtag      900
cgggtgttat cgttaaccgc atccgtttta aagaccatga ctttgccgct atcgctgact      960
tcgacatggt gcgtaacgca gtagatgcag ctaaagcact gggtattgat gctcgcgtgg     1020
gtaacctgtt ctccgctgac ctgttctact ctccggacgc gaaatgttc gacgtgatgg     1080
aaaaatacgg cattctcggc gtggaaatgg aagcggctgg tatctacggc gtcgctgcag     1140
aatttggcgc gaaagccctg accatctgca ccgtatctga ccacatccgc actcacgagc     1200
agaccactgc cgctgagcgt cagactacct tcaacgacat gatcaaaatc gcactggaat     1260
ccgttctgct gggcgataaa gagtaagtcg acctgcaggc atgcaagctt tatgcttgta     1320
aaccgttttg tgaaaaaatt tttaaaataa aaagggggac ctctagggtc cccaattaat     1380
tagtaatata atctattaaa ggtcattcaa aaggtcatcc accggatcag cttagtaaag     1440
ccctcgctag attttaatgc ggatgttgcg attacttcgc caactattgc gataacaaga     1500
aaaagccagc cttcatgat atatctccca atttgtgtag ggcttattat gcacgcttaa     1560
aaataataaa agcagacttg acctgatagt ttggctgtga gcaattatgt gcttagtgca     1620
tctaacgctt gagttaagcc gcgccgcgaa gcggcgtcgg cttgaacgaa ttgttagaca     1680
ttatttgccg actaccttgg tgatctcgcc tttcacgtag tggacaaatt cttccaactg     1740
atctgcgcgc cgagatgcgc cgcgtgcggc tgctggagat ggcggacgcg atggatatgt     1800
tctgccaagg gttggtttgc gcattcacag ttctccgcaa gaattgattg ctccaattc      1860
ttggagtggt gaatccgtta gcgaggtgcc gccggcttcc attcaggtcg aggtggcccg     1920
gctccatgca ccgcgacgca acgcggggag gcagacaagg tatagggcgg cgcctacaat     1980
ccatgccaac ccgttccatg tgctcgccga ggcggcataa atcgccgtga cgatcagcgg     2040
tccagtgatc gaagttaggc tggtaagagc cgcgagcgat ccttgaagct gtccctgatg     2100
gtcgtcatct acctgcctgg acagcatggc ctgcaacgcg gcatcccga tgccgccgga      2160
agcgagaaga atcataatgg ggaaggccat ccagcctcgc gtcgcgaacg ccagcaagac     2220
gtagcccagc gcgtcggccg ccatgccggc gataatggcc tgcttctcgc cgaaacgttt     2280
ggtggcggga ccagtgacga aggcttgagc gagggcgtgc aagattccga ataccgcaag     2340
cgacaggccg atcatcgtcg cgctccagcg aaagcggtcc tcgccgaaaa tgacccagag     2400
cgctgccggc acctgtccta cgagttgcat gataaagaag acagtcataa gtgcggcgac     2460
gatagtcatg ccccgcgccc accggaagga gctgactggg ttgaaggctc tcaagggcat     2520
cggtcgacgc tctcccttat gcgactcctg cattaggaag cagcccagta gtaggttgag     2580
gccgttgagc accgccgccg caaggaatgg tgcatgcaag agatggcgc caacagtcc      2640
cccgccacg gggcctgcca ccatacccac gccgaaacaa gcgctcatga gcccgaagtg     2700
gcgagcccga tcttccccat cggtgatgtc ggcgatatag gcgccagcaa ccgcacctgt     2760
ggcgccggtg atgccggcca cgatgcgtcc ggcgtagagg atccacagga cgggtgtggt     2820
cgccatgatc gcgtagtcga tagtggctcc aagtagcgaa gcgagcagga ctgggcggcg     2880
```

```
gccaaagcgg tcggacagtg ctccgagaac gggtgcgcat agaaattgca tcaacgcata   2940
tagcgctagc agcacgccat agtgactggc gatgctgtcg gaatggacga tatcccgcaa   3000
gaggcccgga agtaccggca taaccaagcc tatgcctaca gcatccaggg tgacggtgcc   3060
gaggatgacg atgagcgcat tgttagattt catacacggt gcctgactgc gttagcaatt   3120
taactgtgat aaactaccgc attaaagctc atgcggatca gtgagggttt gcaactgcgg   3180
gtcaaggatc tggatttcga tcacggcacg atcatcgtgc gggagggcaa gggctccaag   3240
gatcgggcct tgatgttacc cgagagcttg cacccagcc tgcgcgagca ggggaattga   3300
tccggtggat gaccttttga atgaccttta atagattata ttactaatta attggggacc   3360
ctagaggtcc cctttttttat tttaaaaatt ttttcacaaa acggtttaca agcataaagc   3420
ttggcactgg ccgtcgtttt acaacgtcgt gactgggaaa accctggcgt tacccaactt   3480
aatcgccttg cagcacatcc ccctttcgcc agctggcgta atagcgaaga ggcccgcacc   3540
gatcgccctt cccaacagtt gcgcagcctg aatggcgaat ggcgcctgat gcggtatttt   3600
ctccttacgc atctgtgcgg tatttcacac cgcatatggt gcactctcag tacaatctgc   3660
tctgatgccg catagttaag ccagccccga cacccgccaa cacccgctga cgcgccctga   3720
cgggcttgtc tgctcccggc atccgcttac agacaagctg tgaccgtctc cgggagctgc   3780
atgtgtcaga ggttttcacc gtcatcaccg aaacgcgcga cgaaaggg cctcgtgata   3840 cgcctatttt tataggttaa tgtcatgata taatggtttc ttagacgtc aggtggcact   3900 tttcggggaa atgtgcgcgg aacccctatt tgtttatttt tctaaataca ttcaaatatg   3960
tatccgctca tgagacaata accctgataa atgcttcaat aatattgaaa aaggaagagt   4020
atgagtattc aacatttccg tgtcgccctt attcccttt ttgcggcatt ttgccttcct   4080 gttttgctc acccagaaac gctggtgaaa gtaaagatg ctgaagatca gttgggtgca   4140
cgagtgggtt acatcgaact ggatctcaac agcggtaaga tccttgagag ttttcgcccc   4200
gaagaacgtt ttccaatgat gagcactttt aaagttctgc tatgtggcgc ggtattatcc   4260
cgtattgacg ccgggcaaga gcaactcggt cgccgcatac actattctca gaatgacttg   4320
gttgagtact caccagtcac agaaaagcat cttacggatg gcatgacagt aagagaatta   4380
tgcagtgctg ccataaccat gagtgataac actgcggcca acttacttct gacaacgatc   4440
ggaggaccga aggagctaac cgcttttttg cacaacatgg gggatcatgt aactcgcctt   4500
gatcgttggg aaccggagct gaatgaagcc ataccaaacg acgagcgtga ccacacgatg   4560
cctgtagcaa tggcaacaac gttgcgcaaa ctattaactg gcgaactact tactctagct   4620
tcccggcaac aattaataga ctggatggag gcggataaag ttgcaggacc acttctgcgc   4680
tcggcccttc cggctggctg gtttattgct gataaatctg gagccggtga gcgtgggtct   4740
cgcggtatca ttgcagcact ggggccagat ggtaagccct cccgtatcgt agttatctac   4800
acgacgggga gtcaggcaac tatggatgaa cgaaatagac agatcgctga taggtgcc   4860 tcactgatta agcattggta actgtcagac caagtttact catatatact ttagattgat   4920
ttaaaacttc attttaattt aaaaggatc taggtgaaga tcctttttga taatctcatg   4980
accaaaatcc cttaacgtga gttttcgttc cactgagcgt cagacccgt agaaaagatc   5040 aaaggatctt cttgagatcc tttttttctg cgcgtaatct gctgcttgca aacaaaaaaa   5100
ccaccgctac cagcggtggt ttgtttgccg gatcaagagc taccaactct ttttccgaag   5160
gtaactggct tcagcagagc gcagatacca atactgtcc ttctagtgta gccgtagtta   5220
```

```
ggccaccact tcaagaactc tgtagcaccg cctacatacc tcgctctgct aatcctgtta    5280
ccagtggctg ctgccagtgg cgataagtcg tgtcttaccg ggttggactc aagacgatag    5340
ttaccggata aggcgcagcg gtcgggctga acgggggggtt cgtgcacaca gcccagcttg    5400
gagcgaacga cctacaccga actgagatac ctacagcgtg agctatgaga aagcgccacg    5460
cttcccgaag ggagaaaggc ggacaggtat ccggtaagcg gcagggtcgg aacaggagag    5520
cgcacgaggg agcttccagg gggaaacgcc tggtatcttt atagtcctgt cgggtttcgc    5580
cacctctgac ttgagcgtcg attttttgtga tgctcgtcag ggggcggag cctatggaaa    5640 aacgccagca acgcggcctt tttacggttc ctggccttt gctggccttt tgctcacatg    5700
ttctttcctg cgttatcccc tgattctgtg ataaccgta ttaccgcctt tgagtgagct    5760
gataccgctc gccgcagccg aacgaccgag cgcagcgagt cagtgagcga ggaagcggaa    5820
ga                                                                    5822
```

<210> SEQ ID NO 9
<211> LENGTH: 6269
<212> TYPE: DNA
<213> ORGANISM: Artificial Sequence
<220> FEATURE:
<223> OTHER INFORMATION: udp and deoD cloned in pUC18 so to create a
      fusion between the two proteins

<400> SEQUENCE: 9

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg aattcgagct    240
cggtaccatc catgtccaag tctgatgttt ttcatctcgg cctcactaaa aacgatttac    300
aaggggctac gcttgccatc gtccctggcg acccggatcg tgtggaaaag atcgccgcgc    360
tgatggataa gccggttaag ctggcatctc accgcgaatt cactacctgg cgtgcagagc    420
tggatggtaa acctgttatc gtctgctcta ccggtatcgg cggcccgtct acctctattg    480
ctgttgaaga gctggcacag ctgggcattc gcaccttcct gcgtatcggt acaacgggcg    540
ctattcagcc gcatattaat gtgggtgatg tcctggttac cacggcgtct gtccgtctgg    600
atggcgcgag cctgcacttc gcaccgctgg aattcccggc tgtcgctgat ttcgaatgta    660
cgactgcgct ggttgaagct gcgaaatcca ttggcgcgac aactcacgtt ggcgtgacag    720
cttcttctga taccttctac ccaggtcagg aacgttacga tacttactct ggtcgcgtag    780
ttcgtcactt taaaggttct atggaagagt ggcaggcgat gggcgtaatg aactatgaaa    840
tggaatctgc aaccctgctg accatgtgtg caagtcaggg cctgcgtgcc ggtatggtag    900
cgggtgttat cgttaaccgc acccagcaag agatcccgaa tgctgagacg atgaaacaaa    960
ccgaaagcca tgcggtgaaa atcgtggtgg aagcggcgcg tcgtctgctg tccatggcta   1020
ccccacacat taatgcagaa atgggcgatt cgctgacgt agtttttgatg ccaggcgacc   1080 cgctgcgtgc gaagtatatt gctgaaactt tccttgaaga tgcccgtgaa gtgaacaacg   1140
ttcgcggtat gctgggcttc accggtactt acaaaggccg caaaatttcc gtaatgggtc   1200
acggtatggg tatcccgtcc tgctccatct acaccaaaga actgatcacc gatttcggcg   1260
tgaagaaaat tatccgcgtg ggttctgtg gcgcagttct gccgcacgta aaactgcgcg   1320
acgtcgttat cggtatgggt gcctgcaccg attccaaagt taaccgcatc cgttttaaag   1380
```

```
accatgactt tgccgctatc gctgacttcg acatggtgcg taacgcagta gatgcagcta    1440
aagcactggg tattgatgct cgcgtgggta acctgttctc cgctgacctg ttctactctc    1500
cggacggcga aatgttcgac gtgatggaaa aatacggcat tctcggcgtg aaatggaag     1560 cggctggtat ctacggcgtc gctgcagaat ttggcgcgaa agccctgacc atctgcaccg    1620
tatctgacca catccgcact cacgagcaga ccactgccgc tgagcgtcag actaccttca    1680
acgacatgat caaaatcgca ctggaatccg ttctgctggg cgataaagag taagtcgacc    1740
tgcaggcatg caagctttat gcttgtaaac cgttttgtga aaaattttt aaaataaaaa     1800 aggggacctc tagggtcccc aattaattag taatataatc tattaaaggt cattcaaaag    1860
gtcatccacc ggatcagctt agtaaagccc tcgctagatt ttaatgcgga tgttgcgatt    1920
acttcgccaa ctattgcgat aacaagaaaa agccagcctt tcatgatata tctcccaatt    1980
tgtgtagggc ttattatgca cgcttaaaaa taataaaagc agacttgacc tgatagtttg    2040
gctgtgagca attatgtgct tagtgcatct aacgcttgag ttaagccgcg ccgcgaagcg    2100
gcgtcggctt gaacgaattg ttagacatta tttgccgact accttggtga tctcgccttt    2160
cacgtagtgg acaaattctt ccaactgatc tgcgcgccga gatgcgccgc gtgcggctgc    2220
tggagatggc ggacgcgatg gatatgttct gccaagggtt ggtttgcgca ttcacagttc    2280
tccgcaagaa ttgattggct ccaattcttg gagtggtgaa tccgttagcg aggtgccgcc    2340
ggcttccatt caggtcgagg tggcccggct ccatgcaccg cgacgcaacg cggggaggca    2400
gacaaggtat agggcggcgc ctacaatcca tgccaacccg ttccatgtgc tcgccgaggc    2460
ggcataaatc gccgtgacga tcagcggtcc agtgatcgaa gttaggctgg taagagccgc    2520
gagcgatcct tgaagctgtc cctgatggtc gtcatctacc tgcctggaca gcatggcctg    2580
caacgcgggc atcccgatgc cgccggaagc gagaagaatc ataatgggga aggccatcca    2640
gcctcgcgtc gcgaacgcca gcaagacgta gcccagcgcg tcggccgcca tgccggcgat    2700
aatggcctgc ttctcgccga aacgtttggt ggcgggacca gtgacgaagg cttgagcgag    2760
ggcgtgcaag attccgaata ccgcaagcga caggccgatc atcgtcgcgc tccagcgaaa    2820
gcggtcctcg ccgaaaatga cccagagcgc tgccggcacc tgtcctacga gttgcatgat    2880
aaagaagaca gtcataagtg cggcgacgat agtcatgccc cgcgcccacc ggaaggagct    2940
gactgggttg aaggctctca agggcatcgg tcgacgctct cccttatgcg actcctgcat    3000
taggaagcag cccagtagta ggttgaggcc gttgagcacc gccgccgcaa ggaatggtgc    3060
atgcaaggag atgcgcccca acagtccccc ggccacgggg cctgccacca tacccacgcc    3120
gaaacaagcg ctcatgagcc cgaagtggcg agcccgatct tccccatcgg tgatgtcggc    3180
gatataggcg ccagcaaccg cacctgtggc gccggtgatg ccggccacga tgcgtccggc    3240
gtagaggatc cacaggacgg tgtggtcgc catgatcgcg tagtcgatag tggctccaag    3300
tagcgaagcg agcaggactg gcggcggcc aaagcggtcg acagtgctc cgagaacggg     3360 tgcgcataga aattgcatca acgcatatag cgctagcagc acgccatagt gactggcgat    3420
gctgtcggaa tggacgatat cccgcaagag gcccggcagt accggcataa ccaagcctat    3480
gcctacagca tccagggtga cggtgccgag gatgacgatg agcgcattgt tagatttcat    3540
acacggtgcc tgactgcgtt agcaatttaa ctgtgataaa ctaccgcatt aaagctcatg    3600
cggatcagtg agggtttgca actgcgggtc aaggatctgg atttcgatca cggcacgatc    3660
atcgtgcggg agggcaaggg ctccaaggat cgggccttga tgttacccga gagcttggca    3720
cccagcctgc gcgagcaggg gaattgatcc ggtggatgac cttttgaatg accttttaata   3780
```

-continued

```
gattatatta ctaattaatt ggggaccccta gaggtcccct ttttattttt aaaaattttt    3840
tcacaaaacg gtttacaagc ataaagcttg gcactggccg tcgttttaca acgtcgtgac    3900
tgggaaaacc ctggcgttac ccaacttaat cgccttgcag cacatccccc tttcgccagc    3960
tggcgtaata gcgaagaggc ccgcaccgat cgcccttccc aacagttgcg cagcctgaat    4020
ggcgaatggc gcctgatgcg gtattttctc cttacgcatc tgtgcggtat ttcacaccgc    4080
atatggtgca ctctcagtac aatctgctct gatgccgcat agttaagcca gccccgacac    4140
ccgccaacac ccgctgacgc gccctgacgg gcttgtctgc tcccggcatc cgcttacaga    4200
caagctgtga ccgtctccgg gagctgcatg tgtcagaggt tttcaccgtc atcaccgaaa    4260
cgcgcgagac gaaagggcct cgtgatacgc ctatttttat aggttaatgt catgataata    4320
atggtttctt agacgtcagg tggcactttt cggggaaatg tgcgcggaac cctatttgt     4380 ttatttttct aaatacattc aaatatgtat ccgctcatga caataaccc tgataaatg      4440 cttcaataat attgaaaaag gaagagtatg agtattcaac atttccgtgt cgcccttatt    4500
cccttttttg cggcattttg ccttcctgtt tttgctcacc cagaaacgct ggtgaaagta    4560
aaagatgctg aagatcagtt gggtgcacga gtgggttaca tcgaactgga tctcaacagc    4620
ggtaagatcc ttgagagttt tcgccccgaa gaacgttttc caatgatgag cacttttaaa    4680
gttctgctat gtggcgcggt attatcccgt attgacgccg ggcaagagca actcggtcgc    4740
cgcatacact attctcagaa tgacttggtt gagtactcac cagtcacaga aaagcatctt    4800
acggatggca tgacagtaag agaattatgc agtgctgcca taaccatgag tgataacact    4860
gcggccaact tacttctgac aacgatcgga ggaccgaagg agctaaccgc ttttttgcac    4920
aacatggggg atcatgtaac tcgccttgat cgttgggaac cggagctgaa tgaagccata    4980
ccaaacgacg agcgtgacac cacgatgcct gtagcaatgg caacaacgtt gcgcaaacta    5040
ttaactggcg aactacttac tctagcttcc cggcaacaat taatagactg gatggaggcg    5100
gataaagttg caggaccact tctgcgctcg gcccttccgg ctggctggtt tattgctgat    5160
aaatctggag ccggtgagcg tgggtctcgc ggtatcattg cagcactggg gccagatggt    5220
aagccctccc gtatcgtagt tatctacacg acggggagtc aggcaactat ggatgaacga    5280
aatagacaga tcgctgagat aggtgcctca ctgattaagc attggtaact gtcagaccaa    5340
gtttactcat atatacttta gattgattta aaacttcatt tttaatttaa aaggatctag    5400
gtgaagatcc tttttgataa tctcatgacc aaaatccctt aacgtgagtt ttcgttccac    5460
tgagcgtcag accccgtaga aaagatcaaa ggatcttctt gagatccttt ttttctgcgc    5520
gtaatctgct gcttgcaaac aaaaaaacca ccgctaccag cggtggtttg tttgccggat    5580
caagagctac caactctttt tccgaaggta actggcttca gcagagcgca gataccaaat    5640
actgtccttc tagtgtagcc gtagttaggc caccacttca agaactctgt agcaccgcct    5700
acatacctcg ctctgctaat cctgttacca gtggctgctg ccagtggcga taagtcgtgt    5760
cttaccgggt tggactcaag acgatagtta ccggataagg cgcagcggtc gggctgaacg    5820
gggggttcgt gcacacagcc cagcttggag cgaacgacct acaccgaact gagataccta    5880
cagcgtgagc tatgagaaag cgccacgctt cccgaaggga gaaaggcgga caggtatccg    5940
gtaagcggca gggtcggaac aggagagcgc acgagggagc ttccaggggg aaacgcctgg    6000
tatctttata gtcctgtcgg gtttcgccac ctctgacttg agcgtcgatt tttgtgatgc    6060
tcgtcagggg ggcggagcct atggaaaaac gccagcaacg cggccttttt acggttcctg    6120
```

-continued

```
gccttttgct ggccttttgc tcacatgttc tttcctgcgt tatccctga ttctgtggat      6180 aaccgtatta ccgcctttga gtgagctgat accgctcgcc gcagccgaac gaccgagcgc      6240
agcgagtcag tgagcgagga agcggaaga                                         6269
```

<210> SEQ ID NO 10
<211> LENGTH: 6299
<212> TYPE: DNA
<213> ORGANISM: Artificial Sequence
<220> FEATURE:
<223> OTHER INFORMATION: udp and deoD cloned in pUC18 so to create a
      fusion between the two proteins bonded to each other via an aa
      linker

<400> SEQUENCE: 10

```
gcgcccaata cgcaaaccgc ctctccccgc gcgttggccg attcattaat gcagctggca        60
cgacaggttt cccgactgga aagcgggcag tgagcgcaac gcaattaatg tgagttagct       120
cactcattag gcaccccagg ctttacactt tatgcttccg gctcgtatgt tgtgtggaat       180
tgtgagcgga taacaatttc acacaggaaa cagctatgac catgattacg aattcgagct       240
cggtaccatc catgtccaag tctgatgttt tcatctcgg cctcactaaa aacgatttac        300
aaggggctac gcttgccatc gtccctggcg acccggatcg tgtggaaaag atcgccgcgc       360
tgatggataa gccggttaag ctggcatctc accgcgaatt cactacctgg cgtgcagagc       420
tggatggtaa acctgttatc gtctgctcta ccggtatcgg cggcccgtct acctctattg       480
ctgttgaaga gctggcacag ctgggcattc gcaccttcct gcgtatcggt acaacgggcg       540
ctattcagcc gcatattaat gtgggtgatg tcctggttac cacggcgtct gtccgtctgg       600
atggcgcgag cctgcacttc gcaccgctgg aattcccggc tgtcgctgat ttcgaatgta       660
cgactgcgct ggttgaagct gcgaaatcca ttggcgcgac aactcacgtt ggcgtgacag       720
cttcttctga taccttctac ccaggtcagg aacgttacga tacttactct ggtcgcgtag       780
ttcgtcactt taaaggttct atggaagagt ggcaggcgat gggcgtaatg aactatgaaa       840
tggaatctgc aaccctgctg accatgtgtg caagtcaggg cctgcgtgcc ggtatggtag       900
cgggtgttat cgttaaccgc acccagcaag agatcccgaa tgctgagacg atgaaacaaa       960
ccgaaagcca tgcggtgaaa atcgtggtgg aagcggcgcg tcgtctgctg tccatgggcg      1020
gtggcagccc gggcattctg gccatggcta ccccacacat taatgcagaa atgggcgatt      1080 cgctgacgt agttttgatg ccaggcgacc cgctgcgtgc gaagtatatt gctgaaactt      1140
tccttgaaga tgcccgtgaa gtgaacaacg ttcgcggtat gctgggcttc accggtactt      1200
acaaaggccg caaaattcc gtaatgggtc acggtatggg tatcccgtcc tgctccatct      1260
acaccaaaga actgatcacc gatttcggcg tgaagaaaat tatccgcgtg ggttcctgtg      1320
gcgcagttct gccgcacgta aaactgcgcg acgtcgttat cggtatgggt gcctgcaccg      1380
attccaaagt taaccgcatc cgtttttaaag accatgactt tgccgctatc gctgacttcg      1440
acatggtgcg taacgcagta gatgcagcta agcactggg tattgatgct cgcgtgggta      1500
acctgttctc cgctgacctg ttctactctc cggacggcga aatgttcgac gtgatggaaa      1560
aatacggcat tctcggcgtg gaaatggaag cggctggtat ctacggcgtc gctgcagaat      1620
ttggcgcgaa agccctgacc atctgcaccg tatctgacca catccgcact cacgagcaga      1680
ccactgccgc tgagcgtcag actaccttca cgacatgat caaaatcgca ctggaatccg      1740
ttctgctggg cgataaagag taagtcgacc tgcaggcatg caagctttat gcttgtaaac      1800
cgttttgtga aaaaattttt aaaataaaaa agggggacctc tagggtcccc aattaattag      1860
```

```
taatataatc tattaaaggt cattcaaaag gtcatccacc ggatcagctt agtaaagccc   1920
tcgctagatt ttaatgcgga tgttgcgatt acttcgccaa ctattgcgat aacaagaaaa   1980
agccagcctt tcatgatata tctcccaatt tgtgtagggc ttattatgca cgcttaaaaa   2040
taataaaagc agacttgacc tgatagtttg gctgtgagca attatgtgct tagtgcatct   2100
aacgcttgag ttaagccgcg ccgcgaagcg cgtcggctt gaacgaattg ttagacatta    2160
tttgccgact accttggtga tctcgccttt cacgtagtgg acaaattctt ccaactgatc   2220
tgcgcgccga gatgcgccgc gtgcggctgc tggagatggc ggacgcgatg gatatgttct   2280
gccaagggtt ggtttgcgca ttcacagttc tccgcaagaa ttgattggct ccaattcttg   2340
gagtggtgaa tccgttagcg aggtgccgcc ggcttccatt caggtcgagg tggcccggct   2400
ccatgcaccg cgacgcaacg cggggaggca gacaaggtat agggcggcgc ctacaatcca   2460
tgccaacccg ttccatgtgc tcgccgaggc ggcataaatc gccgtgacga tcagcggtcc   2520
agtgatcgaa gttaggctgg taagagccgc gagcgatcct tgaagctgtc cctgatggtc   2580
gtcatctacc tgcctggaca gcatggcctg caacgcgggc atcccgatgc cgccggaagc   2640
gagaagaatc ataatgggga aggccatcca gcctcgcgtc gcgaacgcca gcaagacgta   2700
gcccagcgcg tcggccgcca tgccggcgat aatggcctgc ttctcgccga acgtttggt    2760 ggcgggacca gtgacgaagg cttgagcgag ggcgtgcaag attccgaata ccgcaagcga   2820
caggccgatc atcgtcgcgc tccagcgaaa gcggtcctcg ccgaaaatga cccagagcgc   2880
tgccggcacc tgtcctacga gttgcatgat aaagaagaca gtcataagtg cggcgacgat   2940
agtcatgccc cgcgcccacc ggaaggagct gactgggttg aaggctctca agggcatcgg   3000
tcgacgctct cccttatgcg actcctgcat taggaagcag cccagtagta ggttgaggcc   3060
gttgagcacc gccgccgcaa ggaatggtgc atgcaaggag atggcgccca acagtccccc   3120
ggccacgggg cctgccacca tacccacgcc gaaacaagcg ctcatgagcc cgaagtggcg   3180
agcccgatct tccccatcgg tgatgtcggc gatataggcg ccagcaaccg cacctgtggc   3240
gccggtgatg ccgccacga tgcgtccggc gtagaggatc cacaggacgg gtgtggtcgc    3300
catgatcgcg tagtcgatag tggctccaag tagcgaagcg agcaggactg ggcggcggcc   3360
aaagcggtcg acagtgctc cgagaacggg tgcgcataga aattgcatca acgcatatag    3420
cgctagcagc acgccatagt gactggcgat gctgtcggaa tggacgatat cccgcaagag   3480
gcccggcagt accggcataa ccaagcctat gcctacagca tccagggtga cggtgccgag   3540
gatgacgatg agcgcattgt tagatttcat acacggtgcc tgactgcgtt agcaatttaa   3600
ctgtgataaa ctaccgcatt aaagctcatg cggatcagtg agggtttgca actgcgggtc   3660
aaggatctgg atttcgatca cggcacgatc atcgtgcggg agggcaaggg ctccaaggat   3720
cgggccttga tgttacccga gagcttggca cccagcctgc gcgagcaggg gaattgatcc   3780
ggtggatgac cttttgaatg accttttaata gattatatta ctaattaatt ggggacccta   3840
gaggtcccct ttttattttt aaaaattttt tcacaaaacg gtttacaagc ataaagcttg   3900
gcactggccg tcgttttaca acgtcgtgac tgggaaaacc ctggcgttac ccaacttaat   3960
cgccttgcag cacatccccc tttcgccagc tggcgtaata gcgaagaggc ccgcaccgat   4020
cgcccttccc aacagttgcg cagcctgaat ggcgaatggc gcctgatgcg gtattttctc   4080
cttacgcatc tgtgcggtat ttcacaccgc atatggtgca ctctcagtac aatctgctct   4140
gatgccgcat agttaagcca gccccgacac ccgccaacac ccgctgacgc gccctgacgg   4200
```

```
gcttgtctgc tcccggcatc cgcttacaga caagctgtga ccgtctccgg gagctgcatg   4260
tgtcagaggt tttcaccgtc atcaccgaaa cgcgcgagac gaaagggcct cgtgatacgc   4320
ctatttttat aggttaatgt catgataata atggtttctt agacgtcagg tggcactttt   4380
cggggaaatg tgcgcggaac ccctatttgt ttatttttct aaatacattc aaatatgtat   4440
ccgctcatga caataaccc tgataaatg cttcaataat attgaaaaag gaagagtatg   4500
agtattcaac atttccgtgt cgcccttatt ccctttttg cggcattttg ccttcctgtt   4560
tttgctcacc cagaaacgct ggtgaaagta aaagatgctg aagatcagtt gggtgcacga   4620
gtgggttaca tcgaactgga tctcaacagc ggtaagatcc ttgagagttt cgccccgaa   4680 gaacgttttc caatgatgag cacttttaaa gttctgctat gtggcgcggt attatcccgt   4740
attgacgccg ggcaagagca actcggtcgc cgcatacact attctcagaa tgacttggtt   4800
gagtactcac cagtcacaga aaagcatctt acggatggca tgacagtaag agaattatgc   4860
agtgctgcca taaccatgag tgataacact gcggccaact tacttctgac aacgatcgga   4920
ggaccgaagg agctaaccgc ttttttgcac aacatggggg atcatgtaac tcgccttgat   4980
cgttgggaac cggagctgaa tgaagccata ccaaacgacg agcgtgacac cacgatgcct   5040
gtagcaatgg caacaacgtt gcgcaaacta ttaactggcg aactacttac tctagcttcc   5100
cggcaacaat taatagactg gatggaggcg gataaagttg caggaccact tctgcgctcg   5160
gcccttccgg ctggctggtt tattgctgat aaatctggag ccggtgagcg tgggtctcgc   5220
ggtatcattg cagcactggg gccagatggt aagccctccc gtatcgtagt tatctacacg   5280
acggggagtc aggcaactat ggatgaacga atagacaga tcgctgagat aggtgcctca   5340
ctgattaagc attggtaact gtcagaccaa gtttactcat atatacttta gattgattta   5400
aaacttcatt tttaatttaa aaggatctag gtgaagatcc tttttgataa tctcatgacc   5460
aaaatccctt aacgtgagtt ttcgttccac tgagcgtcag accccgtaga aaagatcaaa   5520
ggatcttctt gagatccttt ttttctgcgc gtaatctgct gcttgcaaac aaaaaaacca   5580
ccgctaccag cggtggtttg tttgccggat caagagctac caactctttt tccgaaggta   5640
actggcttca gcagagcgca gataccaaat actgtccttc tagtgtagcc gtagttaggc   5700
caccacttca agaactctgt agcaccgcct acatacctcg ctctgctaat cctgttacca   5760
gtggctgctg ccagtggcga taagtcgtgt cttaccgggt tggactcaag acgatagtta   5820
ccggataagg cgcagcggtc gggctgaacg gggggttcgt gcacacagcc cagcttggag   5880
cgaacgacct acaccgaact gagatacctac agcgtgagc tatgagaaag cgccacgctt   5940
cccgaaggga gaaaggcgga caggtatccg gtaagcggca gggtcggaac aggagagcgc   6000
acgagggagc ttccagggggg aaacgcctgg tatctttata gtcctgtcgg gtttcgccac   6060
ctctgacttg agcgtcgatt tttgtgatgc tcgtcagggg ggcggagcct atggaaaaac   6120
gccagcaacg cggccttttt acggttcctg gccttttgct ggccttttgc tcacatgttc   6180
tttcctgcgt tatcccctga ttctgtggat aaccgtatta ccgcctttga gtgagctgat   6240
accgctcgcc gcagccgaac gaccgagcgc agcgagtcag tgagcgagga agcggaaga   6299
```

<210> SEQ ID NO 11
<211> LENGTH: 2297
<212> TYPE: DNA
<213> ORGANISM: Artificial Sequence
<220> FEATURE:
<223> OTHER INFORMATION: cloning vector derived from pUC18

<400> SEQUENCE: 11

```
gcgcccaata cgcaaaccgc ctctccccgc gcgttggccg attcattaat gcagaattcg    60
agctcggtac ccggggatcc tctagagtcg acctgcaggc atgcaagctt atggtgcact   120
ctcagtacaa tctgctctga tgccgcatag ttaagccagc cccgacaccc gccaacaccc   180
gctgacgcgc cctgacgggc ttgtctgctc ccggcatccg cttacagaca agctgtgacc   240
gtctccggga gctgcatgtg tcagaggttt tcaccgtcat caccgaaacg cgcgagacga   300
aagggcctcg tgatacgcct atttttatag gttaatgtca tgataataat ggtttcttag   360
acgtcaggtg gcacttttcg ggaaatgtg cgcggaaccc ctatttgttt attttttctaa   420
atacattcaa atatgtatcc gctcatgaga caataaccct gataaatgct tcaataatat   480
tgaaaaagga gagtatgag tattcaacat tccgtgtcg cccttattcc ctttttttgcg   540
gcattttgcc ttcctgtttt tgctcaccca gaaacgctgg tgaaagtaaa agatgctgaa   600
gatcagttgg gtgcacgagt gggttacatc gaactggatc tcaacagcgg taagatcctt   660
gagagttttc gccccgaaga acgttttcca atgatgagca cttttaaagt tctgctatgt   720
ggcgcggtat tatcccgtat tgacgccggg caagagcaac tcggtcgccg catacactat   780
tctcagaatg acttggttga gtactcacca gtcacagaaa agcatcttac ggatggcatg   840
acagtaagag aattatgcag tgctgccata accatgagtg ataacactgc ggccaactta   900
cttctgacaa cgatcggagg accgaaggag ctaaccgctt ttttgcacaa catgggggat   960
catgtaactc gccttgatcg ttgggaaccg gagctgaatg aagccatacc aaacgacgag  1020
cgtgacacca cgatgcctgt agcaatggca acaacgttgc gcaaactatt aactggcgaa  1080
ctacttactc tagcttcccg gcaacaatta atagactgga tggaggcgga taaagttgca  1140
ggaccacttc tgcgctcggc ccttccggct ggctggttta ttgctgataa atctggagcc  1200
ggtgagcgtg ggtctcgcgg tatcattgca gcactggggc cagatggtaa gccctcccgt  1260
atcgtagtta tctacacgac ggggagtcag gcaactatgg atgaacgaaa tagacagatc  1320
gctgagatag gtgcctcact gattaagcat tggtaactgt cagaccaagt ttactcatat  1380
atactttaga ttgatttaaa acttcatttt taatttaaaa ggatctaggt gaagatcctt  1440
tttgataatc tcatgaccaa aatcccttaa cgtgagtttt cgttccactg agcgtcagac  1500
cccgtagaaa agatcaaagg atcttcttga gatccttttt ttctgcgcgt aatctgctgc  1560
ttgcaaacaa aaaaaccacc gctaccagcg gtggtttgtt tgccggatca agagctacca  1620
actctttttc cgaaggtaac tggcttcagc agagcgcaga taccaaatac tgtccttcta  1680
gtgtagccgt agttaggcca ccacttcaag aactctgtag caccgcctac atacctcgct  1740
ctgctaatcc tgttaccagt ggctgctgcc agtggcgata gtcgtgtct taccgggttg  1800
gactcaagac gatagttacc ggataaggcg cagcggtcgg gctgaacggg gggttcgtgc  1860
acacagccca gcttggagcg aacgacctac accgaactga tacctaca gcgtgagcta  1920
tgagaaagcg ccacgcttcc cgaagggaga aaggcggaca ggtatccggt aagcggcagg  1980
gtcggaacag gagagcgcac gagggagctt ccagggggaa acgcctggta tctttatagt  2040
cctgtcgggt ttcgccacct ctgacttgag cgtcgatttt tgtgatgctc gtcagggggg  2100
cggagcctat ggaaaaacgc cagcaacgcg gcctttttac ggttcctggc cttttgctgg  2160
ccttttgctc acatgttctt tcctgcgtta tcccctgatt ctgtggataa ccgtattacc  2220
gcctttgagt gagctgatac cgctcgccgc agccgaacga ccgagcgcag cgagtcagtg  2280
agcgaggaag cggaaga                                                 2297
```

<210> SEQ ID NO 12
<211> LENGTH: 3031
<212> TYPE: DNA
<213> ORGANISM: Artificial Sequence
<220> FEATURE:
<223> OTHER INFORMATION: udp and deoD cloned into pGM746 without
      upstream ptac promoter

<400> SEQUENCE: 12

```
gcgcccaata cgcaaaccgc ctctccccgc gcgttggccg attcattaat gcagaattcg      60
agctcggtac ccggggatcc tagcaggagg gaattcttcc atggctaccc cacacattaa     120
tgcagaaatg ggcgatttcg ctgacgtagt tttgatgcca ggcgaccgc tgcgtgcgaa      180
gtatattgct gaaactttcc ttgaagatgc ccgtgaagtg aacaacgttc gcggtatgct     240
gggcttcacc ggtacttaca aaggccgcaa aatttccgta atgggtcacg gtatgggtat     300
cccgtcctgc tccatctaca ccaaagaact gatcaccgat tcggcgtga agaaaattat      360
ccgcgtgggt tcctgtggcg cagttctgcc gcacgtaaaa ctgcgcgacg tcgttatcgg     420
tatgggtgcc tgcaccgatt ccaaagttaa ccgcatccgt tttaaagacc atgactttgc     480
cgctatcgct gacttcgaca tggtgcgtaa cgcagtagat gcagctaaag cactgggtat     540
tgatgctcgc gtgggtaacc tgttctccgc tgacctgttc tactctccgg acggcgaaat     600
gttcgacgtg atggaaaaat acggcattct cggcgtggaa atggaagcgg ctggtatcta     660
cggcgtcgct gcagaatttg gcgcgaaagc cctgaccatc tgcaccgtat ctgaccacat     720
ccgcactcac gagcagacca ctgccgctga gcgtcagact accttcaacg acatgatcaa     780
aatcgcactg gaatccgttc tgctgggcga taaagagtaa gtcgacctgc aggcatgcaa     840
gcttatggtg cactctcagt acaatctgct ctgatgccgc atagttaagc cagccccgac     900
acccgccaac acccgctgac gcgccctgac gggcttgtct gctcccggca tccgcttaca     960
gacaagctgt gaccgtctcc gggagctgca tgtgtcagag gttttcaccg tcatcaccga    1020
aacgcgcgag acgaaagggc ctcgtgatac gcctattttt ataggttaat gtcatgataa    1080
taatggtttc ttagacgtca ggtggcactt ttcggggaaa tgtgcgcgga acccctattt    1140
gtttattttt ctaaatacat tcaaatatgt atccgctcat gagacaataa ccctgataaa    1200
tgcttcaata atattgaaaa aggaagagta tgagtattca actttccgt gtcgccctta     1260
ttccctttttt tgcggcattt tgccttcctg tttttgctca cccagaaacg ctggtgaaag    1320
taaaagatgc tgaagatcag ttgggtgcac gagtgggtta tcgaactg gatctcaaca      1380
gcggtaagat ccttgagagt tttcgccccg aagaacgttt tccaatgatg agcacttttta   1440
aagttctgct atgtggcgcg gtattatccc gtattgacgc cgggcaagag caactcggtc    1500
gccgcataca ctattctcag aatgacttgg ttgagtactc accagtcaca gaaaagcatc    1560
ttacggatgg catgacagta agagaattat gcagtgctgc cataaccatg agtgataaca    1620
ctgcggccaa cttacttctg acaacgatcg gaggaccgaa ggagctaacc gcttttttgc    1680
acaacatggg ggatcatgta actcgccttg atcgttggga accggagctg aatgaagcca    1740
taccaaacga cgagcgtgac accacgatgc ctgtagcaat ggcaacaacg ttgcgcaaac    1800
tattaactgg cgaactactt actctagctt cccggcaaca attaatagac tggatggagg    1860
cggataaagt tgcaggacca cttctgcgct cggcccttcc ggctggctgg tttattgctg    1920
ataaatctgg agccggtgag cgtgggtctc gcggtatcat tgcagcactg ggccagatg     1980
gtaagccctc ccgtatcgta gttatctaca cgacggggag tcaggcaact atggatgaac    2040
```

-continued

```
gaaatagaca gatcgctgag ataggtgcct cactgattaa gcattggtaa ctgtcagacc    2100
aagtttactc atatatactt tagattgatt taaaacttca ttttaattt aaaaggatct     2160 aggtgaagat cctttttgat aatctcatga ccaaaatccc ttaacgtgag ttttcgttcc    2220
actgagcgtc agacccgta gaaaagatca aaggatcttc ttgagatcct ttttttctgc    2280
gcgtaatctg ctgcttgcaa acaaaaaaac caccgctacc agcggtggtt tgtttgccgg    2340
atcaagagct accaactctt tttccgaagg taactggctt cagcagagcg cagataccaa    2400
atactgtcct tctagtgtag ccgtagttag gccaccactt caagaactct gtagcaccgc    2460
ctacatacct cgctctgcta atcctgttac cagtggctgc tgccagtggc gataagtcgt    2520
gtcttaccgg gttggactca agacgatagt taccggataa ggcgcagcgg tcgggctgaa    2580
cggggggttc gtgcacacag cccagcttgg agcgaacgac ctacaccgaa ctgagatacc    2640
tacagcgtga gctatgagaa agcgccacgc ttcccgaagg gagaaaggcg gacaggtatc    2700
cggtaagcgg cagggtcgga acaggagagc gcacgaggga gcttccaggg ggaaacgcct    2760
ggtatcttta tagtcctgtc gggtttcgcc acctctgact tgagcgtcga ttttgtgat     2820 gctcgtcagg ggggcggagc ctatggaaaa acgccagcaa cgcggccttt ttacggttcc    2880
tggccttttg ctggccttt gctcacatgt tctttcctgc gttatcccct gattctgtgg     2940
ataaccgtat taccgccttt gagtgagctg ataccgctcg ccgcagccga acgaccgagc    3000
gcagcgagtc agtgagcgag gaagcggaag a                                   3031
```

<210> SEQ ID NO 13
<211> LENGTH: 3128
<212> TYPE: DNA
<213> ORGANISM: Artificial Sequence
<220> FEATURE:
<223> OTHER INFORMATION: deoD cloned downstream ptac promoter

<400> SEQUENCE: 13

```
gcgcccaata cgcaaaccgc ctctccccgc gcgttggccg attcattaat gcagaattcg     60
agctccgaca tcataacggt tctggcaaat attctgaaat gagctgttga caattaatca    120
tcggctcgta taatgtgtgg aattgtgagc ggataacaat ttcacacagg aggatcctag    180
caggagggaa ttcttccatg gctacccac acattaatgc agaaatgggc gatttcgctg     240
acgtagtttt gatgccaggc gacccgctgc gtgcgaagta tattgctgaa actttccttg    300
aagatgcccg tgaagtgaac aacgttcgcg gtatgctggg cttcaccggt acttacaaag    360
gccgcaaaat ttccgtaatg ggtcacggta tgggtatccc gtcctgctcc atctacacca    420
aagaactgat caccgatttc ggcgtgaaga aaattatccg cgtgggttcc tgtggcgcag    480
ttctgccgca cgtaaaactg cgcgacgtcg ttatcggtat gggtgcctgc accgattcca    540
aagttaaccg catccgtttt aaagaccatg actttgccgc tatcgctgac ttcgacatgg    600
tgcgtaacgc agtagatgca gctaaagcac tgggtattga tgctcgcgtg ggtaacctgt    660
tctccgctga cctgttctac tctccggacg gcgaaatgtt cgacgtgatg gaaaaatacg    720
gcattctcgg cgtggaaatg gaagcggctg gtatctacgg cgtcgctgca gaatttggcg    780
cgaaagccct gaccatctgc accgtatctg accacatccg cactcacgag cagaccactg    840
ccgctgagcg tcagactacc ttcaacgaca tgatcaaaat cgcactggaa tccgttctgc    900
tgggcgataa agagtaagtc gacctgcagg catgcaagct tatggtgcac tctcagtaca    960
atctgctctg atgccgcata gttaagccag ccccgacacc cgccaacacc cgctgacgcg    1020
ccctgacggg cttgtctgct cccggcatcc gcttacagac aagctgtgac cgtctccggg    1080
```

```
agctgcatgt gtcagaggtt ttcaccgtca tcaccgaaac gcgcgagacg aaagggcctc    1140
gtgatacgcc tattttata ggttaatgtc atgataataa tggtttctta gacgtcaggt    1200
ggcactttc ggggaaatgt gcgcggaacc cctatttgtt tatttttcta aatacattca    1260
aatatgtatc cgctcatgag acaataaccc tgataaatgc ttcaataata ttgaaaaagg    1320
aagagtatga gtattcaaca tttccgtgtc gcccttattc ccttttttgc ggcattttgc    1380
cttcctgttt ttgctcaccc agaaacgctg gtgaaagtaa aagatgctga agatcagttg    1440
ggtgcacgag tgggttacat cgaactggat ctcaacagcg gtaagatcct tgagagtttt    1500
cgccccgaag aacgttttcc aatgatgagc acttttaaag ttctgctatg tggcgcggta    1560
ttatcccgta ttgacgccgg gcaagagcaa ctcggtcgcc gcatacacta ttctcagaat    1620
gacttggttg agtactcacc agtcacagaa aagcatctta cggatggcat gacagtaaga    1680
gaattatgca gtgctgccat aaccatgagt gataacactg cggccaactt acttctgaca    1740
acgatcggag gaccgaagga gctaaccgct tttttgcaca catgggggga tcatgtaact    1800
cgccttgatc gttgggaacc ggagctgaat gaagccatac caaacgacga gcgtgacacc    1860
acgatgcctg tagcaatggc aacaacgttg cgcaaactat taactggcga actacttact    1920
ctagcttccc ggcaacaatt aatagactgg atggaggcgg ataaagttgc aggaccactt    1980
ctgcgctcgg cccttccggc tggctggttt attgctgata aatctggagc cggtgagcgt    2040
gggtctcgcg gtatcattgc agcactgggg ccagatggta agccctcccg tatcgtagtt    2100
atctacacga cggggagtca ggcaactatg gatgaacgaa atagacagat cgctgagata    2160
ggtgcctcac tgattaagca ttggtaactg tcagaccaag tttactcata tactttag    2220
attgatttaa aacttcattt ttaatttaaa aggatctagg tgaagatcct ttttgataat    2280
ctcatgacca aaatccctta acgtgagttt tcgttccact gagcgtcaga ccccgtagaa    2340
aagatcaaag gatcttcttg agatcctttt tttctgcgcg taatctgctg cttgcaaaca    2400
aaaaaaccac cgctaccagc ggtggtttgt ttgccggatc aagagctacc aactcttttt    2460
ccgaaggtaa ctggcttcag cagagcgcag ataccaaata ctgtccttct agtgtagccg    2520
tagttaggcc accacttcaa gaactctgta gcaccgccta catacctcgc tctgctaatc    2580
ctgttaccag tggctgctgc cagtggcgat aagtcgtgtc ttaccgggtt ggactcaaga    2640
cgatagttac cggataaggc gcagcggtcg ggctgaacgg ggggttcgtg cacacagccc    2700
agcttggagc gaacgaccta caccgaactg agatacctac agcgtgagct atgagaaagc    2760
gccacgcttc ccgaagggag aaaggcggac aggtatccgg taagcggcag gtcggaaca    2820
ggagagcgca cgagggagct tccaggggga aacgcctggt atctttatag tcctgtcggg    2880
tttcgccacc tctgacttga gcgtcgattt ttgtgatgct cgtcaggggg cggagccta    2940
tggaaaaacg ccagcaacgc ggcctttta cggttcctgg ccttttgctg gccttttgct    3000
cacatgttct ttcctgcgtt atcccctgat tctgtggata accgtattac cgcctttgag    3060
tgagctgata ccgctcgccg cagccgaacg accgagcgca gcgagtcagt gagcgaggaa    3120
gcggaaga                                                           3128
```

<210> SEQ ID NO 14
<211> LENGTH: 3934
<212> TYPE: DNA
<213> ORGANISM: Artificial Sequence
<220> FEATURE:
<223> OTHER INFORMATION: udp and deoD cloned downstream ptac promoter

<400> SEQUENCE: 14

```
gcgcccaata cgcaaaccgc ctctccccgc gcgttggccg attcattaat gcagaattcg      60
agctccgaca tcataacggt tctggcaaat attctgaaat gagctgttga caattaatca     120
tcggctcgta taatgtgtgg aattgtgagc ggataacaat tcacacagg aggatcctag      180
caggagggaa ttcttccatg ctacccac acattaatgc agaaatgggc gatttcgctg       240
acgtagtttt gatgccaggc gacccgctgc gtgcgaagta tattgctgaa actttccttg    300
aagatgcccg tgaagtgaac aacgttcgcg gtatgctggg cttcaccggt acttacaaag    360
gccgcaaaat ttccgtaatg ggtcacggta tgggtatccc gtcctgctcc atctacacca    420
aagaactgat caccgatttc ggcgtgaaga aaattatccg cgtgggttcc tgtggcgcag    480
ttctgccgca cgtaaaactg cgcgacgtcg ttatcggtat gggtgcctgc accgattcca    540
aagttaaccg catccgtttt aaagaccatg actttgccgc tatcgctgac ttcgacatgg    600
tgcgtaacgc agtagatgca gctaaagcac tgggtattga tgctcgcgtg ggtaacctgt    660
tctccgctga cctgttctac tctccggacg gcgaaatgtt cgacgtgatg gaaaaatacg    720
gcattctcgg cgtggaaatg gaagcggctg gtatctacgg cgtcgctgca gaatttggcg    780
cgaaagccct gaccatctgc accgtatctg accacatccg cactcacgag cagaccactg    840
ccgctgagcg tcagactacc ttcaacgaca tgatcaaaat cgcactggaa tccgttctgc    900
tgggcgataa agagtaagtc gacacaggaa acagctatga ccatgattac gaattcgagc    960
tcggtaccat ccatgtccaa gtctgatgtt tttcatctcg gcctcactaa aaacgattta   1020
caagggcta cgcttgccat cgtccctggc gacccggatc gtgtggaaaa gatcgccgcg    1080
ctgatggata gccggttaa gctggcatct caccgcgaat tcactacctg gcgtgcagag    1140
ctggatggta aacctgttat cgtctgctct accggtatcg gcggcccgtc tacctctatt    1200
gctgttgaag agctggcaca gctgggcatt cgcaccttcc tgcgtatcgg tacaacgggc    1260
gctattcagc cgcatattaa tgtgggtgat gtcctggtta ccacggcgtc tgtccgtctg    1320
gatggcgcga gcctgcactt cgcaccgctg gaattcccgg ctgtcgctga tttcgaatgt    1380
acgactgcgc tggttgaagc tgcgaaatcc attggcgcga caactcacgt tggcgtgaca    1440
gcttcttctg ataccttcta cccaggtcag gaacgttacg atacttactc tggtcgcgta    1500
gttcgtcact ttaaaggttc tatggaagag tggcaggcga tgggcgtaat gaactatgaa    1560
atggaatctg caaccctgct gaccatgtgt gcaagtcagg gcctgcgtgc cggtatggta    1620
gcgggtgtta tcgttaaccg cacccagcaa gagatcccga tgctgagac gatgaaacaa     1680
accgaaagcc atgcggtgaa atcgtggtg gaagcggcgc gtcgtctgct gtaattctct    1740
taagcttatg gtgcactctc agtacaatct gctctgatgc cgcatagtta agccagcccc    1800
gacacccgcc aacacccgct gacgcgccct gacgggcttg tctgctcccg gcatccgctt    1860
acagacaagc tgtgaccgtc tccgggagct gcatgtgtca gaggttttca ccgtcatcac    1920
cgaaacgcgc gagacgaaag ggcctcgtga tacgcctatt tttataggtt aatgtcatga    1980
taataatggt ttcttagacg tcaggtggca cttttcgggg aaatgtgcgc ggaacccta    2040
tttgtttatt tttctaaata cattcaaata tgtatccgct catgagacaa taaccctgat    2100
aaatgcttca ataatattga aaaggaaga gtatgagtat tcaacatttc cgtgtcgccc    2160
ttattccctt ttttgcggca ttttgccttc ctgttttgc tcacccagaa acgctggtga    2220
aagtaaaaga tgctgaagat cagttgggtg cacgagtggg ttacatcgaa ctggatctca    2280
acagcggtaa gatccttgag agttttcgcc ccgaagaacg ttttccaatg atgagcactt    2340
```

```
ttaaagttct gctatgtggc gcggtattat cccgtattga cgccgggcaa gagcaactcg    2400
gtcgccgcat acactattct cagaatgact tggttgagta ctcaccagtc acagaaaagc    2460
atcttacgga tggcatgaca gtaagagaat tatgcagtgc tgccataacc atgagtgata    2520
acactgcggc caacttactt ctgacaacga tcggaggacc gaaggagcta accgcttttt    2580
tgcacaacat gggggatcat gtaactcgcc ttgatcgttg ggaaccggag ctgaatgaag    2640
ccataccaaa cgacgagcgt gacaccacga tgcctgtagc aatggcaaca cgttgcgca    2700 aactattaac tggcgaacta cttactctag cttcccggca acaattaata gactggatgg    2760
aggcggataa agttgcagga ccacttctgc gctcggccct tccggctggc tggtttattg    2820
ctgataaatc tggagccggt gagcgtgggt ctcgcggtat cattgcagca ctggggccag    2880
atggtaagcc ctcccgtatc gtagttatct acacgacggg gagtcaggca actatggatg    2940
aacgaaatag acagatcgct gagataggtg cctcactgat taagcattgg taactgtcag    3000
accaagttta ctcatatata ctttagattg atttaaaact tcattttaa tttaaaagga    3060 tctaggtgaa gatccttttt gataatctca tgaccaaaat cccttaacgt gagttttcgt    3120
tccactgagc gtcagacccc gtagaaaaga tcaaaggatc ttcttgagat ccttttttc    3180 tgcgcgtaat ctgctgcttg caaacaaaaa accaccgct accagcggtg gtttgtttgc    3240
cggatcaaga gctaccaact cttttttcga aggtaactgg cttcagcaga gcgcagatac    3300
caaatactgt ccttctagtg tagccgtagt taggccacca cttcaagaac tctgtagcac    3360
cgcctacata cctcgctctg ctaatcctgt taccagtggc tgctgccagt ggcgataagt    3420
cgtgtcttac cgggttggac tcaagacgat agttaccgga taaggcgcag cggtcgggct    3480 gaacggggg ttcgtgcaca cagcccagct tggagcgaac gacctacacc gaactgagat    3540
acctacagcg tgagctatga gaaagcgcca cgcttcccga agggagaaag gcggacaggt    3600
atccggtaag cggcagggtc ggaacaggag agcgcacgag ggagcttcca ggggaaacg    3660 cctggtatct ttatagtcct gtcgggtttc gccacctctg acttgagcgt cgatttttgt    3720
gatgctcgtc agggggggcg gagcctatgga aaaacgccag caacgcggcc ttttttacggt   3780 tcctggcctt ttgctggcct tttgctcaca tgttctttcc tgcgttatcc cctgattctg    3840
tggataaccg tattaccgcc tttgagtgag ctgataccgc tcgccgcagc cgaacgaccg    3900
agcgcagcga gtcagtgagc gaggaagcgg aaga                                3934
```

<210> SEQ ID NO 15
<211> LENGTH: 6046
<212> TYPE: DNA
<213> ORGANISM: Artificial Sequence
<220> FEATURE:
<223> OTHER INFORMATION: udp and deoD cloned downstream ptac promoter

<400> SEQUENCE: 15

```
gcgcccaata cgcaaaccgc ctctccccgc gcgttggccg attcattaat gcagaattcg     60
agctccgaca tcataacggt tctggcaaat attctgaaat gagctgttga caattaatca    120
tcggctcgta taatgtgtgg aattgtgagc ggataacaat ttcacacagg aggatcctag    180
caggagggaa ttcttccatg gctaccccac acattaatgc agaaatgggc gatttcgctg    240
acgtagtttt gatgccaggc gacccgctgc gtgcgaagta tattgctgaa ctttccttg    300 aagatgcccg tgaagtgaac aacgttcgcg gtatgctggg cttcaccggt acttacaaag    360
gccgcaaaat ttccgtaatg ggtcacggta tgggtatccc gtcctgctcc atctacacca    420
```

```
aagaactgat caccgatttc ggcgtgaaga aaattatccg cgtgggttcc tgtggcgcag    480
ttctgccgca cgtaaaactg cgcgacgtcg ttatcggtat gggtgcctgc accgattcca    540
aagttaaccg catccgtttt aaagaccatg actttgccgc tatcgctgac ttcgacatgg    600
tgcgtaacgc agtagatgca gctaaagcac tgggtattga tgctcgcgtg ggtaacctgt    660
tctccgctga cctgttctac tctccggacg gcgaaatgtt cgacgtgatg gaaaaatacg    720
gcattctcgg cgtggaaatg gaagcggctg gtatctacgg cgtcgctgca gaatttggcg    780
cgaaagccct gaccatctgc accgtatctg accacatccg cactcacgag cagaccactg    840
ccgctgagcg tcagactacc ttcaacgaca tgatcaaaat cgcactggaa tccgttctgc    900
tgggcgataa agagtaagtc gacacaggaa acagctatga ccatgattac gaattcgagc    960
tcggtaccat ccatgtccaa gtctgatgtt tttcatctcg gcctcactaa aaacgattta   1020
caaggggcta cgcttgccat cgtccctggc gacccggatc gtgtggaaaa gatcgccgcg   1080
ctgatggata agccggttaa gctggcatct caccgcgaat tcactacctg cgtgcagag    1140 ctggatggta aacctgttat cgtctgctct accggtatcg gcggcccgtc tacctctatt   1200
gctgttgaag agctggcaca gctgggcatt cgcaccttcc tgcgtatcgg tacaacgggc   1260
gctattcagc cgcatattaa tgtgggtgat gtcctggtta ccacggcgtc tgtccgtctg   1320
gatggcgcga gcctgcactt cgcaccgctg gaattcccgg ctgtcgctga tttcgaatgt   1380
acgactgcgc tggttgaagc tgcgaaatcc attggcgcga caactcacgt tggcgtgaca   1440
gcttcttctg ataccttcta cccaggtcag gaacgttacg atacttactc tggtcgcgta   1500
gttcgtcact ttaaaggttc tatggaagag tggcaggcga tgggcgtaat gaactatgaa   1560
atggaatctg caaccctgct gaccatgtgt gcaagtcagg gcctgcgtgc cggtatggta   1620
gcgggtgtta tcgttaaccg cacccagcaa gagatcccga atgctgagac gatgaaacaa   1680
accgaaagcc atgcggtgaa aatcgtggtg gaagcggcgc gtcgtctgct gtaattctct   1740
taagctttat gcttgtaaac cgttttgtga aaaaattttt aaaataaaaa aggggacctc   1800
tagggtcccc aattaattag taatataatc tattaaaggt cattcaaaag gtcatccacc   1860
ggatcagctt agtaaagccc tcgctagatt ttaatgcgga tgttgcgatt acttcgccaa   1920
ctattgcgat aacaagaaaa agccagcctt tcatgatata tctcccaatt tgtgtagggc   1980
ttattatgca cgcttaaaaa taataaaagc agacttgacc tgatagtttg gctgtgagca   2040
attatgtgct tagtgcatct aacgcttgag ttaagccgcg ccgcgaagcg gcgtcggctt   2100
gaacgaattg ttagacatta tttgccgact accttggtga tctcgccttt cacgtagtgg   2160
acaaattctt ccaactgatc tgcgcgccga gatgcgccgc gtgcggctgc tggagatggc   2220
ggacgcgatg gatatgttct gccaagggtt ggtttgcgca ttcacagttc tccgcaagaa   2280
ttgattggct ccaattcttg gagtggtgaa tccgttagcg aggtgccgcc ggcttccatt   2340
caggtcgagg tggcccggct ccatgcaccg cgacgcaacg cggggaggca gacaaggtat   2400
agggcggcgc ctacaatcca tgccaacccg ttccatgtgc tcgccgaggc ggcataaatc   2460
gccgtgacga tcagcggtcc agtgatcgaa gttaggctgg taagagccgc gagcgatcct   2520
tgaagctgtc cctgatggtc gtcatctacc tgcctggaca gcatggcctg caacgcgggc   2580
atcccgatgc cgccggaagc gagaagaatc ataatgggga aggccatcca gcctcgcgtc   2640
gcgaacgcca gcaagacgta gcccagcgcg tcggccgcca tgccggcgat aatggcctgc   2700
ttctcgccga aacgtttggt ggcgggacca gtgacgaagg cttgagcgag ggcgtgcaag   2760
attccgaata ccgcaagcga caggccgatc atcgtcgcgc tccagcgaaa gcggtcctcg   2820
```

```
ccgaaaatga cccagagcgc tgccggcacc tgtcctacga gttgcatgat aaagaagaca   2880
gtcataagtg cggcgacgat agtcatgccc cgcgcccacc ggaaggagct gactgggttg   2940
aaggctctca agggcatcgg tcgacgctct cccttatgcg actcctgcat taggaagcag   3000
cccagtagta ggttgaggcc gttgagcacc gccgccgcaa ggaatggtgc atgcaaggag   3060
atggcgccca acagtccccc ggccacgggg cctgccacca tacccacgcc gaaacaagcg   3120
ctcatgagcc cgaagtggcg agcccgatct tccccatcgg tgatgtcggc gatataggcg   3180
ccagcaaccg cacctgtggc gccggtgatg ccggccacga tgcgtccggc gtagaggatc   3240
cacaggacgg gtgtggtcgc catgatcgcg tagtcgatag tggctccaag tagcgaagcg   3300
agcaggactg ggcggcggcc aaagcggtcg gacagtgctc cgagaacggg tgcgcataga   3360
aattgcatca acgcatatag cgctagcagc acgccatagt gactggcgat gctgtcggaa   3420
tggacgatat cccgcaagag gcccggcagt accggcataa ccaagcctat gcctacagca   3480
tccagggtga cggtgccgag gatgacgatg agcgcattgt tagatttcat acacggtgcc   3540
tgactgcgtt agcaatttaa ctgtgataaa ctaccgcatt aaagctcatg cggatcagtg   3600
agggtttgca actgcgggtc aaggatctgg atttcgatca cggcacgatc atcgtgcggg   3660
agggcaaggg ctccaaggat cgggccttga tgttacccga gagcttggca cccagcctgc   3720
gcgagcaggg gaattgatcc ggtggatgac cttttgaatg acctttaata gattatatta   3780
ctaattaatt ggggacccta gaggtcccct ttttatttt aaaattttt tcacaaaacg   3840 gtttacaagc ataaagctta tggtgcactc tcagtacaat ctgctctgat gccgcatagt   3900
taagccagcc ccgacacccg ccaacacccg ctgacgcgcc ctgacgggct tgtctgctcc   3960
cggcatccgc ttacagacaa gctgtgaccg tctccgggag ctgcatgtgt cagaggtttt   4020
caccgtcatc accgaaacgc gcgagacgaa agggcctcgt gatacgccta tttttatagg   4080
ttaatgtcat gataataatg gtttcttaga cgtcaggtgg cacttttcgg ggaaatgtgc   4140
gcggaacccc tatttgttta tttttctaaa tacattcaaa tatgtatccg ctcatgagac   4200
aataaccctg ataaatgctt caataatatt gaaaaaggaa gagtatgagt attcaacatt   4260
tccgtgtcgc ccttattccc ttttttgcgg cattttgcct tcctgttttt gctcacccag   4320
aaacgctggt gaaagtaaaa gatgctgaag atcagttggg tgcacgagtg ggttacatcg   4380
aactggatct caacagcggt aagatccttg agagttttcg ccccgaagaa cgttttccaa   4440
tgatgagcac ttttaaagtt ctgctatgtg gcgcggtatt atcccgtatt gacgccgggc   4500
aagagcaact cggtcgccgc atacactatt ctcagaatga cttggttgag tactcaccag   4560
tcacagaaaa gcatcttacg gatggcatga cagtaagaga attatgcagt gctgccataa   4620
ccatgagtga taacactgcg gccaacttac ttctgacaac gatcggagga ccgaaggagc   4680
taaccgcttt tttgcacaac atgggggatc atgtaactcg ccttgatcgt tgggaaccgg   4740
agctgaatga agccatacca aacgacgagc gtgacaccac gatgcctgta gcaatggcaa   4800
caacgttgcg caaactatta actggcgaac tacttactct agcttcccgg caacaattaa   4860
tagactggat ggaggcggat aaagttgcag gaccacttct gcgctcggcc cttccggctg   4920
gctggtttat tgctgataaa tctggagccg gtgagcgtgg gtctcgcggt atcattgcag   4980
cactggggcc agatggtaag ccctcccgta tcgtagttat ctacacgacg gggagtcagg   5040
caactatgga tgaacgaaat agacagatcg ctgagatagg tgcctcactg attaagcatt   5100
ggtaactgtc agaccaagtt tactcatata ctttagat tgatttaaaa cttcattttt   5160
```

-continued

```
aatttaaaag gatctaggtg aagatccttt ttgataatct catgaccaaa atcccttaac      5220
gtgagttttc gttccactga gcgtcagacc ccgtagaaaa gatcaaagga tcttcttgag      5280 atccttttt tctgcgcgta atctgctgct tgcaaacaaa aaaaccaccg ctaccagcgg       5340
tggtttgttt gccggatcaa gagctaccaa ctcttttcc gaaggtaact ggcttcagca       5400
gagcgcagat accaaatact gtccttctag tgtagccgta gttaggccac cacttcaaga     5460
actctgtagc accgcctaca tacctcgctc tgctaatcct gttaccagtg gctgctgcca     5520
gtggcgataa gtcgtgtctt accgggttgg actcaagacg atagttaccg gataaggcgc     5580
agcggtcggg ctgaacgggg ggttcgtgca cacagcccag cttggagcga acgacctaca     5640
ccgaactgag atacctacag cgtgagctat gagaaagcgc cacgcttccc gaagggagaa     5700
aggcggacag gtatccggta agcggcaggg tcggaacagg agagcgcacg agggagcttc     5760 caggggaaa cgcctggtat ctttatagtc ctgtcgggtt tcgccacctc tgacttgagc       5820 gtcgatttt gtgatgctcg tcagggggc ggagcctatg gaaaaacgcc agcaacgcgg        5880 ccttttacg gttcctggcc ttttgctggc cttttgctca catgttcttt cctgcgttat       5940
cccctgattc tgtggataac cgtattaccg cctttgagtg agctgatacc gctcgccgca     6000
gccgaacgac cgagcgcagc gagtcagtga gcgaggaagc ggaaga                    6046
```

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16

```
atcggtacca tccatgtcca agtctgatgt ttttcatctc                            40
```

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17

```
agacggtcga caagagaatt acagcagacg acgc                                  34
```

<210> SEQ ID NO 18
<211> LENGTH: 37
<212> TYPE: DNA
<213> ORGANISM: Artificial Sequence
<220> FEATURE:
<223> OTHER INFORMATION: primer

<400> SEQUENCE: 18

```
ctgaattctt ccatggctac cccacacatt aatgcag                               37
```

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19

```
tcatggtcga cttactcttt atcgcccagc agaacg                                36
```

```
<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
attgagctcg acatcataac ggttctggc                                    29

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
attggatcct gtgtgaaatt gttatccgc                                    29

<210> SEQ ID NO 22
<211> LENGTH: 27
<212> TYPE: DNA
<213> ORGANISM: Artificial Sequence
<220> FEATURE:
<223> OTHER INFORMATION: primer

<400> SEQUENCE: 22
tccagtcgac acaggaaaca gctatga                                      27

<210> SEQ ID NO 23
<211> LENGTH: 29
<212> TYPE: DNA
<213> ORGANISM: Artificial Sequence
<220> FEATURE:
<223> OTHER INFORMATION: primer

<400> SEQUENCE: 23
tacgaagctt aagagaatta cagcagacg                                    29

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
ggccgttaac cgcacccagc aagag                                        25

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
agccatggac agcagacgac gcgcc                                        25

<210> SEQ ID NO 26
<211> LENGTH: 28
<212> TYPE: DNA
<213> ORGANISM: Artificial Sequence
<220> FEATURE:
<223> OTHER INFORMATION: primer
```

<400> SEQUENCE: 26
gctgtccatg gctaccccac acattaat                                              28

<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27
ccgggttaac tttggaatcg gtgcagg                                               27

<210> SEQ ID NO 28
<211> LENGTH: 34
<212> TYPE: DNA
<213> ORGANISM: Artificial Sequence
<220> FEATURE:
<223> OTHER INFORMATION: primer

<400> SEQUENCE: 28
catgggcggt ggcagcccgg gcattctggc catg                                       34

<210> SEQ ID NO 29
<211> LENGTH: 11
<212> TYPE: PRT
<213> ORGANISM: Artificial Sequence
<220> FEATURE:
<223> OTHER INFORMATION: amino acid linker

<400> SEQUENCE: 29

Ser Met Gly Gly Gly Ser Pro Gly Ile Leu Ala
1               5                   10

<210> SEQ ID NO 30
<211> LENGTH: 23
<212> TYPE: PRT
<213> ORGANISM: Artificial
<220> FEATURE:
<223> OTHER INFORMATION: synthetic peptide

<400> SEQUENCE: 30

Trp Met Ile Thr Asn Ser Ser Ser Val Pro Gly Asp Pro Leu Glu Ser
1               5                   10                  15

Thr Cys Arg His Ala Ser Leu
            20

<210> SEQ ID NO 31
<211> LENGTH: 13
<212> TYPE: PRT
<213> ORGANISM: Artificial
<220> FEATURE:
<223> OTHER INFORMATION: synthetic peptide

<400> SEQUENCE: 31

Thr Met Ile Thr Asn Ser Ser Met Ala Thr Pro Trp Ala
1               5                   10

<210> SEQ ID NO 32
<211> LENGTH: 15
<212> TYPE: PRT
<213> ORGANISM: Artificial
<220> FEATURE:
<223> OTHER INFORMATION: synthetic peptide

<400> SEQUENCE: 32

```
Thr Met Ile Thr Asn Ser Ser Val Pro Ser Met Ser Leu Leu
1               5                   10                  15

<210> SEQ ID NO 33
<211> LENGTH: 6
<212> TYPE: PRT
<213> ORGANISM: Artificial
<220> FEATURE:
<223> OTHER INFORMATION: synthetic peptide

<400> SEQUENCE: 33

Met Ala Thr Pro Trp Ala
1               5
```

CATALYZING TRANSGLYCOSYLATION USING A RECOMBINANT HOST CELL OVEREXPRESSING URIDINE PHOSPHORYLASE AND PURINE NUCLEOSIDE PHOSPHORYLASE

This application is a divisional of U.S. Ser. No. 09/891,865 filed on Jun. 25, 2001, now U.S. Pat. No. 6,911,341, which is a continuation of international application Ser. No. PCT/EP99/10416, flied Dec. 23, 1999, each of which is incorporated by reference in their entirety.

The present invention relates to novel genetically modified bacterial strains capable of expressing polypeptides having the enzyme activity of the enzymes UdP and PNP; the strains in question can be used to catalyse transglycosylation reactions between a donor nucleoside and an acceptor base.

Natural nucleosides or the modified analogues thereof have important applications, both directly and as intermediates, in the field of drugs having an anti-viral and anti-tumour action, as well as in the preparation of oligonucleotides for therapeutic and diagnostic use.

Nucleosides can be prepared using methods of chemical synthesis which normally require a large number of steps processes for the protection and deprotection of labile groups and the use of reagents and operating conditions which, on an industrial level, may be both difficult to apply and economically disadvantageous. In addition, those reactions do not generally have high overall yields owing also to the formation of mixtures of stereo- and regio-isomers from which the compound of interest has to be separated.

An alternative approach to the preparation of nucleosides and modified analogues thereof is based on interconversion between a sugar-donating nucleoside and an acceptor base by means of enzymes which catalyse the general reversible reactions (Hutchinson, Trends Biotechnol. 8, 348-353, 1990) given below in scheme 1:

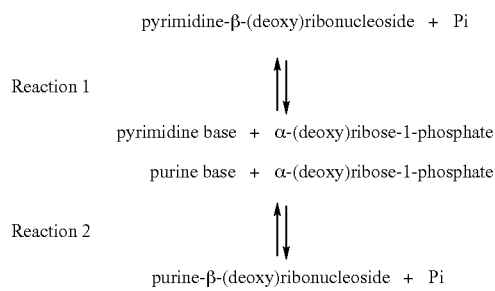

where Pi=organic phosphate.

Reaction 1 is catalysed by the enzyme uridine phosphorylase or UdP (E.C.2.4.2.3.) while reaction 2 is catalysed by the enzyme purine nucleoside phosphorylase or PNP (E.C.2.4.2.1.).

The UdP and PNP enzymes can be used individually to catalyse transglycosylation reactions between a donor pyrimidine nucleoside and an acceptor pyrimidine base or between a donor purine nucleoside and an acceptor purine base, respectively. In addition, when the two enzymes are used in combination, it is possible to transfer the sugar from a donor pyrimidine nucleoside to a purine or pyrimidine acceptor base as well as from a donor purine nucleoside to a pyrimidine or purine acceptor base, depending on the starting materials used. In each case the phosphorolysis reactions involve a configuration change at position 1 of the sugar to give an (α-sugar-1-phosphate which constitutes the intermediate substrate of the transglycosylation reactions and which is subsequently transferred to the acceptor base, with restoration of the original β configuration.

Those enzyme reactions can advantageously be carried out starting from a mixture of a donor nucleoside and an acceptor base in the simultaneous presence of the two enzymes and without isolating the intermediate sugar phosphate or in two steps comprising phosphorolysis with formation of the intermediate sugar phosphate, its isolation and subsequent condensation with the acceptor base.

With regard to chemical synthesis, an important advantage of transglycosylation reactions catalysed by phosphorylases is the maintenance of stereo-selectivity and regio-selectivity, as a result of which the end product retains the β configuration of natural nucleosides.

The UdP and PNP enzymes which participate physiologically in the catabolism and interconversion reactions of nucleosides are the product, respectively, of the udp and deoD genes, occurring widely in nature, and have been identified and studied in both prokaryotic and eukaryotic organisms (Parks and Agarwal, Enzymes 7, 3rd ed., 483-514, Academic Press, New York; Munch-Petersen, Metabolism of nucleotides, nucleosides and nucleobases in micro-organisms, Academic Press, London, 1982).

From the point of view of use as catalysts for the synthesis of nucleosides and modified analogues thereof, the enzymes of prokaryotic organisms are generally preferred because they have a lower substrate specificity and they can catalyse transglycosylation reactions starting also from donor nucleosides containing modified sugars and from acceptor bases comprising both purine or pyrimidine structures and various nitrogen-containing heterocyclic systems (Stoeckler et al., Biochemistry 19, 102-107, 1980; Browska et al., Z. Naturforsch., 45, 59-70, 1990).

The transglycosylation reactions can be carried out using purified or partially purified enzyme preparations (Krenitsky et al., Biochemistry 20, 3615-3621, 1981; EP-002192) or, alternatively, using the whole bacterial cells of microorganisms selected because they contain the necessary enzymes (Utagawa et al., Agric.Biol.Chem. 49, 3239-3246,1985) or whole cells cultivated in the presence of inducers of the production of those enzymes (Doskocil et al., Collect. Czech. Chem. Commun. 42, 370-383, 1977).

For biocatalysis reactions carried out at a preparative level, the use of whole cells both obviates the need to extract and purify the enzymes and enables the cells to be recovered easily at the end of the reaction, for example by centrifugation or ultrafiltration, and to be re-used for other, subsequent, reaction cycles; alternatively, it is possible to use the UdP and PNP enzymes extracted from the cells in the form of a crude or purified soluble cell fraction. Both UdP and PNP are enzymes characterised by good thermal stability which enables the transglycosylation reactions to be carried out at temperatures of up to approximately 60° C. without significant activity losses and enables the recovered enzyme preparations to be re-used. Approaches have also been described where the recycling of cells used as catalysts was carried out by micro-encapsulation in both hydrophilic gels (Votruba et al., Collect.Czech.Chem. Commun. 59, 2303-2330, 1994) and hydrophobic gels (Yokozeki et al., Eur. J. Appl. Microbiol. Biotechnol., 14, 225-231, 1982).

The main limitations of the methods known hitherto for the preparation of natural nucleosides and modified analogues thereof by transglycosylation reactions using bacterial cells reside in the low enzyme concentration obtainable, even after induction, and in the impossibility of using optimised amounts of the two enzyme activities required to catalyse the transfer of the sugar from a donor nucleoside to an acceptor base.

Both in the case of selection of wild-type bacterial strains and in the case of cultivation of strains under induction conditions, cells are obtained that contain levels of UdP and PNP which are generally not higher than 10 times the base levels (F. Ling et al., Process Biochem. 29, 355-361, 1994) and which are in non-predeterminable ratios. Furthermore, because one of the two enzymes (generally PNP) is present in the induced cells in lower amounts, it is usually necessary to use an excess of cells such as to ensure the presence of the limiting enzyme at levels compatible with acceptable overall kinetics of the interconversion reaction. From an operating point of view, this means that a significant portion of the reaction mixture is constituted by the cell suspension, with consequent restriction of the volume that can be used to solubilise the substrates and, finally, with a lower volumetric yield of end product.

The present invention therefore relates to the construction of genetically modified bacterial strains capable of solving the problems described above and, in particular, of catalysing transglycosylation reactions between a donor nucleoside and an acceptor base with high yields which are foreseeable and, above all, reproducible on an industrial scale and with particularly rapid enzyme kinetics.

The literature has described the cloning and expression of some recombinant phosphorylases, such as, for example, human UdP (Watanabe and Uchida, Biochem. Biophys. Res. Commun. 216, 265-272, 1996), murine UdP (Watanabe et al., J. Biol. Chem. 270, 12191-12196, 1995), of *Escherichia coli* (Mikhailov et al., Biochem. Internat. 26, 607-615, 1992) and human PNP (Erion et al., Biochemistry 36, 11725-11734, 1997), of the thermophilic micro-organism *Bacillus stearothermophilus* (Hamamoto et al., Biosci. Biotech. Biochem. 61, 272-275, 1997; Hamamoto et al., Biosci. Biotech. Biochem. 61, 276-280, 1997) in addition to UdP and PNP from *Klebsiella* sp (Takehara et al., Biosci. Biotech. Biochem. 59, 1987-1990, 1995). In particular, Japanese patent application JP-06-253854 describes the expression in *E. coli* of bacterial plasmids containing the gene sequences of the enzymes purine and/or pyrimidine nucleoside phosphorylase derived solely from thermophilic bacteria, that is bacteria having optimum growth at temperatures of from 50 to 60° C., such as, for example, *Bacillus stearotermophilus*.

Novel genetically modified bacterial strains that contain the genes coding for polypeptides having the enzyme activity of the enzymes uridine phosphorylase (UdP) and/or purine nucleoside phosphorylase (PNP), both separately and together, have now been found and constitute part of the subject matter of the present invention. The cultivation of these novel strains enables both high levels of biomass and high levels of expression of the recombinant enzymes to be obtained; the novel strains according to the present invention can also be used either directly or after extraction of the soluble cell fraction as catalysts for the production of natural nucleosides and modified analogues thereof with substantial improvements in the process in comparison with the prior art.

In contrast to what has been described in JP-06-253854, the plasmid vectors according to the present invention can be obtained by cloning both separately and simultaneously the udp and deoD genes of mesophilic bacteria, that is bacteria having optimum growth at temperatures of from 30 to 37° C. such as, for example, *E. coli*. To be more precise, the gene sequences preferably used for the purposes of the present invention are the *E. coli* sequences that encode the udp and deoD genes and that are deposited in the EMBL data bank with the accession numbers X15689 (udp) and M60917 (deoD); however, it is also possible to use other widely available sequences, such as, for example, AC CG01747 (udp) and AC CG00327 (deoD).

The expression plasmid vectors which may be used for the purposes of the invention and which form part of the subject matter thereof are therefore characterised in that they comprise:
 a) at least one gene sequence of a mesophilic bacterium coding for a polypeptide having enzyme UdP and/or enzyme PNP activity; and
 b) at least one gene sequence coding for antibiotic resistance.

The at least one sequence coding for antibiotic resistance is preferably a sequence coding for tetracycline, kanamycin and/or ampicillin resistance. The plasmid vectors of the present invention can be obtained by cloning either the sequence coding for udp and/or the sequence coding for deoD or, optionally, the sequence coding for tetracycline and/or kanamycin resistance into the plasmid pUC18 (Yanish and Perron, Gene 33, 103-119, 1985; EMBL accession number L08752) which already contains the ampicillin resistance gene.

The relative position of the sequences coding for udp and deoD is not, however, relevant for the purposes of the invention: that is to say, the sequence coding for udp can be positioned either downstream or upstream of the sequence coding for deoD. Furthermore, and as it will be appreciated from the Examples which follow, the gene sequences coding for udp and deoD may also be fused together so to express novel fusion proteins wherein the enzymes UdP and PNP are either covalently bonded together (UdP-PNP) or, alternatively, the novel fusion protein may have the formula UdP-(L)-PNP wherein L is a polypeptide linker of more than one aminoacidic unit. In these novel fusion proteins, the relative position of the two components is not however relevant for the purposes of the invention: that is to say, the PNP component can be either at the $NH_2$-terminal or at the COOH-terminal position of the fused proteins. The novel proteins thus obtainable, which are a further object of the present invention, are characterized by possessing a bifunctional activity as they are able to perform both the activity of the enzyme UdP and that of the enzyme PNP.

An additional object of the present invention is then represented by the method for producing the above mentioned fusion proteins, said method comprising:
 (a) producing a plasmid expression vector as above indicated;
 (b) transforming a host bacteria cell with said expression vector; and
 (c) isolating and purifying the fusion protein from the transformed bacteria cell.

BRIEF DESCRIPTION OF THE DRAWINGS

FIGS. 2A to 2D. 5' and 3' sequences of upd and deoD genes cloned in plasmid pUC18 (as shown in SEQ ID NO:6). Restriction sites of different constructs are underlined. The bases of nucleotide sequences of udp and deoD genes (corresponding to nucleotides 243-2021 and 1037-1766 of SEQ ID NO:6, respectively) and selected amino acid residues of PNP (SEQ ID NO:31 and 33) and UdP proteins (SEQ ID NO:32) are reported in italics. (A) Plasmid pUC18: 5' sequence fragment of lacZ gene (as shown in SEQ ID NO:6, amino acid fragment SEQ ID NO:30). (B) Plasmid pGM678 and pGM707: 5' and 3' sequence fragments of lacZ-deoD fused gene (as shown in SEQ ID NO:3 and SEQ ID NO:4, amino acid fragment SEQ ID NO:31). (C) plasmid pGM679 and pGM708: 5' and 3' sequence fragments of lacZ-upd fused genes (as shown in SEQ ID NO: 1 and SEQ ID NO:2, amino acid fragment SEQ ID NO:32). (D) Plasmid pGM712 and pGM716: 5' and 3' sequence fragments of deoD gene (as shown in SEQ ID NO:5 and SEQ ID NO:6, amino acid fragment SEQ ID NO:33).

Figure 3A:
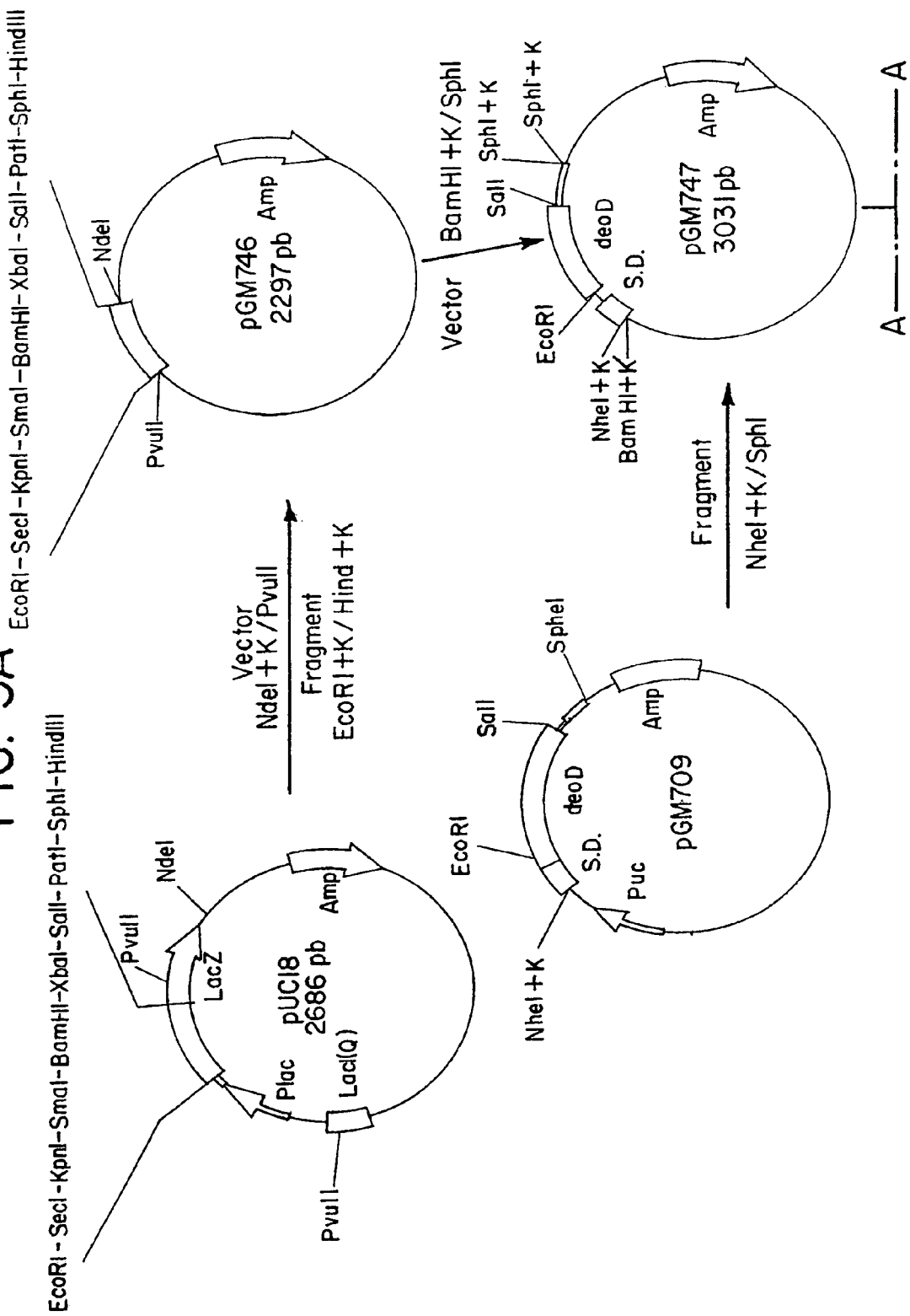
Figure 3B:
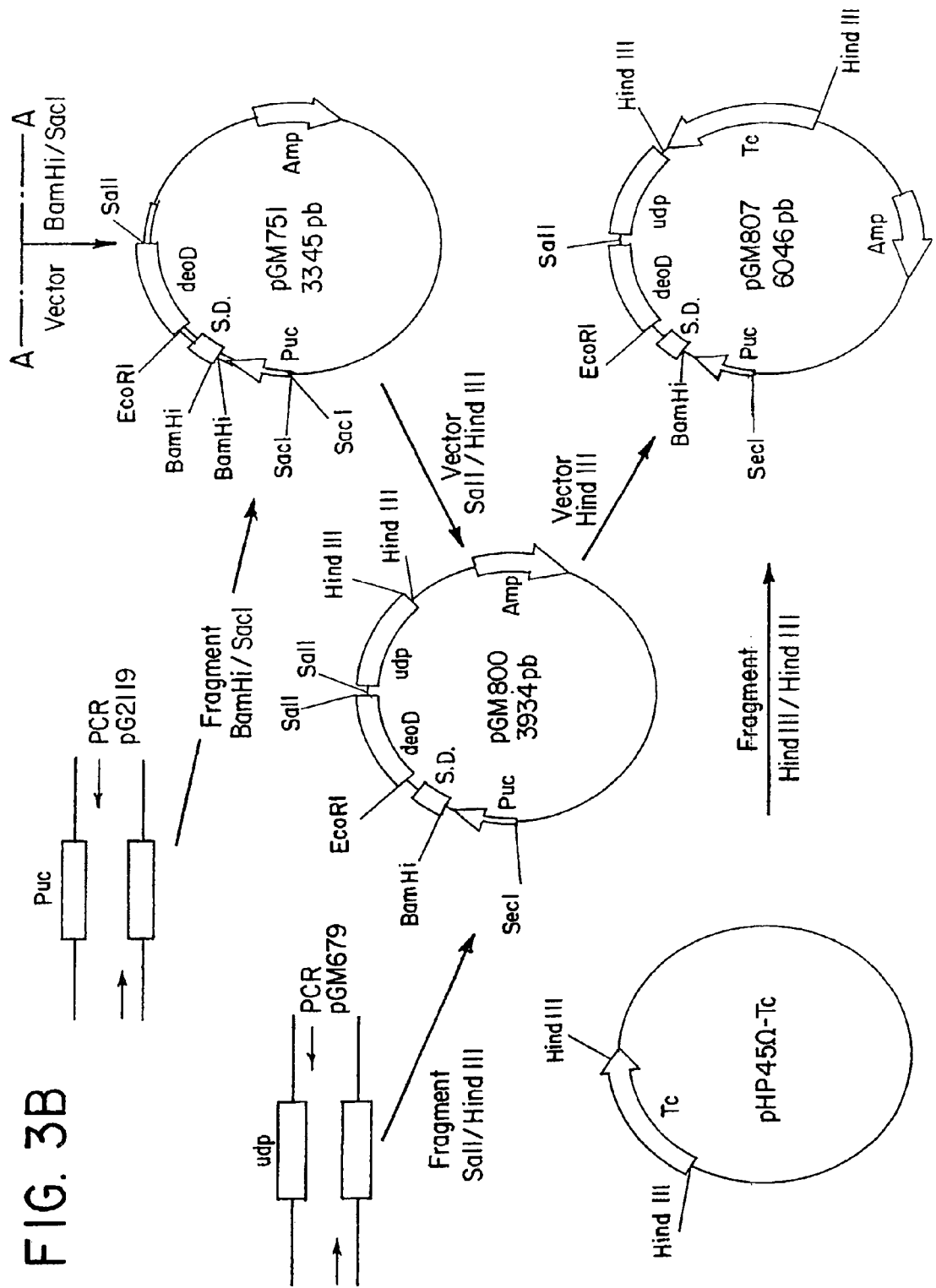

FIGS. 3A and 3B. Construction of cloning vectors for the expression of UdP and PNP enzymes.

Figure 4:
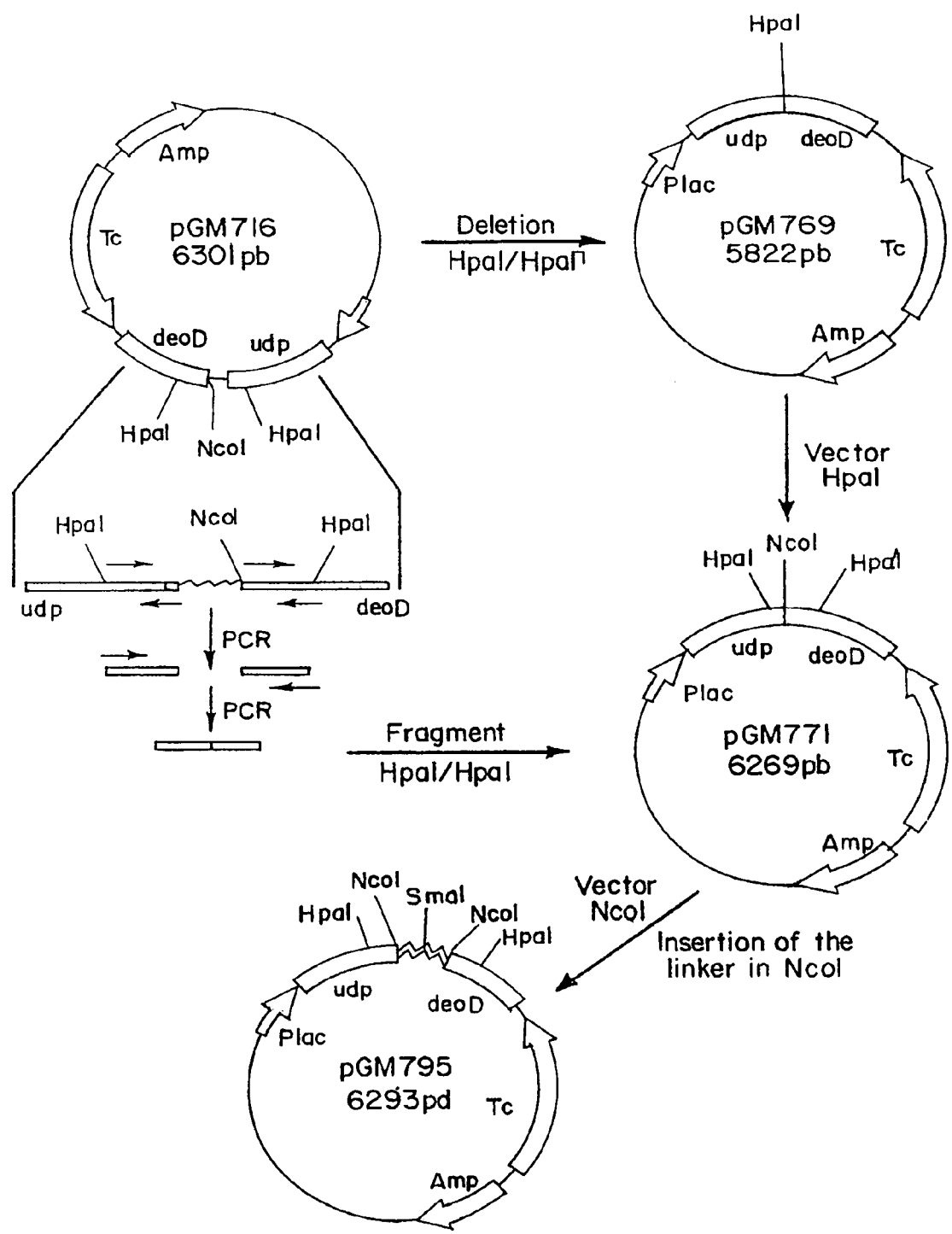

FIG. 4. Construction of cloning vectors for the expression of UdP-(L)-PNP enzymes.

FIG. 5. Expression of PNP and UdP in recombinant *E. coli* strains. Gel electrophoresis (SDS-PAGE) of total protein extracts from strains MG1655/pGM707, MG1655/pGM708, and MG1655/pGM716 grown overnight in LD medium supplemented with 12.5 mg/liter of tetracycline. Lanes 15, 2, and 0.3 correspond to protein extracted from 15, 2, and 0.3 ml of bacterial culture.

DETAILED DESCRIPTION

The methods for transforming a host bacteria cell with an expression vector and for isolating and purifying the expressed peptide are well known to any skilled in this art and are for example disclosed in Swartz J R, *Escherichia coli* recombinant DNA technology, and in Neidahrt F C et al. (edts), *Escherichia coli* and *Salmonella typhimurium*: Cellular and molecular biology, 2nd edition, pp 1693-1711, ASM, Washington, herein incorporated as a reference.

The hosts preferably used for the expression of the recombinant enzymes according to the present invention are bacterial cells of *Escherichia coli*; the strains K12 (preferably DH5α or MG1655) and/or the B strains are of particular interest. Alternatively, however, it is possible to use cells of other prokaryotic micro-organisms which are acceptable for industrial use because they are not dangerous to operators and the environment and they can be readily cultivated to obtain high levels of biomass.

As will also be seen from the Examples, the presence of a bacterial promoter, and in particular of the lac promoter, is not an essential element for the purposes of the present invention because it has been found that cell growth and the expression of polypeptides do not depend on the presence of an inducer (IPTG). For ease of performance, the gene sequence encoding a polypeptide having enzyme UdP activity and/or enzyme PNP activity is cloned into the plasmid pUC18 in the reading frame relative to the lac promoter.

Finally, the sequence coding for tetracycline resistance is preferably the Tet gene of pBR322; the sequence coding for kanamycin resistance is the kan gene of pET29c.

Figure 1:
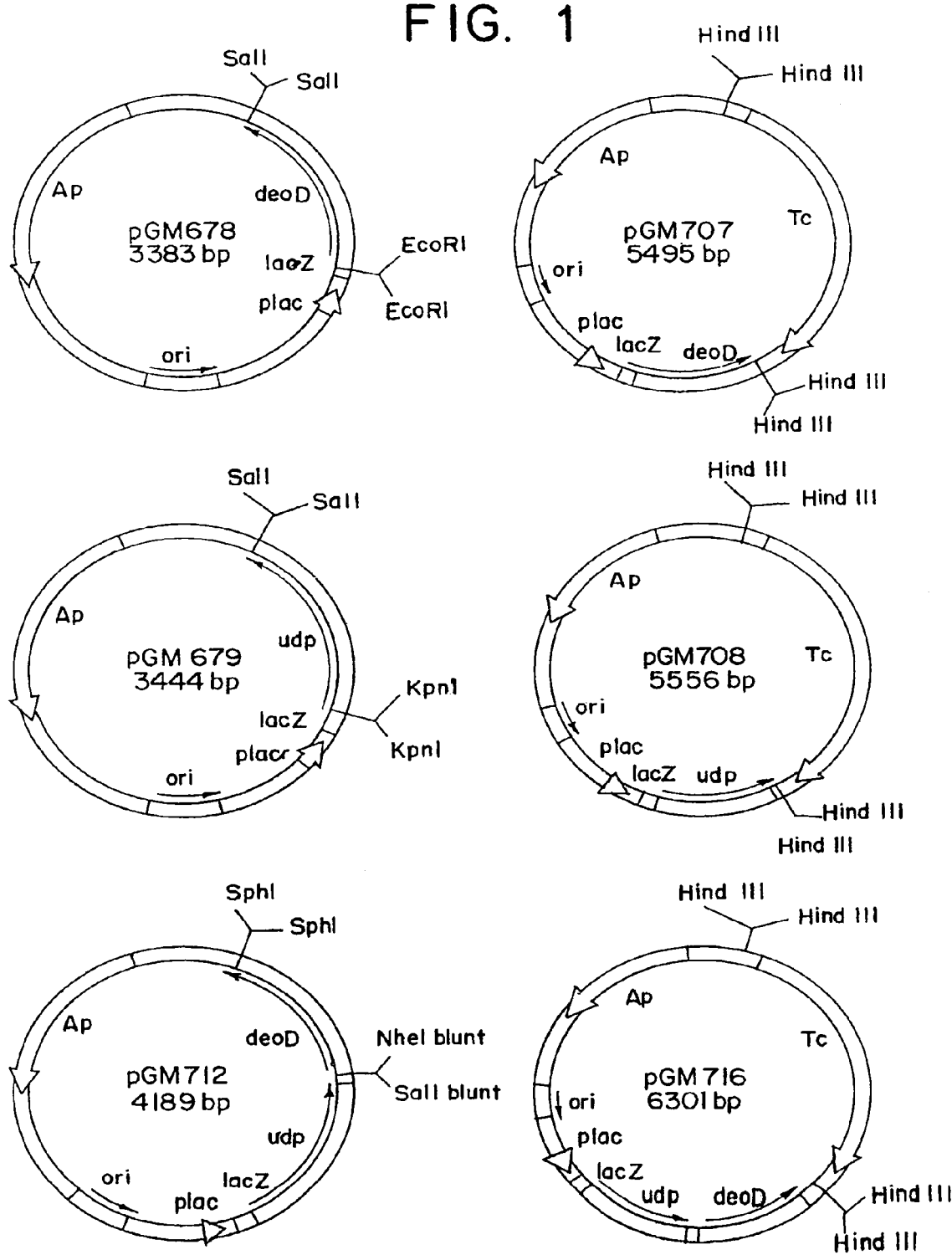
FIG. 1. Cloning vectors for the expression of UdP and PNP enzymes.

Thus, in accordance with well-known methods which will become clear from the Examples, the following plasmids, which are represented in FIGS. 1, 3 and 4, were constructed:

pGM679: udp gene cloned into plasmid pUC18 (SEQ ID NO 1). In the sequence numbering, coordinate 1 of pGM679 coincides with that of the pUC18 vector sequence; from nucleotide 1 to 242: pUC18 sequence; from 243 to 1021: *E. coli* udp gene sequence; from 1022 to 3444: pUC18 sequence.

pGM708: udp gene cloned into plasmid pUC18 together with the tetracycline resistance gene (SEQ ID NO 2). In the sequence numbering, coordinate 1 of pGM708 coincides with that of the pUC18 vector sequence; from nucleotide 1 to 242: pUC18 sequence; from 243 to 1021: *E. coli* udp gene sequence; from 1022 to 1039: pUC18 sequence; from 1040 to 1482: pHP45Ω sequence; from 1483 to 2883: pBR322 Tet gene sequence; from 2884 to 3151: pHP45Ω sequence; from 3152 to 5556: pUC18 sequence.

pGM678: deoD gene cloned into plasmid pUC18 (SEQ ID NO 3). In the sequence numbering, coordinate 1 of pGM678 coincides with that of the pUC18 vector sequence; from nucleotide 1 to 230: pUC18 sequence; from 231 to 960: *E. coli* deoD gene sequence; from 961 to 3383: pUC18 sequence.

pGM707: deoD gene cloned into plasmid pUC18 together with the tetracycline resistance gene (SEQ ID NO 4). In the sequence numbering, coordinate 1 of pGM707 coincides with that of the pUC18 vector sequence; from nucleotide 1 to 230: pUC18 sequence; from 231 to 960: *E. coli* deoD gene sequence; from 961 to 978: pUC18 sequence; from 979 to 1422: pHP45Ω sequence; from 1423 to 2822: pBR322 Tet gene sequence; from 2823 to 3090: pHP45Ω sequence; from 3091 to 5495: pUC18 sequence.

pGM712: udp and deoD genes cloned into plasmid pUC18 (SEQ ID NO 5). In the sequence numbering, coordinate 1 of pGM712 coincides with that of the pUC18 vector sequence; from nucleotide 1 to 242: pUC18 sequence; from 243 to 1021: *E. coli* udp gene sequence; from 1022 to 1025: pUC18 sequence; from 1026 to 1036: pBAD24 sequence; from 1037 to 1766: *E. coli* deoD gene sequence; from 1767 to 1792: pBAD24 sequence; from 1793 to 4189: pUC18 sequence.

pGM716: udp and deoD genes cloned into plasmid pUC18 together with the tetracycline resistance gene (SEQ ID NO 6). In the sequence numbering, coordinate 1 of pGM716 coincides with that of the pUC18 vector sequence; from nucleotide 1 to 242: pUC18 sequence; from 243 to 1021: *E. coli* udp gene sequence; from 1022 to 1025: pUC18 sequence; from 1026 to 1036: pBAD24 sequence; from 1037 to 1766: *E. coli* deoD gene sequence; from 1767 to 1792: pBAD24 sequence; from 1793 to 1794: pUC18 sequence; from 1795 to 2228: pHP45Ω sequence; from 2229 to 3628: pBR322 Tet gene sequence; from 3629 to 3896: pHP45Ω sequence; from 3897 to 6301: pUC18 sequence.

pGM709: gene deoD cloned in pBAD24 (SEQ ID NO 7). In the sequence numbering, coordinate 1 of pGM709 coincides with that of the pBAD24 vector sequence; from nucleotide 1 to 1311: pBAD24 sequence; from 1312 to 2042: sequence corresponding to 230-960 of pGM678; from 2043 to 5241: pBAD24 sequence.

pGM769: pGM716 with deletion of HpaI fragment (SEQ ID NO 8). In the sequence numbering, coordinate 1 of pGM769 coincides with that of pGM716 sequence; from nucleotide 1 to 914: pGM716 sequence; from nucleotide 915 to 5822: sequence corresponding to 1394-6301 of pGM716.

pGM771: genes udp and deoD cloned in pUC18 so to create a fusion between the two proteins; the plasmid also bears the tetracycline resistance gene (SEQ ID NO 9). In the sequence numbering, coordinate 1 of pGM771 coincides with that of pGM716 sequence; from nucleotide 1 to 1011: pGM716 sequence; from nucleotide 1012 to 6269: sequence corresponding to 1044-6301 of pGM716.

pGM795: genes udp and deoD cloned in pUC18 so to create a fusion between the two proteins bonded to each other via an aminoacidic linker; the plasmid also bears the tetracycline resistance gene (SEQ ID NO 10). In the sequence numbering, coordinate 1 of pGM795 coincides with that of pGM716 sequence; from nucleotide 1 to 1011: pGM771 sequence; from 1012 to 1041: linker sequence; from 1042 to 6299: sequence corresponding to 1044-6301 of pGM716.

pGM746: cloning vector derived from pUC18 (SEQ ID NO 11). In the sequence numbering, coordinate 1 of pGM746 coincides with that of the pUC18 vector sequence; from nucleotide 1 to 54: pUC18 sequence; from 55 to 109: pUC18 polylinker sequence; from 110 to 2297 pUC18 sequence.

pGM747: deoD gene cloned into pGM746 without upstream promoter (SEQ ID NO 12). In the sequence numbering, coordinate 1 of pGM747 coincides with that of pGM746; from nucleotide 1 to 79: pGM746 sequence; from 80 to 837:sequence corresponding to 1301-2058 of pGM709; from 838 to 3031: pGM746 sequence.

pGM751: deoD gene cloned downstream promoter ptac (SEQ ID NO 13). In the sequence numbering, coordinate 1 of pGM751 coincides with that of pGM747; from nucleotide 1 to 72: pGM747 sequence; from 73 to 171: ptac sequence from pGZ119; from 172 to 3128: pGM747 sequence.

pGM800: genes udp and deoD cloned downstream ptac promoter into a vector derived from pUC18 (SEQ ID NO 14). In the sequence numbering, coordinate 1 of pGM800 coincides with that of pGM751; from nucleotide 1 to 923: pGM751 sequence; from 924 to 1741: udp sequence corresponding to 203-1020 of pGM679; from 1742 to 3934: pGM751 sequence.

pGM807: genes udp and deoD cloned downstream ptac promoter into a vector containing the tetracycline resistance gene (SEQ ID NO 15). In the sequence numbering, coordinate 1 of pGM807 coincides with that of pGM800; from nucleotide 1 to 1742: pGM800 sequence; from 1743 to 3855: Tc sequence from pHP45α; from 3856 to 6046: pGM800 sequence.

The recombinant strains so obtained express polypeptides having enzyme UdP and PNP activity in large amounts, minimising any compatibility and/or solubility problems which can be caused by the presence of heterologous proteins.

In particular, the bacterial strains called DH5α/pGM678, MG1655/pGM678, DH5α/pGM707 and MG1655/pGM707 which overexpress the enzyme PNP; the strains DH5α/pGM679, MG1655/pMG679, DH5α/pGM708 and MG1655/pGM708 which overexpress the enzyme UdP; the strains DH5α/pGM712, DH5α/pGM716, MG1655/pGM716, DH5α/pGM800 and DH5α/pGM807 which overexpress the enzymes PNP and UdP simultaneously in the same cell; and the strains DH5α/pGM771, MG1655/pGM771, DH5α/pGM795, MG1655/pGM795, which overexpress the bifunctional fusion proteins UdP-(L)-PNP, were constructed. The efficiency of these novel strains, both as producers of the enzymes PNP and UdP and as biocatalysts for the preparation of nucleosides by bioconversion reactions, was compared with a preparation of Enterobacter aerogenes cells cultivated in the presence of inducers because that micro-organism, according to the data available in the literature, has hitherto been regarded as one of the best for catalysing transglycosylation reactions (Utagawa et al., Agric. Biol. Chem. 49, 1053-1058, 1985; Utagawa et al., Agric. Biol. Chem. 49, 2711-2717, 1985). The present invention relates also to the use of the novel recombinant strains in the production of polypeptides having enzyme UdP activity and/or enzyme PNP activity and/or as catalysts of transglycosylation reactions between a donor nucleoside and an acceptor base.

The enzyme activity of the recombinant strains was determined by incubating directly the cell suspension, or cell extracts obtained by mechanical and/or enzymatic lysis, in phosphate buffer with a pyrimidine nucleoside (for example uridine) to test for UdP activity or with a purine nucleoside (for example inosine) to test for PNP activity and by determining the formation of the pyrimidine base (uracil) or purine base (hypoxanthine), respectively, by reverse phase high pressure liquid chromatography (RP-HPLC), as indicated in Example 7.

Applying that test, the enzyme activities of UdP and PNP were measured in the recombinant bacterial strains to which the present invention relates and in the comparison E. aerogenes strain, to give the results indicated in Tables 1 and 2, which show that the recombinant strains of the present invention have enzyme activities up to approximately 10-30 times higher than that of the comparison strain cultivated under induction conditions and up to approximately 120-1000 times higher than that of the non-transformed E. coli host strains.

TABLE 1

Comparison of the enzyme activities of uridine phosphorylase (UdP) and purine nucleoside phosphorylase (PNP) in recombinant E. coli strains and in the comparison E. aerogenes strain.

| Novel bacterial strains according to the invention | UdP activity units/g of wet cells | PNP activity units/g of wet cells |
| --- | --- | --- |
| wild-type MG1655 | 4.5 ± 0.2 | 3.5 ± 0.2 |
| MG1655/pGM707 | 7.5 ± 0.1 | 2400.0 ± 50.0 |
| MG1655/pGM708 | 1550.0 ± 60.0 | 6.5 ± 0.5 |
| MG1655/pGM716 | 5400.0 ± 450.0 | 850.0 ± 30.0 |
| Comparison strain | | |
| Non-induced E. aerogenes ATCC 13048 | 3.7 ± 0.2 | 3.0 ± 0.2 |
| Induced E. aerogenes ATCC 13048 | 168.3 ± 2.9 | 19.0 ± 2.2 |

TABLE 2

Comparison of the enzyme activities of uridine phosphorylase (UdP) and purine nucleoside phosphorylase (PNP) assayed into the cell extracts of the recombinant E. coli strains MG1655 and DH5α, in the corresponding wild-type strains and in the non-induced and induced comparison E. aerogenes strains.

| Novel bacterial strains according to the invention | UdP activity units/g of wet cells | PNP activity units/g of wet cells |
| --- | --- | --- |
| non-transformed MG1655 | 9 ± 0.4 | 5 ± 0.3 |
| MG1655/pGM707 | 15 ± 0.2 | 996 ± 29 |
| MG1655/pGM708 | 3100 ± 120 | 10 ± 0.7 |
| MG1655/pGM716 | 6000 ± 160 | 643 ± 11 |
| non-transformed DH5α | 10 ± 1.0 | 3 ± 0.2 |
| DH5α/pGM707 | 14 ± 0.2 | 1000 ± 20 |
| DH5α/pGM708 | 10400 ± 750 | 4 ± 0.6 |
| DH5α/pGM716 | 6200 ± 150 | 600 ± 10 |
| E. aerogenes ATCC 13048 | 7.4 ± 0.4 | 4.5 ± 0.3 |
| Induced E. aerogenes ATCC 13048 | 335 ± 5 | 29 ± 3.3 |

The surprisingly high level of enzyme activity of these novel recombinant strains is confirmed by an indirect comparison with the strains described in JP-06-253854: the strains considered in the present invention permit enzyme activities from 340 to 1040 times (as regards the activity of UdP) and from 120 to 200 times (as regards the activity of PNP) higher than the enzyme activities of the non-transformed wild-type strains; the strains described in JP-06-

253854, on the other hand, have an enzyme activity in E. coli 150 and 91 times higher, respectively, than that of the corresponding wild-type strain. It is also noteworthy that the enzyme activity of the strains of the present invention was determined at 30° C. while that of the strains of JP-06-253854 was established while operating at 70° C., or at a temperature which permits markedly higher kinetics.

This high level of enzyme activity is also confirmed by the overexpression of the enzymes UdP and PNP which can be demonstrated both by electrophoretic analysis (FIG. 5) and by quantitative determination by RP-HPLC analysis which demonstrated levels of specific expression of from 55 to 120 milligrams of UdP/gram of wet cell paste and/or from 15 to 65 milligrams of PNP/gram of wet cell paste, as indicated in the example of Table 3.

TABLE 3

Quantitative determination of UdP and PNP expression levels by RP-HPLC analysis.

| Bacterial strains of the present invention | mg UdP/g wet cell paste | mg PNP/g wet cell paste |
|---|---|---|
| MG1655/pGM707 | — | 60 |
| MG1655/pGM716 | 55 | 15 |
| DH5α/pGM707 | — | 65 |
| DH5α/pGM708 | 120 | — |
| DH5α/pGM716 | 60 | 15 |

The whole cells of the recombinant strains described in the present invention, or their crude or purified extracts, can advantageously be used as biocatalysts for the preparation of natural nucleosides and modified analogues thereof starting from a sugar-donating nucleoside and from an acceptor base by means of bioconversion reactions which require the presence of only one type of phosphorylase (UdP or PNP) or the simultaneous presence of UdP and PNP according to the following general schemes:

a) pyrimidine nucleoside P1+pyrimidine base P2→pyrimidine nucleoside P2+pyrimidine base P1, in the presence of recombinant cells that overexpress UdP;

b) purine nucleoside P1+purine base P2→purine nucleoside P2+purine base P1, in the presence of recombinant cells that overexpress PNP;

c) pyrimidine nucleoside+purine base→purine nucleoside+pyrimidine base, in the presence of a mixture of recombinant cells that overexpress UdP and PNP separately or of cells of a single recombinant strain that co-expresses UdP and PNP;

d) purine nucleoside+pyrimidine base pyrimidine nucleoside+pyrimidine base, in the presence of a mixture of recombinant cells that overexpress UdP and PNP separately or of cells of a single recombinant strain that co-express UdP and PNP.

According to the information given in the literature, in the bioconversion reactions catalysed by UdP and PNP, there come into consideration as donor nucleosides both natural or modified nucleosides containing D-ribose and 2'-deoxyribose, and nucleosides containing the ribose group modified in the 2', 3' and/or 5' positions and, in particular, nucleosides in which the sugar is constituted by β-D-arabinose, α-L-xylose, 3'-deoxyribose, 3',5'-dideoxyribose, 2',3'-dideoxyribose, 5'-deoxyribose, 2',5'-dideoxyribose, 2'-amino-2'-deoxyribose, 3'-amino-3'-deoxyribose, 2'-fluoro-2'-deoxyribose. The acceptor bases which can be used in the bioconversion reactions catalysed by UdP and PNP are natural or substituted pyrimidine and purine bases, in particular purine bases substituted in the 1, 2 and/or 6 positions, pyrimidine bases substituted in the 3 and/or 5 positions and also other heterocyclic systems containing one or more nitrogen atoms, such as, for example, purine, 2-azapurine, 8-azapurine and substituted analogues thereof, 1-deazapurine (imidazopyridine), 3-deazapurine, 7-deazapurine and substituted analogues thereof, triazole and substituted analogues thereof, pyrazole and substituted analogues thereof, imidazole compounds and substituted analogues thereof.

Another method of preparing natural and modified nucleosides made possible by the present invention is to use recombinant cells or corresponding crude or purified cell extracts to catalyse the phosphorolysis reaction of a donor nucleoside (using UdP or PNP, depending on the base present in the donor nucleoside) and obtain α-sugar-1-phosphate which can optionally be isolated by chromatography, extraction or precipitation techniques and used in the subsequent reaction of transferring the sugar onto a suitable acceptor base in the presence of UdP or PNP (depending on the nature of the acceptor base).

The availability of recombinant bacterial strains which overexpress the UdP and PNP enzymes separately also enables the conditions of the transglycosylation reactions to be fixed, in terms of optimum activity of each of the two enzymes, by means of preliminary tests in which the reaction is carried out in the presence of mixtures containing varying proportions of cells of each of the two strains. For each transglycosylation reaction it is therefore possible to define, on an analytical scale, the optimum ratios of UdP and PNP enzyme activity while, in the subsequent preparative scale-up, it is possible to use either a mixture of cells of the two strains that express UdP and PNP individually, or only the strain that co-expresses UdP and PNP if their ratios are already optimum, or optionally the strain that co-expresses UdP and PNP, integrated with cells of strains expressing UdP or PNP. Such optimisation of the reaction conditions can be carried out using crude or purified cell extracts prepared from the cell paste of recombinant strains overexpressing UdP and PNP.

By way of example of optimisation of the bioconversion reactions in the present invention, a detailed description is given of the procedures relating to the preparation of 9-β-D-arabinofuranosyladenine(Ara-A) and 1-β-D-ribofuranosyl-1,2,4-triazole-3-carboxamide (ribavirin) which indicated that the best results were obtained with UdP:PNP activity ratios of 2:1 and 1:1, respectively, and with a concentration of 10 units/ml of UdP and 5 units/ml of PNP for Ara-A and 10 units/ml of either UdP or PNP for ribavirin. These enzyme activity ratios, or others found to be optimum for the reaction concerned, can be readily implemented using the recombinant strains described in the present invention, in order to optimise the concentration of cells to be used as biocatalysts, while at the same time obtaining the maximum bioconversion yield compatible with the constants of equilibrium of the enzyme reactions and a reduction in the reaction times. Analogously, it is possible to optimise all the transglycosylation reactions for the preparation of nucleosides and modified analogues thereof.

When the novel recombinant strains expressing the fusion proteins UdP-PNP or UdP-(L)-PNP (or the corresponding crude or purified extracts) are used for the bioconversion reactions, there is the advantage of using bifunctionals polipeptides in which the components having the activity of enzymes UdP and PNP are present in the stechiometric ratio 1:1. Furthermore, as nucleosides production via bioconversion is carried out by way of two successive reactions catalyzed respectively by UdP and PNP, the use of biocatalysts based on the bifunctionals fusion proteins UdP-PNP or UdP-(L)-PNP according to the present invention may improve the overall kinetic of the reactions thanks to a more efficient transfer of intermediates products from a reaction site to the other one.

The novel recombinant strains described in the present invention enable natural nucleosides and modified nucleosides to be prepared with significantly better results than those obtained by the enzyme techniques known hitherto which are based on the use of isolated enzymes or on the use of bacterial cells of wild-type micro-organism strains and cultivated micro-organism strains under conditions for inducing the activities of the phosphorylase enzymes.

A comparison of various transglycosylation reactions which were carried out using constant ratios between the concentration of donor nucleoside (60 mM) and acceptor base (20 mM) and in which a productivity parameter was calculated (Simon et al., Angew. Chem 24, 539-553, 1985) which, in addition to specific activity, also takes into account operating factors, such as, for example, intra-cellular and extra-cellular transport phenomena and the volumetric concentration of the end products, indicates that the use of the recombinant strains or of the corresponding crude or purified extracts to which the present invention relates is always characterised by greater bioconversion efficiency and by higher productivity per unit of time and of volume compared with the use of conventional micro-organisms (Table 4).

TABLE 4

Comparison of the efficiency of transglycosylation reactions catalysed by recombinant *Escherichia coli* cells (E) and by control *Enterobacter aerogenes* cells (C). The reactions were carried out at 60° C. for the time indicated, using the same concentrations of donor nucleoside (60 mM) and of acceptor base (20 mM). The bioconversion yield was calculated relative to the acceptor base by RP-HPLC analysis of the reaction mixture. The efficiency of the reaction is expressed by the productivity index P, calculated by the following formula $P = n \cdot m^{-1} \cdot t^{-1} \cdot 1000$ where n = concentration of the end product (g/l); m = wet cell paste (g/l of reaction mixture) and t = reaction time in hours.

| Product | Nucleoside 60 mM | Base 20 mM | Cell paste g/100 ml C | Cell paste g/100 ml E | t hours C | t hours E | Bioconversion % C | Bioconversion % E | P C | P E |
|---|---|---|---|---|---|---|---|---|---|---|
| Ribavirin | Uridine | 1,2,4-triazole-3-carbox-amide | 5 | 0.1 | 25 | 6 | 85 | 92 | 3 | 750 |
| 2'-deoxy-guanosine | 2'-deoxy-uridine | Guanine | 5 | 0.5 | 4 | 2 | 80 | 86 | 25 | 550 |
| 2'-deoxy-adenosine | 2'-deoxy-uridine | Adenine | 1 | 0.05 | 2 | 1 | 95 | 95 | 240 | 9600 |
| Thymidine | 2'-deoxy-uridine | Thymine | 0.5 | 0.05 | 1 | 3 | 59 | 60 | 600 | 2000 |
| 2'-deoxy-ribofuranosyl-2,6-diamino-purine | 2'-deoxy-uridine | 2,6-diamino-purine | 2 | 0.05 | 2 | 1.5 | 89 | 91 | 125 | 6660 |
| Ara-A | Ara-U | Adenine | 5 | 0.5 | 20 | 2 | 85 | 87 | 5 | 480 |

In particular, as shown in the example given in Table 5 regarding the preparation of Ara-A from Ara-U and adenine, the use of the recombinant strains enables conventional bioconversion processes to be improved both from the technical point of view and from the economic point of view and enables higher bioconversion yields, shorter reaction times, and a higher volumetric yield of end products to be obtained using a lower concentration of cells or corresponding crude or purified extract.

TABLE 5

Comparison of the operating conditions for the preparation of Ara-A by transglycosylation catalysed by recombinant *E. coli* cells and by a comparison *E. aerogenes* preparation.

| Operating conditions | Recombinant *E. coli* Cells | *E. aerogenes* Cells |
|---|---|---|
| Strain | MG1655/pGM716 or DH5α/pGM716 | Induced *E. aerogenes* ATCC 13048 |
| Ara-U:Adenine ratio | 75:75 (mM) | 40:40 (mM) |
| Cell concentration | 0.5% | 5% |
| Reaction time | 4 hours | 20 hours |

TABLE 5-continued

Comparison of the operating conditions for the preparation of Ara-A by transglycosylation catalysed by recombinant *E. coli* cells and by a comparison *E. aerogenes* preparation.

| Operating conditions | Recombinant *E. coli* Cells | *E. aerogenes* Cells |
|---|---|---|
| Bioconversion yield | 70% | 55% |
| Volumetric yield | 14 g Ara-A/liter | 5 g Ara-A/liter |

A further advantage derived from the use of the recombinant strains to which the present invention relates is the simplification of the processes for recovering and re-using the cell biomass or the corresponding crude or purified cell extract resulting from the presence of a lower cell concentration; thus, for example, any recovery of the cells or the extract by filtration or ultrafiltration and their subsequent recycling is considerably faster when the recombinant strains described in the present invention are used. In some cases, in particular when substrates having a high affinity for enzymes are used, the concentration of recombinant cells or of the corresponding crude or purified cell extract is reduced to such low values that it may be economically advantageous to avoid having to recover them, with a further simplification of the production process.

The purpose of the Examples given below is to illustrate the present invention without constituting a limitation of the field of application thereof.

Example No. 1

Cloning of the udp Gene of *Escherichia coli* into an Expression Vector

The *E. coli* udp gene sequence was found in the EMBL data bank with the accession number X15689. The gene was amplified by PCR with the oligonucleotides 5'-ATCGGTAC-CATCCATGTCCAAGTCTGATGTTTTTCATCTC-3' (SEQ ID NO:16) and 5'-AGACGGTCGACAAGAGAATTA-CAGCAGACGACGC-3' (SEQ ID NO: 17) from the *E. coli* strain K12 MG1655 (Singer et al., Microbiol. Rev. 53, 1-24, 1989). The amplified region comprises the entire sequence of the udp gene starting from the start codon ATG up to 7 bp downstream of the stop codon TAA. A KpnI restriction site was inserted at the 5' of the gene, followed by four bases selected at random. A SalI site is present at the 3' of the gene. The amplified fragment, digested with KpnI and SalI, was cloned into the polylinker region of the pUC18 vector which carries the ampicillin resistance gene (Yanish and Perron, Gene 33, 103-119, 1985; EMBL accession number L08752). After transformation of the DH5α strain (Hanahan, J. Mol. Biol. 166, 557-580, 1983), the pGM679 plasmid was obtained (FIG. 1). In the construct, a fusion is created between the first codons of the lacZ gene of pUC18 and the entire udp sequence (FIG. 2) and the transcription is under the control of the lac promoter of the vector.

The cloned region was completely sequenced and it was found to be completely identical with the data bank sequence. The pGM679 plasmid sequence is listed.

The pBR322 Tet gene, which confers tetracycline resistance (Bolivar et al., Gene 2, 95-113, 1977; EMBL accession number J01749) was then inserted into the pGM679 plasmid. The gene, preceded by its promoter, was obtained by HindIII digestion from the interposon pHP45W708-Tet (Fellay et al., Gene 52, 147-154, 1987) and cloned into the HindIII site of pGM679. The resultant plasmid was named pGM708 (FIG. 1). Its complete sequence is listed.

Example No. 2

Cloning of the deoD Gene of *Escherichia coli* into an Expression Vector

The *E. coli* deoD gene sequence was found in the EMBL data bank with the accession number M60917. The gene was amplified by PCR with the oligonucleotides 5'-CTGAAT-TCTTCCATGGCTACCCCACACATTAATGCAG-3' (SEQ ID NO: 18) and 5'-TCATGGTCGACTTACTCTTTATCGC-CCAGCAGAACG-3' (SEQ ID NO: 19) from the *E. coli* strain K12 MG1655 (Singer et al., Microbiol. Rev. 53, 1-24, 1989). The amplified region comprises the entire sequence of the deoD gene starting from the start codon ATG up to the stop codon TAA. An EcoRI restriction site was inserted at the 5' of the gene, followed by four bases selected at random. A SalI site is present at the 3' of the gene. The amplified fragment, digested with EcoRI and SalI, was cloned into the polylinker region of the pUC18 vector, which carries the gene for ampicillin resistance (Yanish and Perron, Gene 33, 103-119, 1985; EMBL accession number L08752). After transformation of the DH5cc strain (Hanahan, J. Mol. Biol. 166, 557-580, 1983), the pGM678 plasmid was obtained (FIG. 1). In the construct, a fusion is created between the first codons of the lacZ gene of pUC18 and the entire deoD sequence (FIG. 2) and the transcription is under the control of the lac promoter of the vector. The cloned region was completely sequenced and was found to be completely identical with the data bank sequence. The pGM678 plasmid sequence is listed.

The Tet gene, which confers tetracycline resistance, was then inserted into the pGM678 plasmid, in a manner analogous to that described in Example No. 1. The resultant plasmid was called pGM707 (FIG. 1). Its complete sequence is listed.

The deoD gene was also cloned in a different vector as reported herebelow.

The region PvuII-NdeI of pUC18 plasmid (end filled with Klenow) containing the replication origin was linked to the fragment EcoRI (filled)-HindIII (filled) containing the polylinker to obtain the resulting plasmid pGM746 whose sequence is listed. pGM746 was subsequently digested with BamHI (filled)-SphI and linked to fragment NheI (filled)-SphI of plasmid pGM709 in which is contained the deoD gene preceded by a Shine-Dalgarno sequence for the ribosome binding site (see example 3). The resulting plasmid was called pGM747 and its sequence is also listed.

The region containing the tac promoter was obtained by PCR amplification with oligonucleotides 5'-ATTGAGCTC-GACATCATAACGGTTCTGGC (SEQ ID NO: 20) and 5'-ATTGGATCCTGTGTGAAATTGTTATCCGC (SEQ ID NO: 21) of plasmid pGZ119 (Lessl et al., J. Bacteriol. 174, 2493-2500, 1992), digestion of the fragment with BamHI-SacI and insertion in BamHI-SacI of pGM747 upstream deoD. The resulting plasmid pGM751 (FIG. 3) contains the deoD gene starting from tac promoter and expresses the PNP enzyme identical to the wild-type one. The pGM751 sequence is listed.

Example No. 3

Cloning of the udp and deoD Genes into a Single Expression Vector

The udp and deoD genes were cloned into the same vector in order to express the UdP and PNP enzymes simultaneously inside the same cell. This was effected by inserting the deoD gene into the pGM679 plasmid, downstream of udp. For the construction, the EcoRI-SalI fragment of pGM678, containing the deoD gene, was cloned into the pBAD24 vector (Guzman et al., J. Bacteriol. 177, 4121-4230, 1995; EMBL accession number X81838) obtaining plasmid pGM709. The fragment NheI (with the ends filled)—SphI of this construct was cloned into pGM679, digested SalI (filled)-SphI, to give pGM712 (FIG. 1). In pGM712, both of the udp and deoD genes are transcribed starting from the lac promoter, but the translation of deoD is independent of that of udp because a sequence for the attachment of ribosomes is present upstream of deoD (FIG. 2). It will be appreciated that the PNP protein expressed by pGM712 is identical to the wild protein because the fusion with the first codons of lacZ at the 5' of the gene was eliminated (FIG. 2). The complete pGM712 sequence is listed.

The Tet gene, which confers tetracycline resistance, was subsequently inserted into the pGM712 plasmid as described in Example No. 1. The resultant plasmid was called pGM716 (FIG. 1). Its complete sequence is listed.

The udp and deoD genes were also cloned in a different vector in which they are simultaneously expressed in this order starting from tac promoter, as herebelow reported.

The fragment SalI-HindIII, obtained by PCR amplification using the pGM679 DNA as a template and the oligonucleotides 5'-TCCAGTCGACACAGGAAACAGCTATGA (SEQ ID NO: 22) and 5'-TACGAAGCTTA AGAGAATTA-CAGCAGACG (SEQ ID NO: 23), was inserted into plasmid pGM751, digested with SalI-HindIII, in order to obtain plasmid pGM800 bearing gene udp cloned downstream deoD. Both genes are transcribed starting from ptac but the transduction is independent. The complete sequence of pGM800 is listed.

The gene Tc for tetracycline resistance was subsequently inserted into pGM800 according to an analogous process to that reported in example 1, thus obtaining plasmid pGM807 (FIG. 3) whose sequence is also listed.

Example No. 4

Cloning of Fusion Proteins UdP-PNP and UdP-(L)-PNP

The sequence coding for UdP and PNP have been fused to each other either directly or separated by a short aminoacidic linker. The plasmids were obtained by subsequent steps starting from pGM716. In particular, plasmid pGM716 was digested with HpaI and closed again so to have the deletion in the terminal part of gene udp and in the starting part of deoD and create plasmid pGM769 with a unique site HpaI. The 3' portion of udp was amplified by PCR with the oligonucleotides 5'-GGCCGTTAACCGCACCCAGCAAGAG (SEQ ID NO: 24) and 5'-AGCCATGGACAGCAGAC-GACGCGCC (SEQ ID NO: 25); the 5' portion of deoD was amplified in the same way with the oligonucleotides 5'-GCT-GTCCATGGCTACCCCACACATTAAT (SEQ ID NO: 26) and 5'-CCGGGTTAACTTTGGAATCGGTGCAGG (SEQ ID NO: 27). Subsequently, using the product of the two PCRs as a template and the two extreme sequences, the complete region was amplified: the obtained fragment creates a fusion between udp and deoD, replacing the udp stop codon with a codon for serine, followed by deoD ATG codon. The fragment was digested with HpaI (site present at the two extremities) and cloned in pGM769 HpaI site. The resulting plasmid was called pGM771 (FIG. 4). In pGM771, the fused protein UdP-PNP is then transcribed starting from lac promoter. The plasmid sequence is listed.

Plasmid pM771 was subsequently modified by inserting the 5'-CATGGGCGGT GGCAGCCCGGGCATTCTGGC-CATG (SEQ ID NO: 28) linker in the unique NcoI site, immediately upstream the starting deoD ATG. The resulting plasmid, called pGM795 (FIG. 4) expresses a fusion protein formed by UdP+a 11 aminoacid linker (ser-met-gly-gly-gly-ser-pro-gly-ile-leu-ala) (SEQ ID NO: 29)+PNP. The pGM795 sequence is listed.

Example No. 5

Transformation of E. coli

The *E. coli* strain K12 DH5α, which carries the recA1 mutation (Hanahan, J. Mol. Biol. 166, 557-580, 1983) and the wild-type strain MG1655 (Singer et al., Microbiol. Rev. 53, 1-24, 1989) were transformed with plasmids pGM678, pGM679, pGM707, pGM708, pGM712, pGM716, pGM771, pGM795, pGM751, pGM800 and pGM807. The genotype of the strains and some characteristics of the recombinant strains are given in Tables 6 and 7. The pGM678, pGM679, pGM712, pGM751 and pGM807 transformants were selected on medium containing ampicillin (50 μg/ml) and the pGM707, pGM708, pGM716, pGM771, pGM795 and pGM907. pGM771, pGM795 and pGM807 transformants were selected on medium containing tetracycline (12.5 μg/ml).

TABLE 6

Genotype of the host strains

| Strain | Genotype | Reference |
|---|---|---|
| *E. coli* K12 DH5α | F⁻,φ80dlacZΔM15, Δ(lacZYA-argF)U169, deoR, recA1, endA1, hsdR17($r_{K^-}$, $m_{K^+}$), phoA, supE44, λ⁻, thi 1, gyrA96, relA1 | Hanahan, J. Mol. Biol. 166, 557-580, 1983 |
| *E. coli* K12 MG1655 | LAM-rph-1 | Singer et al., Microbiol. Rev. 53, 1-24, 1989 |

TABLE 7

Characteristics of the novel recombinant strains

| Name of the strain | Expression of the cloned proteins | Resistance |
|---|---|---|
| DH5α/pGM678 | purine nucleoside phosphorylase | ampicillin |
| DH5α/pGM679 | uridine phosphorylase | ampicillin |
| DH5α/pGM707 | purine nucleoside phosphorylase | tetracycline/ampicillin |
| DH5α/pGM708 | uridine phosphorylase | tetracycline/ampicillin |
| DH5α/pGM712 | purine nucleoside phosphorylase and uridine phosphorylase | ampicillin |
| DH5α/pGM716 | purine nucleoside phosphorylase and uridine phosphorylase | tetracycline/ampicillin |
| MG1655/pGM678 | purine nucleoside phosphorylase | ampicillin |
| MG1655/pGM679 | uridine phosphorylase | ampicillin |
| MG1655/pGM707 | purine nucleoside phosphorylase | tetracycline/ampicillin |
| MG1655/pGM708 | uridine phosphorylase | tetracycline/ampicillin |
| MG1655/pGM716 | purine nucleoside phosphorylase and uridine phosphorylase | tetracycline/ampicillin |
| DH5α/pGM771 | fusion protein UdP-PNP | tetracycline/ampicillin |
| DH5α/pGM795 | fusion protein UdP-(L)-PNP | tetracycline/ampicillin |
| MG1655/pGM771 | fusion protein UdP-PNP | tetracycline/ampicillin |
| MG1655/pGM795 | fusion protein UdP-(L)-PNP | tetracycline/ampicillin |
| DH5α/pGM751 | purine nucleoside phosphorylase | ampicillin |
| DH5α/pGM800 | purine nucleoside phosphorylase and uridine phosphorylase | ampicillin |
| DH5α/pGM807 | purine nucleoside phosphorylase and uridine phosphorylase | tetracycline/ampicillin |

The presence of the plasmid in the transformed strains was confirmed by extraction of the plasmid DNA and analysis on 0.6% agarose gel.

The growth of the transformed strains in LD broth (composition per liter: 10 g Bactotryptone (Difco), 5 g Yeast extract (Difco), 5 g NaCl) or in solid medium (LD+10 g/l agar), to which was added ampicillin (50 µg/ml) or tetracycline (12.5 µg/ml, only for the strains transformed with pGM707, pGM708, pGM716, pGM771, pGM795 and pGM807) is comparable to that of the control strains transformed with the pUC18 vector. In addition, the strains transformed with the plasmids pGM707, pGM708, pGM716, pGM771, pGM795 and pGM807, carrying both resistance genes, do not demonstrate differences in growth in the presence of ampicillin and tetracycline.

Example No. 6

Evaluation of the Expression of the UdP and PNP Proteins in the Recombinant Strains Precultures of the recombinant strains were obtained by inoculating single clones into LD medium to which an antibiotic had been added and by incubating without agitation at 37° C. overnight. The cultures were diluted 1:20 in LD medium+antibiotic in a flat-bottomed flask and incubated at 37° C. with agitation until the stationary phase was reached, corresponding to cell density values of approximately 2 units of optical density at 600 nm. The total proteins extracted from 1 ml of culture were separated on 15% polyacrylamide gel under reducing conditions (SDS-PAGE) and the proteins were visualised by staining with Coomassie Blue. The PNP and UdP proteins were identified on the basis of the molecular weight of approximately 26.6 kDa for PNP and 28.2 kDa for UdP. The result obtained from the extracts of strains MG1655/pGM707, pGM708 and pGM716 is given in FIG. 5. Electrophoretic analysis shows that, in all the samples studied, overexpression of UdP and PNP has occurred, because the corresponding protein bands represent a significant percentage of the total cell proteins; this result is confirmed by the quantitative determination of the enzyme activities which is given in Tables 1 and 2 and by the quantitative determination of UdP and PNP expression effected by reverse phase high pressure liquid chromatography (RP-HPLC). For that purpose, the soluble extract was analysed on a C4-Vydac analytical column, dimensions 4.6×250 mm, using a mobile phase constituted by acetonitrile-$H_2O$ containing 0.1% trifluoroacetic acid and operating in accordance with the following parameters: flow rate of 0.75 ml/minute; elution with a gradient from 40% acetonitrile to 65% acetonitrile in 30 minutes; temperature of 45° C.; UV detection at a wavelength of 215 nm. Under the analysis conditions applied, the elution times for UdP and PNP were approximately 13 minutes and 15 minutes, respectively. The quantitative determination was carried out by comparing the area of the peak of interest with the area of the peak of standard UdP and PNP preparations separated under the same conditions as the samples.

Because, in the recombinant strains, the deoD and udp genes are cloned under the control of the lac promoter, the growth of the cells and the expression of the UdP and PNP proteins were monitored both in the absence and in the presence of 40 mg/l of IPTG as transcription inducer. The results obtained indicated that the presence of IPTG does not modify cell growth and does not increase the level of PNP and UdP expression (possibly due to the insufficient amount of repressor in those strains). This last result indicates that, in the recombinant strains to which the present invention relates, the expression of the deoD and udp genes is constitutive and reaches very high levels without phenomena of cell damages or diminished cell vitality.

Example No. 7

Determination of the Enzyme Activity of Uridine Phosphorylase and Purine Nucleoside Phosphorylase Expressed Intracellularly in Recombinant Bacterial Cells The strains were grown as described in Example No. 5. The cells were harvested by centrifugation, weighed in the form of wet cell paste and stored at −20° C. until enzyme analysis was carried out.

The activity of the UdP enzyme was determined in a phosphorolysis test by incubating for 5 minutes at 30° C. the soluble fraction (cell extract) obtained by sonication of a known amount of a suspension of the cell paste and by centrifugation of the homogenate in 100 mM-pH 7 phosphate buffer containing 60 mM of the uridine substrate. The enzyme reaction was blocked by acidification with 0.1N HCl; the suspension was filtered and analysed by RP-HPLC on a C18 column (Hypersyl 100; 4.6×250 mm), eluting under isocratic conditions with a mobile phase constituted by 0.02 M $K_2HPO_4$ in methanol-$H_2O$ (4:96 v/v) and adjusted to pH 4.5 with $NH_4OH$. The amount of uracil formed in the reaction was determined by reference to a standard curve and the enzyme activity of the cell preparation was calculated in µmol uracil/min/g wet cell paste (units/g). The activity of the PNP enzyme was determined in a phosphorolysis test by incubating for 10 minutes at 30° C. the soluble fraction (cell extract) obtained by sonication of a known amount of a suspension of the cell paste and by centrifugation of the homogenate in 100 mM-pH 7 phosphate buffer containing 50 mM of the inosine substrate. The enzyme reaction was blocked by acidification with 0.1N HCl; the suspension was filtered and analysed by RP-HPLC on a C18 column (Hypersyl 100; 4.6×250 mm), eluting under isocratic conditions with a mobile phase constituted by 0.02 M $K_2HPO_4$ in methanol-$H_2O$ (4:96 v/v) and adjusted to pH 4.5 with $NH_4OH$. The amount of hypoxanthine formed in the reaction was determined by reference to a standard curve and the enzyme activity of the cell preparation was calculated in µmol hypoxanthine/min/g wet cell paste (units/g).

Example No. 8

Fermentation of the Recombinant Strains

The recombinant strains to which the present invention relates were cultivated at high biomass either under batch mode or under fed-batch mode fermentation conditions.

The batch-mode fermentations were carried out using a fermenter having a working volume of 10 liters which was filled with 9 liters of medium having the following composition (per liter): 0.6 g $KH_2PO_4$; 3.2 g $K_2HPO_4$; 20 g Soytone (Difco); 36 g yeast extract (Difco); 1 g $MgSO_4$-$7H_2O$; 0.0125 g tetracycline (or other antibiotic used as a selection marker) and which was inoculated with 1 liter of a bacterial suspension previously cultivated for 20 hours at 30° C. in medium having the following composition, per liter: 20 g tryptone; 10 g yeast extract; 10 g NaCl; 0.0125 g tetracycline.

The fermentation was carried out in accordance with the following operating parameters: 30° C.; air flow of 1 liter/liter of culture/minute; initial agitation 250 rev/min modified automatically to maintain a level of $O_2$ at 20% of the saturation concentration; pH maintained at 7 by additions of H₃PO₄ or NH₄OH; time 24 hours. When fermentation was complete, the culture medium was centrifuged, the cell pellet was washed in 30 mM-pH 7 phosphate buffer. The biomass obtained (40-50 grams of wet cell paste/liter of culture medium) was stored at −20° C. until it was brought into use.

The fed-batch mode fermentations were carried out using a fermenter having a working volume of 10 liters which was filled with 7 liters of medium at pH 6.8-7 having the following composition, per liter: 13.3 g KH$_2$PO$_4$; 4 g (NH$_4$)$_2$HPO$_4$; 1.25 g Soytone (Difco); 0.125 extract (Difco); 1.7 g citric acid; 2.5 g glycerol; 1.5 g MgSO$_4$-7H$_2$O; 0.08 g CaCl$_2$; 0.01 g thiamine, 0.0125 g tetracycline (or other antibiotic selector); 0.08 g FeSO$_4$-7H$_2$O; 0.02 g MnSO$_4$-H$_2$O; 0.03 g ZnSO$_4$-7H$_2$O; 0.003 g H$_3$BO$_3$; 0.06 g CuSO$_4$-5H$_2$O; 0.008 g CoCl$_2$-6H$_2$O; 0.004 g NaMoO$_4$-2H$_2$O. The fermenter was inoculated with 1 liter of bacterial suspension previously cultivated for 18-20 hours at 30° C. in medium having the following composition, per liter: 13.3 g KH$_2$PO$_4$; 4 g (NH$_4$)$_2$HPO$_4$; 5 g Soytone (Difco); 1.7 g citric acid; 10 g glycerol; 0.01 g thiamine; 0.0125 g tetracycline; 0.05 g CaCl$_2$-2H$_2$O; 1 g MgSO$_4$-7H$_2$O; 0.03 g FeSO$_4$-7H$_2$O; 0.01 g MnSO$_4$-H$_2$O; 0.01 g ZnSO$_4$-7H$_2$O; 0.003 g H$_3$BO$_3$; 0.02 g CuSO$_4$-5H$_2$O; 0.002 g CoCl$_2$-6H$_2$O; 0.002 g NaMoO$_4$-2H$_2$O.

The fermentation was carried out in accordance with the following operating parameters: 30° C.; air flow of 1-1.2 liter/liter of culture/minute; initial agitation 150 rev/min modified automatically to maintain a level of O$_2$ at 20% of the saturation concentration for approximately 8-10 hours (batch phase) and subsequently a level of 0$_2$ at 10% of the saturation concentration (fed-batch phase); pH maintained at 6.8-7 by additions of H$_3$PO$_4$ or NH$_4$OH. During the fed-batch phase, the fermentation was automatically supplied with a total of 2 liters of a solution having the following composition, per liter: 400 g glycerol; 200 g Soytone; 20 g yeast extract; 3 g MgSO$_4$-7H$_2$O; 0.0125 g tetracycline. When fermentation was completed (after approximately 50 hours) the culture medium was centrifuged, the cell pellet was washed in 30 mM-pH 7 phosphate buffer. The biomass obtained (150-200 grams of wet cell paste/liter of culture medium) was stored at −20° C. until it was brought into use.

Example No. 9

Transglycosylation Reactions on a Laboratory Scale and Calculation of the Productivity Index The transglycosylation reactions were carried out using various sugar-donating nucleosides at a concentration of 60 mM (uridine, 2'-deoxyuridine, Ara-U) and various acceptor bases at a concentration of 20 mM (1,2,4-triazole-3-carboxamide, guanine, adenine, thymine, 2,6-diaminopurine) at pH 7 in phosphate buffer (30 mM) in the presence of various concentrations of cell paste or corresponding crude or purified extract derived either from cultures of the control microorganism E. aerogenes or from cultures of the recombinant E. coli strain MG1655/pGM716 which overexpresses the UdP and PNP enzymes. The reactions were carried out at 60° C. for various periods of time (from 1 hour to 25 hours) and the percentage bioconversion, relative to the initial concentration of acceptor base, was determined by RP-HPLC analysis of the diluted reaction mixture. The results obtained are given in Table 2.

The productivity index P was calculated for each reaction by applying the following formula:

$$P = n \cdot m^{-1} \cdot t^{-1} \cdot 1000$$

where n=concentration of the end product (g/l)
m=wet cell paste (g/l of reaction mixture)
t=reaction time in hours.

The productivity index represents an overall measure of the efficiency of the reaction because it takes into account both the characteristics of the enzyme-substrate interaction itself and operating parameters, such as the reaction time, the amount of cells used and the volumetric yield of end product.

Example No. 10

Optimisation of the Use of Recombinant E. coli Cells in Transglycosylation Reactions The preparation of ribavirin starting from uridine (60 mM) and 1,2,4-triazole-3-carboxamide (40 mm) and of Ara-A starting from Ara-U (40 mM) and adenine (40 mM) were studied as examples of optimisation of the use of recombinant E. coli cells in bioconversion reactions. In each case, the reactions were carried out at 60° C. in the presence of 30 mM of potassium phosphate at pH 7 and in the presence of various amounts of cell paste obtained by fermentation of the strains MG1655/pGM707 (overexpressing the UdP enzyme) and MG1655/pGM708 (overexpressing the PNP enzyme). At predetermined intervals, aliquots of the reaction mixture were taken and analysed by RP-HPLC in order to determine the percentage bioconversion (calculated relative to the concentration of acceptor base).

The study was initially carried out by incubating the reaction mixture for 20 hours in the presence of a limiting concentration of cell paste (with total enzyme activity equal to or less than 2 units/ml) and by operating in such a manner as to have ratios of UdP enzyme units and PNP enzyme units varying in the following proportions 5:1; 2:1; 1:1; 1:2; 1:5.

The results obtained in the two bioconversion reactions are given in Table 8.

TABLE 8

Study of the transglycosylation reaction conditions
The reactions were carried out for 20 hours at 60° C.
in the presence of limiting concentrations of cell paste.

| Preparation of ribavirin | | | Preparation of Ara-A | | |
|---|---|---|---|---|---|
| UdP units/ml | PNP | Bioconversion yield % | UdP units/ml | PNP | Bioconversion yield % |
| 1 | 0.2 | 60.7 | 1 | 0.2 | 54.0 |
| 1 | 0.5 | 77.3 | 1 | 0.5 | 65.2 |
| 1 | 1 | 81.6 | 1 | 1 | 63.8 |
| 0.5 | 1 | 80.0 | 0.5 | 1 | 26.4 |
| 0.2 | 1 | 78.1 | 0.2 | 1 | 9.2 |

The results given in the Table demonstrate that the optimum UdP and PNP activity ratios are 1:1 and 0.5, respectively, for the reaction for the formation of ribavirin and Ara-A.

These data were confirmed in the subsequent study in which enzyme concentrations 10 times higher were used, with the same proportions being maintained between the UdP units and the PNP units; in this study, the reaction kinetics were also determined by taking samples of reaction mixture at intervals of 1 hour for RP-HPLC analysis and calculation of the percentage bioconversion.

Tables 9 and 10 show, for the ribavirin and Ara-A preparation reactions, respectively, the optimum parameters in terms of percentage bioconversion and reaction time for the various proportions of UdP and PNP studied.

TABLE 9

Optimisation of the reaction conditions for the preparation of ribavirin

| UdP units/ml | PNP units/ml | Reaction time hours | Bioconversion % |
|---|---|---|---|
| 10 | 2 | 20 | 89.4 |
| 10 | 5 | 4 | 89.5 |
| 10 | 10 | 2 | 91.2 |
| 5 | 10 | 2 | 91.2 |
| 2 | 10 | 2 | 91.1 |

TABLE 10

Optimisation of the reaction conditions for the preparation of Ara-A.

| UdP units/ml | PNP units/ml | Reaction time hours | Bioconversion % |
|---|---|---|---|
| 10 | 2 | 3 | 70.5 |
| 10 | 5 | 2 | 70.8 |
| 10 | 10 | 2 | 70.6 |
| 5 | 10 | 6 | 70.1 |
| 2 | 10 | 6 | 70.0 |

The results of the optimisation study indicate that ribavirin can be obtained in two hours with a bioconversion yield of 91% using 10 units/ml of either UdP or PNP while Ara-A can be obtained in two hours with a bioconversion yield of approximately 71% using 10 units/ml of UdP and 5 units/ml of PNP.

On the basis of the enzyme activity titre of the recombinant *E. coli* strains described in the present invention, it is therefore possible to calculate the amount of cell paste necessary to prepare ribavirin and Ara-A under optimum conditions. In the case, for example, of the strains MG1655/pGM707 and MG1655/pGM716 having the specific activities given in Table 1, 0.4 and 0.2 gram of wet cell paste/100 ml of reaction mixture, respectively, will be used for the preparation of ribavirin and Ara-A.

Example No. 11

Pilot-Scale Preparation of Ara-A by Transglycosylation Reaction Carried out with the *E. aerogenes* Comparison Strain, with the Recombinant *E. coli* Strains and with the Corresponding Cell Extracts The process for the preparation of Ara-A by transglycosylation catalysed by *E. aerogenes* cells or by recombinant cells of *E. coli* MG1655/pGM716 or DH5α/pGM716 overexpressing UdP and PNP was studied on a reaction scale of 1000 liters.

50 kg of wet cell paste obtained by fermenting *E. aerogenes* were resuspended in approximately 200 liters of 30 mM phosphate buffer at pH 7 and mixed with 800 liters of phosphate buffer in which had been dissolved at elevated temperature 5.4 kg of adenine (final concentration 40 mM) and 8.9 kg of Ara-U (final concentration 40 mM). The mixture was maintained at 60° C., with agitation, for 20 hours, diluted to approximately 3000 liters with hot $H_2O$ and subjected to diafiltration on a membrane, collecting approximately 5000 liters of ultrafiltrate. The bioconversion yield determined by RP-HPLC was approximately 55%. The residue containing the cell paste is used for a subsequent reaction. The ultrafiltrate was concentrated to approximately 1000 liters and cooled to collect the precipitate constituted by Ara-A contaminated with non-reacted adenine (approximately 30 g of adenine per 100 g of Ara-A). 5 kg of Ara-A (total yield approximately 46%) with a degree of purity higher than 99.5% were finally obtained after crystallisation with $H_2O$.

5 kg of wet cell paste or the corresponding crude or purified extract obtained by fermenting the strain MG1655/pGM716 or the strain DH5α/pGM716 were resuspended in approximately 20 liters of 30 mM phosphate buffer at pH 7 and mixed with 980 liters of phosphate buffer in which had been dissolved at elevated temperature 10.1 kg of adenine (final concentration approximately 74.6 mM) and 18.3 kg of Ara-U (final concentration approximately 74.6 mM). The mixture was maintained at 60° C., with agitation, for 4 hours to obtain a bioconversion yield of approximately 70%. The cell paste was recovered in order to be used again in subsequent reactions by dilution at elevated temperature and diafiltration in accordance with the procedure described above. The ultrafiltrate was concentrated to a volume of approximately 1000 liters, cooled to collect the precipitate constituted by Ara-A which was subsequently crystallised from water to obtain approximately 14 kg of Ara-A with a degree of purity higher than 99.5%. According to an alternative procedure, in which the cells were not recovered and the diafiltration step was omitted, at the end of the reaction the mixture was heated to approximately 90° C. and filtered at elevated temperature to eliminate the cells, and the filtrate was cooled to precipitate Ara-A contaminated with non-reacted adenine (approximately 20 g of adenine per 100 g of Ara-A). 14 kg of Ara-A (total yield 65%) having a degree of purity higher than 99.5% were finally obtained after crystallisation from reaction of 1000 liters. Similar results were obtained starting from a mixture of the cell pastes or the corresponding crude or purified extracts obtained by fermenting the recombinant *E. coli* strains MG1655/p707 or MG1655/p708 and the strains DH5α/pGM707 or DH5α/pGM707 overexpressing UdP and PNP, respectively.

What is claimed is:

1. A method of catalyzing transglycosylation reactions between a donor nucleoside and an acceptor base comprising culturing transformed *Escherichia coil* host cells, said host cells: (i) expressing 340-1040 times higher uridine phosphorylase activity, 120-200 times higher purine nucleoside phosphorylase activity, or both, than corresponding non-transformed *E. coli* host cells, and (ii) transformed with a plasmid expression vector, said plasmid expression vector comprising: a) a polynucleotide encoding a uridine phosphorylase (UdP) polypeptide, wherein said polynucleotide comprises the sequence of nucleotides 243 to 1021 of SEQ ID NO: 6, or a polynucleotide encoding a purine nucleotide phosphorylase (PNP) polypeptide, wherein said polynucleotide comprises the sequence of nucleotides 1037 to 1766 of SEQ ID NO: 6, or both of said polynucleotides encoding UdP and PNP polypeptides; and b) at least one polynucleotide encoding a tetracycline or kanamycin resistance protein or a combination of polynucleotides encoding tetracycline and kanamycin resistance proteins iii) mixing a cell paste, cell extract, or purified enzyme(s) from said transformed *E. coli* host cells with a nucleoside and acceptor base, wherein the cell paste, cell extract, or purified enzyme(s) comprises at least one of said UdP and PNP polypeptides, and iv) catalyzing transglycosylation reactions between the donor nucleoside and the acceptor base.

2. The method according to claim 1, wherein the polynucleotides of a) and b) are cloned into a pUC18 plasmid.

3. The method according to claim 1, wherein the polynucleotide encoding a tetracycline resistance protein is a Tet gene of plasmid pBR322.

4. The method according to claim 1, wherein the polynucleotide encoding a kanamycin resistance protein is a kan gene of plasmid pET29c.

5. The method according to claim 1, wherein the acceptor base is a purine or pyrimidine base.

6. The method according to claim 5, wherein the purine or pyrimidine base is natural or substituted.

7. The method according to claim 6, wherein the substituted purines base is selected from the group consisting of purine, 2-azapurine, 8-azapurine, 1-deazapurine (imidazopyridine), 3-deazapurine, and 7-deazapurine.

8. The method according to claim 6, wherein the purine base is substituted at least one of the 1, 2 and 6 positions of the purine ring and the pyrimidine base is substituted at least one of the 3 and 5 positions of the pyrimidine ring.

9. The method according to claim 1, wherein the acceptor base is a heterocyclic compound containing at least one nitrogen atom.

10. The method according to claim 9, wherein the heterocyclic compound is selected from the group consisting of imidazole, triazole and pyrazole.

11. The method according to claim 1, wherein the donor nucleoside is selected from nucleosides containing D-ribose and 2' deoxyribose.

12. The method according to claim 1, wherein the donor nucleoside contains the a ribose group modified in the 2', 3', or 5' position.

13. The method according to claim 1, wherein a sugar of the donor nucleoside is selected from the group consisting of β-D-arabinose, α-L-xylose, 3-deoxyribose, 3,5'-dideoxyribose, 2',3'-dideoxyribose, 5'-deoxyribose, 2',5'-dideoxyribose, 2'-amino-2'-deoxyribose, 3'-amino-3'-deoxyribose, and 2'-fluoro-2'-deoxyribose.

* * * * *